United States Patent
Puschl et al.

(10) Patent No.: US 8,067,410 B2
(45) Date of Patent: Nov. 29, 2011

(54) PHENOLIC AND CATECHOLIC AMINES AND PRODRUGS THEREOF

(75) Inventors: Ask Puschl, Frederiksberg (DK);
Morten Jorgensen, Bagsvaerd (DK);
Benny Bang-Andersen, Copenhagen (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 261 days.

(21) Appl. No.: 12/490,610

(22) Filed: Jun. 24, 2009

(65) Prior Publication Data

US 2009/0325946 A1    Dec. 31, 2009

Related U.S. Application Data

(60) Provisional application No. 61/076,470, filed on Jun. 27, 2008.

(51) Int. Cl.
| | |
|---|---|
| C07D 265/38 | (2006.01) |
| C07D 498/02 | (2006.01) |
| C07D 413/06 | (2006.01) |
| A61K 31/536 | (2006.01) |
| A61K 31/5365 | (2006.01) |

(52) U.S. Cl. ........................ 514/229.5; 544/101
(58) Field of Classification Search .................. 544/101; 514/229.5

See application file for complete search history.

(56) References Cited

FOREIGN PATENT DOCUMENTS
| | | |
|---|---|---|
| EP | 0 077 754 | 4/1983 |
| WO | WO 97/03054 | 1/1997 |
| WO | WO 2009/026934 | 3/2009 |
| WO | WO 2009/026935 | 3/2009 |

OTHER PUBLICATIONS

Perrone, et al. Medicinal Chemistry Research, vol. 1, No. 6, Jan. 1, 1991, pp. 388-392.
International search report for International PCT publication No. WO 2009/156458.

*Primary Examiner* — Kahsay T Habte
(74) *Attorney, Agent, or Firm* — Stephen G. Kalinchak; Kitae Lim

(57) ABSTRACT

The present invention relates to novel phenolic and catecholic amines of Formula I, to processes for their preparation, pharmaceutical compositions containing them, to their use in therapy and to their use in radiolabeled form as PET- or SPECT ligands.

24 Claims, 3 Drawing Sheets

Crystal structure of (+)-(4aS,10aS)-4-*cyclo*-propylmethyl-3,4,4a,5,10,10a-hexahydro-2H-naphtho[2,3-b][1,4]oxazin-9-ol hydrochloride (example 5d2). Absolute configuration determined by the anomalous scattering of the 'heavy' chlorine atom.

Crystal structure of (2R,4aR,10aR)-2-Methylsulfanylmethyl-4-*n*-propyl-3,4,4a,5,10,10a-hexahydro-2H-naphtho [2,3-b][1,4]oxazin-9-ol hydrochloride (example 5J).

Crystal structure of Toluene-4-sulfonic acid (2R,4aS,10aS)-9-methoxy-4-propyl-3,4,4a,5,10,10a-hexahydro-2H-naphtho[2,3-b][1,4]oxazin-2-ylmethyl ester (intermediate VB).

PHENOLIC AND CATECHOLIC AMINES AND PRODRUGS THEREOF

CROSS-REFERENCE TO RELATED APPLICATIONS

The present application is a U.S. Non-Provisional Application which claims the benefit of U.S. Provisional Patent Application Ser. No. 61/076,470, filed Jun. 27, 2008, which is herein incorporated by reference in its entirety.

FIELD OF THE INVENTION

The present invention relates to new phenolic and catecholic amines as well as to prodrug derivatives for their formation in vivo; to processes for their preparation, pharmaceutical compositions containing them, and their use in therapy.

BACKGROUND OF THE INVENTION

Neurodegenerative diseases are becoming more prevalent with the aging population. One particular neurodegenerative disease, which typically has its onset between the ages of 50 and 80 years of age is Parkinson's disease (PD). PD is a disorder of the brain which is characterized by tremor and difficulty with walking, movement, and coordination.

Parkinson's disease appears to be caused by a progressive deterioration of dopamine-containing neurons in the substantia nigra zona compacta of the brain. Dopamine (DA) is a chemical neurotransmitter, which is utilized by brain cells to transmit impulses to control or modulate peripheral muscle movement. The loss of dopamine-containing neurons results in reduced amounts of dopamine available to the body. This process is thought to disturb nerve cell function such that impulses are not transmitted properly, resulting in a loss of muscle control and function.

Currently, there is no known cure for PD. Treatments are typically aimed at controlling the PD symptoms, primarily by replacing the dopamine, either with L-DOPA which is metabolized to dopamine, or by administering chemical agents that stimulate the dopamine receptors. These receptors fall into two broad classes, D1-type and D2-type receptors. The former is divided into D1 and D5 receptors, while the D2 receptor family consists of D2, D3, and D4 receptors.

All major therapies for PD restore the DA tonus which is lost due to the progressive mesencephalic DA-ergic neurodegeneration. L-DOPA is a cheap and efficacious drug, but with a poor PK profile leading to dyskinesia and other response fluctuations. Selective $D_2$-agonists (e.g. pramipexole) give less dyskinesia, and are the preferred first-line treatment of PD.

Certain hydroxylated(phenols or catechols)phenylethylamines (as such or forming part of a semi rigid/rigid ring system) are known to possess useful dopaminergic activity at least in animal models. However, their clinical use is limited because they have low or no oral bioavailability. Apomorphine is used clinically [for clinical experiences, see for example: Manson et al., Brain 124, 331 (2001) and Neef and van Laar, Clin. Pharmacokinet., 37, 257 (1999)]. Several clinical studies are ongoing with alternative delivery strategies for apomorphine, e.g. using intranasal and sublingual formulations; however, these efforts have not yet resulted in an option for the clinical treatment of PD [for general discussions, see: Stacy and Factor (Eds) Neurology, 62 (Supplement 4), S1 (2004) and Neef and van Laar, Clin. Pharmacokinet., 37, 257 (1999)].

DA receptor agonists are able to activate the DA autoreceptors as well as the postsynaptic DA receptors. The effects of autoreceptor stimulation appear to predominate when, for example, apomorphine is administered at low doses, whereas at higher doses the attenuation of DA transmission is outweighed by the enhancement of postsynaptic receptor stimulation. The antipsychotic and antidyskinetic effects in humans of low doses of, for example, apomorphine are likely due to the autoreceptor-stimulator properties of this DA receptor agonist. This body of knowledge indicates that DA receptor stimulants with a high selectivity for central nervous DA autoreceptors would be valuable in treating psychiatric disorders.

Diseases in which an increase in dopaminergic turnover may be beneficial include geriatric diseases as well as bradykinesia. DA receptor stimulants can have an effect in depressed patients, and can be used in the treatment of obesities as an anorectic agent. DA receptor stimulants can improve minimal brain dysfunction (MBD), narcolepsy, and negative and cognitive symptoms of schizophrenia. Restless leg syndrome and periodic limb movement disorder are other indications which are clinically treated with DA-agonists [for a discussion, see: Lesage and Hening, Seminars in Neurology, 24, 249 (2004)]. In addition, impotence and erectile dysfunction are also likely to be improved by treatment with a DA-agonist (in both women and men). In this context, it is noteworthy that apomorphine when given sublingually is used clinically to improve erectile dysfunction in men.

Clinical studies of therapies using L-DOPA and the D2 agonist Pramipexole in Huntington's disease [a neurodegenerative disorder caused by an expanded trinucleotide repeat (CAG) located at the 5' end of the 1T15 gene] have shown promising results; thus, treatment of Huntington's disease is another potential application of the compounds of the invention. Other neurodegenerative disorders caused by an expanded CAG trinucleotide repeat may also be treatable by the compounds of the invention.

DA is involved in regulation of the cardiovascular and renal systems, and accordingly, renal failure and hypertension can be considered further indications for the compounds of the invention.

Furthermore, DA receptor agonists are used in the treatment of hyperprolactinemia to lower the amount of prolactin in the blood [For a recent review see: Chanson, P. et al, Annales d'Endocrinologie 68(2-3), 113 (2007)]. One example of such a DA receptor agonist is the selective D2 agonist quinagolide (Norprolac®). Therefore, hyperprolactinemia can also be considered as an additional indication for the compounds of the invention.

SUMMARY OF THE INVENTION

It is an object of the present invention to provide new phenolic or catecholic amines that can be used as drugs in their own right, or their corresponding alkoxy, acyloxy and methylenedioxy derivatives that are metabolized in vivo to the free catecholic or phenolic amines that are dopamine receptor ligands.

Accordingly, in one aspect the present invention relates to compounds of Formula I:

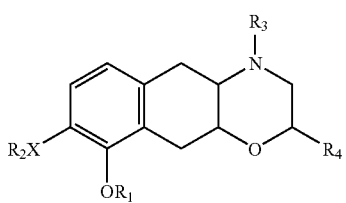

I wherein

X is absent or oxygen when X is oxygen, $R_1$ and $R_2$ are independently selected from hydrogen; $C_1$-$C_6$ alkanoyl; $C_6$-$C_{10}$ aryl-$C_1$-$C_6$ alkanoyl such as phenylacetyl or benzoyl; or $R_1$ and $R_2$ are fused and form a methylene ($CH_2$) group.

when X is absent, $R_1$ is selected from hydrogen; $C_1$-$C_6$ alkyl, $C_1$-$C_6$ alkanoyl; $C_6$-$C_{10}$ aryl-$C_1$-$C_6$ alkanoyl such as phenylacetyl or benzoyl; and $R_2$ is hydrogen.

$R_3$ is selected from the group consisting of hydrogen; $C_1$-$C_4$ alkyl such as methyl, ethyl, n-propyl, cyclo-propyl-methyl, allyl, or propargyl; $C_3$-$C_4$ cycloalkyl such as cyclo-propyl and cyclo-butyl; hydroxyalkyl such as hydroxyethyl; $C_2$-$C_3$ fluoroalkyl such as 3-fluoro-n-propyl and 2-fluoroethyl, $R_4$ is selected from the group consisting of hydrogen; $C_1$-$C_6$ alkyl such as methyl; $C_6$-$C_{10}$ aryl-$C_1$-$C_6$ alkyl such as benzyl; heteroaryl-$C_1$-$C_6$ alkyl such as 1-imidazolyl-methyl; di($C_1$-$C_6$ alkyl)amino-$C_1$-$C_6$ alkyl such as dimethylaminomethyl; $C_1$-$C_6$ alkylthio-$C_1$-$C_6$ alkyl such as methylthiomethyl; $C_1$-$C_6$ hydroxyalkyl such as hydroxymethyl; and $C_1$-$C_6$ haloalkyl such as fluoromethyl, wherein each $C_6$-$C_{10}$ aryl and heteroaryl may be substituted with a substituent selected from halogen such as fluorine, bromine or chlorine; $C_1$-$C_6$ alkyl such as methyl; $C_1$-$C_6$ alkoxy such as methoxy; or phenyl, and enantiomers, diastereomers, tautomers and pharmaceutically acceptable addition salts thereof, and polymorphic forms thereof.

In a particular embodiment, the invention relates to compounds of Formula I in the form of a substantially pure single enantiomer or single diastereomer.

In another particular embodiment, the invention relates to compounds of Formula I in the form of a mixture of enantiomers, a mixture of diastereomers, or a substantially pure polymorph.

In a particular embodiment, the invention relates to compounds of Formula I which have trans-fused ring systems.

In another embodiment of the invention $R_1$ and $R_2$ are both hydrogen and X, $R_3$ and $R_4$ are as defined above.

In another embodiment of the invention $R_1$ and $R_2$ are fused and form a methylene ($CH_2$) group, and X, $R_3$ and $R_4$ are as defined above.

In another embodiment of the invention at least one of $R_1$ and $R_2$ is $C_1$-$C_6$ alkanoyl, phenylacetyl or benzoyl, and X, $R_3$ and $R_4$ are as defined above.

In another embodiment of the invention $R_1$ is hydrogen and X, $R_2$, $R_3$ and $R_4$ are as defined above.

In another embodiment of the invention $R_1$ is $C_1$-$C_6$ alkanoyl, phenylacetyl or benzoyl, and X, $R_2$, $R_3$ and $R_4$ are as defined above.

In a separate embodiment of the invention $R_4$ is hydrogen, and X, $R_1$, $R_2$, $R_3$ are as defined above.

In a separate embodiment of the invention $R_4$ is not hydrogen, and X, $R_1$, $R_2$, $R_3$ are as defined above.

In a separate embodiment of the invention $R_3$ is $C_1$-$C_4$ alkyl, such as methyl, ethyl or n-propyl, and X, $R_1$, $R_2$ and $R_4$ are as defined above.

In a separate embodiment of the invention X is oxygen, and $R_1$, $R_2$, $R_3$ and $R_4$ are as defined above.

In another embodiment of the invention X is absent, and $R_1$, $R_2$, $R_3$ and $R_4$ are as defined above.

In a separate embodiment of the invention $R_4$ is heteroaryl-$C_1$-$C_6$ alkyl wherein the heteroaryl group is pyrazol or substituted pyrazole. In a further embodiment of the invention $R_4$ is heteroaryl-$C_1$-$C_6$ alkyl wherein the heteroaryl group is imidazol. In another embodiment of the invention $R_4$ is heteroaryl-$C_1$-$C_6$ alkyl wherein the heteroaryl group is 1,2,4-triazol.

In a separate embodiment of the invention, the compound of Formula I is in the form of a substantially pure enantiomer. In another embodiment the compound of Formula I is in the form of a substantially pure diastereomer.

In a separate embodiment of the invention $R_4$ is hydrogen, and the compound of Formula I is in the form of the substantially pure (4aR,10aR)-enantiomer.

In a separate embodiment of the invention $R_4$ is hydrogen, and the compound of Formula I is in the form of the substantially pure (4aS,10aS)-enantiomer.

In a separate embodiment of the invention $R_4$ is not hydrogen, and the compound of Formula I is in the form of the substantially pure (2R,4aR,10aR)-enantiomer.

In a separate embodiment of the invention $R_4$ is not hydrogen, and the compound of Formula I is in the form of the substantially pure (2S,4aR,10aR)-enantiomer.

In a separate embodiment of the invention $R_4$ is not hydrogen, and the compound of Formula I is in the form of the substantially pure (2R,4aS,10aS)-enantiomer.

In a separate embodiment of the invention $R_4$ is not hydrogen, and the compound of Formula I is in the form of the substantially pure (2S4aS,10aS)-enantiomer.

In a separate embodiment of the invention $R_4$ is hydrogen, $R_1$ and $R_2$ are fused and form a methylene ($CH_2$) group, and the compound of Formula I is in the form of the substantially pure (6aR,10aR)-enantiomer.

In a separate embodiment of the invention $R_4$ is hydrogen, $R_1$ and $R_2$ are fused and form a methylene ($CH_2$) group, and the compound of Formula I is in the form of the substantially pure (6aS,10aS)-enantiomer.

In a separate embodiment of the invention $R_4$ is not hydrogen, $R_1$ and $R_2$ are fused and form a methylene ($CH_2$) group, and the compound of Formula I is in the form of the substantially pure (2R,6aR,10aR)-enantiomer.

In a separate embodiment of the invention $R_4$ is not hydrogen, $R_1$ and $R_2$ are fused and form a methylene ($CH_2$) group, and the compound of Formula I is in the form of the substantially pure (2R,6aS,10aS)-enantiomer.

In a separate embodiment of the invention $R_4$ is not hydrogen, $R_1$ and $R_2$ are fused and form a methylene ($CH_2$) group, and the compound of Formula I is in the form of the substantially pure (2S,6aR,10aR)-enantiomer.

In a separate embodiment of the invention $R_4$ is not hydrogen, $R_1$ and $R_2$ are fused and form a methylene ($CH_2$) group, and the compound of Formula I is in the form of the substantially pure (2S,6aS,10aS)-enantiomer.

In further embodiments of the invention, the compound of Formula I is selected among the following specific compounds, either as the free base, tautomers thereof or as a pharmaceutically acceptable acid addition salt thereof Each of the compounds constitutes an individual embodiment of the present invention:

(4aR,10aR)-9-Methoxy-4-methyl-3,4,4a,5,10,10a-hexahydro-2H-naphtho[2,3-b][1,4]oxazine;
(4aS,10aS)-9-Methoxy-4-methyl-3,4,4a,5,10,10a-hexahydro-2H-naphtho[2,3-b][1,4]oxazine;
(4aR,10aR)-4-Ethyl-9-methoxy-3,4,4a,5,10,10a-hexahydro-2H-naphtho[2,3-b][1,4]oxazine;
(4aS,10aS)-4-Ethyl-9-methoxy-3,4,4a,5,10,10a-hexahydro-2H-naphtho[2,3-b][1,4]oxazine;
(4aR,10aR)-9-Methoxy-4-n-propyl-3,4,4a,5,10,10a-hexahydro-2H-naphtho[2,3-b][1,4]oxazine;
(4aS,10aS)-9-Methoxy-4-n-propyl-3,4,4a,5,10,10a-hexahydro-2H-naphtho[2,3-b][1,4]oxazine;
(4aR,10aR)-4-Allyl-9-methoxy-3,4,4a,5,10,10a-hexahydro-2H-naphtho[2,3-b][1,4]oxazine;
(4aS,10aS)-4-Allyl-9-methoxy-3,4,4a,5,10,10a-hexahydro-2H-naphtho[2,3-b][1,4]oxazine;
(4aR,10aR)-4-cyclo-Propylmethyl-9-methoxy-3,4,4a,5,10,10a-hexahydro-2H-naphtho[2,3-b][1,4]oxazine;
(4aS,10aS)-4-cyclo-Propylmethyl-9-methoxy-3,4,4a,5,10,10a-hexahydro-2H-naphtho[2,3-b][1,4]oxazine;
(2S,4aR,10aR)-9-Methoxy-4-n-propyl-2-[1,2,4]triazol-1-ylmethyl-3,4,4a,5,10,10a-hexahydro-2H-naphtho[2,3-b][1,4]oxazine;
(2R,4aR,10aR)-9-Methoxy-4-n-propyl-2-[1,2,4]triazol-1-ylmethyl-3,4,4a,5,10,10a-hexahydro-2H-naphtho[2,3-b][1,4]oxazine;
(2S,4aR,10aR)-9-Methoxy-2-methylsulfanylmethyl-4-n-propyl-3,4,4a,5,10,10a-hexahydro-2H-naphtho[2,3-b][1,4]oxazine;
(2R,4aR,10aR)-9-Methoxy-2-methylsulfanylmethyl-4-n-propyl-3,4,4a,5,10,10a-hexahydro-2H-naphtho[2,3-b][1,4]oxazine;
(2R,4aR,10aR)-2-Imidazol-1-ylmethyl-9-methoxy-4-n-propyl-3,4,4a,5,10,10a-hexahydro-2H-naphtho[2,3-b][1,4]oxazine;
(2R,4aR,10aR)-9-Methoxy-2-methoxymethyl-4-n-propyl-3,4,4a,5,10,10a-hexahydro-2H-naphtho[2,3-b][1,4]oxazine;
((2S,4aR,10aR)-9-Methoxy-4-n-propyl-3,4,4a,5,10,10a-hexahydro-2H-naphtho[2,3-b][1,4]oxazin-2-ylmethyl)-dimethylamine;
(2R,4aR,10aR)-2-Fluoromethyl-9-methoxy-4-n-propyl-3,4,4a,5,10,10a-hexahydro-2H-naphtho[2,3-b][1,4]oxazine;
(2S,4aR,10aR)-9-Methoxy-2-methyl-4-n-propyl-3,4,4a,5,10,10a-hexahydro-2H-naphtho[2,3-b][1,4]oxazine;
(2R,4aR,10aR)-9-Methoxy-4-n-propyl-2-pyrazol-1-ylmethyl-3,4,4a,5,10,10a-hexahydro-2H-naphtho[2,3-b][1,4]oxazine;
(2S,4aS,10aS)-9-Methoxy-4-n-propyl-2-pyrazol-1-ylmethyl-3,4,4a,5,10,10a-hexahydro-2H-naphtho[2,3-b][1,4]oxazine;
(2S,4aR,10aR)-9-Methoxy-4-n-propyl-2-pyrazol-1-ylmethyl-3,4,4a,5,10,10a-hexahydro-2H-naphtho[2,3-b][1,4]oxazine;
(2R,4aS,10aS)-9-Methoxy-4-n-propyl-2-pyrazol-1-ylmethyl-3,4,4a,5,10,10a-hexahydro-2H-naphtho[2,3-b][1,4]oxazine;
(2R,4aR,10aR)-2-(4-Chloro-pyrazol-1-ylmethyl)-9-methoxy-4-n-propyl-3,4,4a,5,10,10a-hexahydro-2H-naphtho[2,3-b][1,4]oxazine;
(2S,4aR,10aR)-2-(4-Chloro-pyrazol-1-ylmethyl)-9-methoxy-4-n-propyl-3,4,4a,5,10,10a-hexahydro-2H-naphtho[2,3-b][1,4]oxazine;
(2R,4aR,10aR)-9-Methoxy-2-(3-phenyl-pyrazol-1-ylmethyl)-4-n-propyl-3,4,4a,5,10,10a-hexahydro-2H-naphtho[2,3-b][1,4]oxazine;
(2S,4aR,10aR)-9-Methoxy-2-(3-phenyl-pyrazol-1-ylmethyl)-4-n-propyl-3,4,4a,5,10,10a-hexahydro-2H-naphtho[2,3-b][1,4]oxazine;
(4aR,10aR)-4-Ethyl-3,4,4a,5,10,10a-hexahydro-2H-naphtho[2,3-b][1,4]oxazin-9-ol;
(4aS,10aS)-4-Ethyl-3,4,4a,5,10,10a-hexahydro-2H-naphtho[2,3-b][1,4]oxazin-9-ol;
(4aR,10aR)-4-Methyl-3,4,4a,5,10,10a-hexahydro-2H-naphtho[2,3-b][1,4]oxazin-9-ol;
(4aS,10aS)-4-Methyl-3,4,4a,5,10,10a-hexahydro-2H-naphtho[2,3-b][1,4]oxazin-9-ol;
(4aR,10aR)-4-n-Propyl-3,4,4a,5,10,10a-hexahydro-2H-naphtho[2,3-b][1,4]oxazin-9-ol;
(4aS,10aS)-4-n-Propyl-3,4,4a,5,10,10a-hexahydro-2H-naphtho[2,3-b][1,4]oxazin-9-ol;
(4aR,10aR)-4-Allyl-3,4,4a,5,10,10a-hexahydro-2H-naphtho[2,3-b][1,4]oxazin-9-ol
(4aS,10aS)-4-Allyl-3,4,4a,5,10,10a-hexahydro-2H-naphtho[2,3-b][1,4]oxazin-9-ol;
(4aR,10aR)-4-cyclo-Propylmethyl-3,4,4a,5,10,10a-hexahydro-2H-naphtho[2,3-b][1,4]oxazin-9-ol;
(4aS,10aS)-4-cyclo-Propylmethyl-3,4,4a,5,10,10a-hexahydro-2H-naphtho[2,3-b][1,4]oxazin-9-ol;
(2R,4aR,10aR)-2-Hydroxymethyl-4-n-propyl-3,4,4a,5,10,10a-hexahydro-2H-naphtho[2,3-b][1,4]oxazin-9-ol;
(2S,4aS,10aS)-2-Hydroxymethyl-4-n-propyl-3,4,4a,5,10,10a-hexahydro-2H-naphtho[2,3-b][1,4]oxazin-9-ol;
(2S,4aR,10aR)-2-Hydroxymethyl-4-n-propyl-3,4,4a,5,10,10a-hexahydro-2H-naphtho[2,3-b][1,4]oxazin-9-ol;
(2R,4aS,10aS)-2-Hydroxymethyl-4-n-propyl-3,4,4a,5,10,10a-hexahydro-2H-naphtho[2,3-b][1,4]oxazin-9-ol;
(2S,4aR,10aR)-4-n-Propyl-2-[1,2,4]triazol-1-ylmethyl-3,4,4a,5,10,10a-hexahydro-2H-naphtho[2,3-b][1,4]oxazin-9-ol;
(2R,4aR,10aR)-4-n-Propyl-2-[1,2,4]triazol-1-ylmethyl-3,4,4a,5,10,10a-hexahydro-2H-naphtho[2,3-b][1,4]oxazin-9-ol;
(2S,4aR,10aR)-2-Methylsulfanylmethyl-4-n-propyl-3,4,4a,5,10,10a-hexahydro-2H-naphtho[2,3-b][1,4]oxazin-9-ol;
(2R,4aR,10aR)-2-Methylsulfanylmethyl-4-n-propyl-3,4,4a,5,10,10a-hexahydro-2H-naphtho[2,3-b][1,4]oxazin-9-ol;
(2S,4aR,10aR)-2-Methyl-4-n-propyl-3,4,4a,5,10,10a-hexahydro-2H-naphtho[2,3-b]oxazin-9-ol;
(2R,4aR,10aR)-2-Imidazol-1-ylmethyl-4-n-propyl-3,4,4a,5,10,10a-hexahydro-2H-naphtho[2,3-b][1,4]oxazin-9-ol;
(2R,4aR,10aR)-2-Methoxymethyl-4-n-propyl-3,4,4a,5,10,10a-hexahydro-2H-naphtho[2,3-b][1,4]oxazin-9-ol;
(2S,4aR,10aR)-2-Dimethylaminomethyl-4-n-propyl-3,4,4a,5,10,10a-hexahydro-2H-naphtho[2,3-b][1,4]oxazin-9-ol;
(2R,4aR,10aR)-2-Fluoromethyl-4-n-propyl-3,4,4a,5,10,10a-hexahydro-2H-naphtho[2,3-b][1,4]oxazin-9-ol;
(2R,4aR,10aR)-4-n-Propyl-2-pyrazol-1-ylmethyl-3,4,4a,5,10,10a-hexahydro-2H-naphtho[2,3-b][1,4]oxazin-9-ol;
(2S,4aS,10aS)-4-n-Propyl-2-pyrazol-1-ylmethyl-3,4,4a,5,10,10a-hexahydro-2H-naphtho[2,3-b][1,4]oxazin-9-ol;
(2S,4aR,10aR)-4-n-Propyl-2-pyrazol-1-ylmethyl-3,4,4a,5,10,10a-hexahydro-2H-naphtho[2,3-b][1,4]oxazin-9-ol;
(2R,4aS,10aS)-4-n-Propyl-2-pyrazol-1-ylmethyl-3,4,4a,5,10,10a-hexahydro-2H-naphtho[2,3-b][1,4]oxazin-9-ol;
(2R,4aR,10aR)-2-(4-Chloro-pyrazol-1-ylmethyl)-4-n-propyl-3,4,4a,5,10,10a-hexahydro-2H-naphtho[2,3-b][1,4]oxazin-9-ol;
(2S,4aR,10aR)-2-(4-Chloro-pyrazol-1-ylmethyl)-4-n-propyl-3,4,4a,5,10,10a-hexahydro-2H-naphtho[2,3-b][1,4]oxazin-9-ol;

(2R,4aR,10aR)-2-(3-Phenyl-pyrazol-1-ylmethyl)-4-n-propyl-3,4,4a,5,10,10a-hexahydro-2H-naphtho[2,3-b][1,4]oxazin-9-ol;
(2S,4aR,10aR)-2-(3-Phenyl-pyrazol-1-ylmethyl)-4-n-propyl-3,4,4a,5,10,10a-hexahydro-2H-naphtho[2,3-b][1,4]oxazin-9-ol;
(4aR,10aR)-4-n-Propyl-3,4,4a,5,10,10a-hexahydro-2H-naphtho[2,3-b][1,4]oxazine-8,9-diol;
(6aR,10aR)-7-Methyl-6a,7,8,9,10a,11-hexahydro-6H-1,3,10-trioxa-7-aza-cyclopenta[a]anthracene;
(6aR,10aR)-7-Ethyl-6a,7,8,9,10a,11-hexahydro-6H-1,3,10-trioxa-7-aza-cyclopenta[a]anthracene; and
(6aR,10aR)-7-n-Propyl-6a,7,8,9,10a,11-hexahydro-6H-1,3,10-trioxa-7-aza-cyclopenta[a]anthracene In a further aspect, the invention provides the use of a compound of Formula I or a pharmaceutically acceptable acid addition salt hereof, as a medicament.

The compound of Formula I, either as the free base, or as a pharmaceutically acceptable acid addition salt, or in the form of a pharmaceutical composition thereof, may be administered in any suitable way e.g. orally, buccally, sublingually, non-orally or parenterally, and the compound may be presented in any suitable form for such administration, e.g. orally in the form of tablets, capsules, powders, syrups, solutions or dispersions, non-orally in the form of eg. transdermal patches or parenterally in the form of dispersions or solutions for injection. In one embodiment, the compound of Formula I is administered in the form of a solid pharmaceutical entity, suitably as a tablet or a capsule.

The compounds of Formula I form pharmaceutically acceptable acid addition salts with a wide variety of organic and inorganic acids. Such salts also constitute aspects of the present invention.

A pharmaceutically acceptable acid addition salt of the compound of Formula I is formed from a pharmaceutically acceptable acid, as is well known in the art. Such salts include the pharmaceutically acceptable salts listed in Journal of Pharmaceutical Science, 66, 2-19 (1977) and are known to the skilled person. Inorganic acids used to form such salts include hydrochloric, hydrobromic, hydriodic, nitric, sulphuric, phosphoric, hypophosphoric, metaphosphoric, pyrophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include the chloride, bromide, iodide, nitrate, acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, isobutyrate, phenylbutyrate, α-hydroxybutyrate, butyne-1,4-dicarboxylate, hexyne-1,4-dicarboxylate, caprate, caprylate, cinnamate, citrate, formate, fumarate, glycollate, heptanoate, hippurate, lactate, malate, maleate, hydroxymaleate, malonate, mandelate, mesylate, nicotinate, isonicotinate, oxalate, phthalate, teraphthalate, propiolate, propionate, phenylpropionate, salicylate, sebacate, succinate, suberate, benzenesulfonate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, p-toluenesulfonate, xylenesulfonate, tartrate, and the like.

Methods for the preparation of solid pharmaceutical compositions are also well known in the art. Tablets may thus be prepared by mixing the active ingredient with ordinary adjuvants, fillers and diluents and subsequently compressing the mixture in a convenient tabletting machine. Examples of adjuvants, fillers and diluents comprise microcrystalline cellulose, corn starch, potato starch, lactose, mannitol, sorbitol talcum, magnesium stearate, gelatine, lactose, gums, and the like. Any other adjuvants or additives such as colourings, aroma, preservatives, etc., may also be used provided that they are compatible with the active ingredients.

In particular, the tablet compositions according to the invention may be prepared by direct compression of a compound of Formula I in admixture with conventional adjuvants or diluents. Alternatively, a wet granulate or a melt granulate of a compound of Formula I, optionally in admixture with conventional adjuvants or diluents may be used for compression of tablets.

Solutions of a compound of Formula I for injections may be prepared by dissolving the active ingredient and possible additives in a part of the solvent for injection, preferably sterile water, adjusting the solution to the desired volume, sterilisation of the solution and filling in suitable ampoules or vials. Any suitable additive conventionally used in the art may be added, such as tonicity agents, preservatives, antioxidants, solubilising agents, etc. Alternatively, the active ingredient, eg. as the free base, may be dissolved in a digestible or non-digestible oil, mixtures hereof or similar, to prepare an intramuscular depot composition capable of releasing the active ingredient over a prolonged period of time.

Pharmaceutical compositions of the compound of Formula I to be used in transdermal applications, such as transdermal patches, may optionally contain permeation activators to facilitate the passage of the active ingredient through the skin.

In a specific embodiment of the invention there is provided a pharmaceutical composition comprising a therapeutically effective amount of a compound of Formula I wherein X=oxygen, $R_1$ and $R_2$ are fused and form a methylene ($CH_2$) group and $R_4$ is as defined above, together with a pharmaceutically acceptable carrier or diluent.

In another embodiment of the invention there is provided a pharmaceutical composition comprising a therapeutically effective amount of a compound of Formula I and a pharmaceutically acceptable carrier or diluent, wherein X=oxygen, $R_1$ and $R_2$ are $C_1$-$C_6$ alkanoyl or aryl-$C_1$-$C_6$ alkanoyl such as phenylacetyl or benzoyl, and $R_4$ is as defined above.

In another embodiment of the invention there is provided a pharmaceutical composition comprising a therapeutically effective amount of a compound of Formula I and a pharmaceutically acceptable carrier or diluent, wherein X=oxygen, $R_1$ and $R_2$ are both hydrogen and $R_4$ is as defined above.

In another embodiment of the invention there is provided a pharmaceutical composition comprising a therapeutically effective amount of a compound of Formula I and a pharmaceutically acceptable carrier or diluent, wherein X is absent, $R_1$ is selected from hydrogen; $C_1$-$C_6$ alkyl, $C_1$-$C_6$ alkanoyl and aryl-$C_1$-$C_6$ alkanoyl such as phenylacetyl or benzoyl; and $R_2$ is hydrogen.

In another specific embodiment of the invention there is provided a pharmaceutical composition comprising a therapeutically effective amount of a compound of Formula I and a pharmaceutically acceptable carrier or diluent, for non-oral administration, such as transdermal, nasal, buccal, intramuscular, parenteral, or subcutaneous administration.

In a specific embodiment of the invention there is provided a pharmaceutical composition comprising a therapeutically effective amount of a compound of Formula I and a pharmaceutically acceptable carrier or diluent, wherein the compound of Formula I is in the form of a substantially pure diastereoisomer or a substantially pure enantiomer.

In a further aspect the invention provides the use of a compound of Formula I or a pharmaceutically acceptable acid addition salt thereof for the manufacture of a medicament for the treatment of neurodegenerative disorders, such as Parkinson's disease and Huntington's disease.

In a further aspect the invention provides the use of a compound of Formula I or a pharmaceutically acceptable acid addition salt thereof for the manufacture of a medicament for the treatment of psychoses, impotence, renal failure, heart failure, hyperprolactinemia or hypertension.

In another aspect the invention provides the use of a compound of Formula I or a pharmaceutically acceptable acid addition salt thereof for the manufacture of a medicament for the treatment of cognitive impairment in a mammal. In a specific embodiment the invention provides the use of a compound of Formula I or a pharmaceutically acceptable acid addition salt thereof for the manufacture of a medicament for the treatment of cognitive impairment associated with a disorder or disease selected from schizophrenia, Parkinson's Disease, dementia such as AIDS dementia, anxiety disorder, age associated memory impairment, depression, Alzheimer's Disease, attention deficit hyperactivity disorder (ADHD) and post-traumatic stress disorder (PTSD).

In a still further aspect the invention provides the use of a compound of Formula I or a pharmaceutically acceptable acid addition salt thereof for the manufacture of a medicament for the treatment of restless legs syndrome (RLS) or periodic limb movement disorder (PLMD).

In a different aspect the invention provides the use of a compound of Formula I or a pharmaceutically acceptable acid addition salt thereof for the manufacture of a medicament for the treatment of movement disorders, poverty of movement, gait disorders or intention tremor in a mammal.

In a further aspect the invention provides the use of a compound of Formula I or a pharmaceutically acceptable acid addition salt thereof for the treatment of neurodegenerative disorders such as Parkinson's disease and Huntington's disease.

In a further aspect the invention provides the use of a compound of Formula I or a pharmaceutically acceptable acid addition salt thereof for the treatment of psychoses, impotence, renal failure, heart failure, hyperprolactinemia or hypertension.

In another aspect the invention provides the use of a compound of Formula I, or a pharmaceutically acceptable acid addition salt thereof, for the treatment of cognitive impairment in a mammal. In a specific embodiment the invention provides the use of a compound of Formula I, or a pharmaceutically acceptable acid addition salt thereof for the treatment of cognitive impairment associated with a disorder or disease selected from schizophrenia, Parkinson's Disease, dementia such as AIDS dementia, anxiety disorder, age associated memory impairment, depression, Alzheimer's Disease, attention deficit hyperactivity disorder (ADHD) and post-traumatic stress disorder (PTSD).

In a still further aspect the invention provides the use of a compound of Formula I, or a pharmaceutically acceptable acid addition salt thereof, for the treatment of restless legs syndrome (RLS) or periodic limb movement disorder (PLMD).

In yet another aspect the invention provides the use of a compound of Formula I, or a pharmaceutically acceptable acid addition salt thereof, for the treatment of movement disorders, poverty of movement, gait disorders or intention tremor in a mammal.

In separate aspects the invention provides the use of a compound of Formula I, or a pharmaceutically acceptable acid addition salt thereof, for the manufacture of medicaments, which are intended for oral administration, or for non-oral administration.

The invention also provides a method of treating a mammal suffering from a neurodegenerative disorder, such as Parkinson's disease and Huntington's disease, comprising administering to the mammal a therapeutically effective amount of a compound of Formula I or a pharmaceutically acceptable acid addition salt thereof.

In another aspect the invention also provides a method of treating a mammal suffering from psychoses, impotence, renal failure, heart failure, hyperprolactinemia or hypertension, comprising administering to the mammal a therapeutically effective amount of a compound of Formula I, or a pharmaceutically acceptable acid addition salt thereof.

In a further aspect the invention provides a method of treating a mammal suffering from a cognitive impairment, comprising administering to the mammal an effective amount of a compound of Formula I or a pharmaceutically acceptable acid addition salt thereof.

The invention also relates to a method of treating a mammal suffering from restless legs syndrome (RLS) or periodic limb movement disorder (PLMD), comprising administering to the mammal a therapeutically effective amount of a compound of Formula I or a pharmaceutically acceptable addition salt thereof.

The invention also relates to a method of treating a mammal suffering from movement disorders, poverty of movement, gait disorders or intention tremor comprising administering to the mammal a therapeutically effective amount of a compound of Formula I or a pharmaceutically acceptable acid addition salt thereof.

In a specific embodiment of the invention the mammal is a human subject

The therapeutically effective amount of a compound of Formula I, calculated as the daily dose of the compound of Formula (I) as the free base, is suitably between 0.01 and 125 mg/day, more suitably between 0.05 and 100 mg/day, e.g. preferably between 0.1 and 50 mg/day.

In a specific embodiment the daily dose of the compound of Formula I is between 1 and 10 mg/day.

In another embodiment the daily dose of the compound of Formula I is less than about 1 mg/day.

In a separate embodiment the daily dose of the compound of Formula I is about 0.1 mg/day.

In a further embodiment the invention provides an oral composition comprising from 0.001 mg to 125 mg of a compound of Formula I.

In a further embodiment the invention provides an oral composition comprising from 0.001 mg to 0.1 mg of a compound of Formula I.

In a further embodiment the invention provides an oral composition comprising from 0.01 mg to 1 mg of a compound of Formula I.

In a further embodiment the invention provides an oral composition comprising from 0.1 mg to 10 mg of a compound of Formula I.

DETAILED DESCRIPTION OF THE INVENTION

Definition of Substitutents

Figure 1:
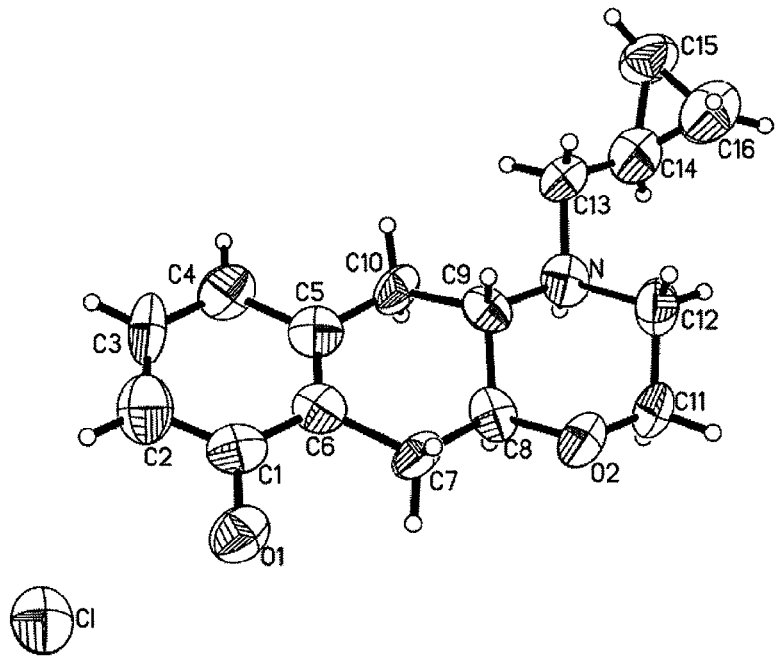
FIG. 1: Crystal structure of (+)-(4aS,10aS)-4-cyclo-propylmethyl-3,4,4a,5,10,10a-hexahydro-2H-naphtho[2,3-b][1,4]oxazin-9-ol hydrochloride (example 5d2). Absolute configuration determined by the anomalous scattering of the 'heavy' chlorine atom.
Figure 2:
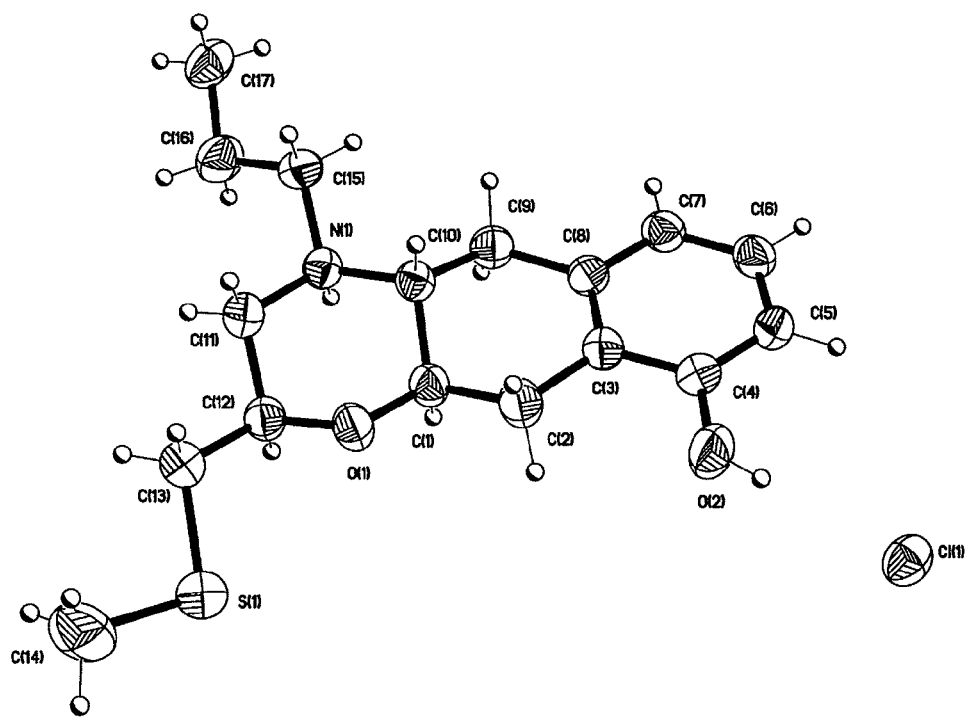
FIG. 2: Crystal structure of (2R,4aR,10aR)-2-methylsulfanylmethyl-4-n-propyl-3,4,4a,5,10,10a-hexahydro-2H-naphtho[2,3-b][1,4]oxazin-9-ol hydrochloride. (example 5j).
Figure 3:
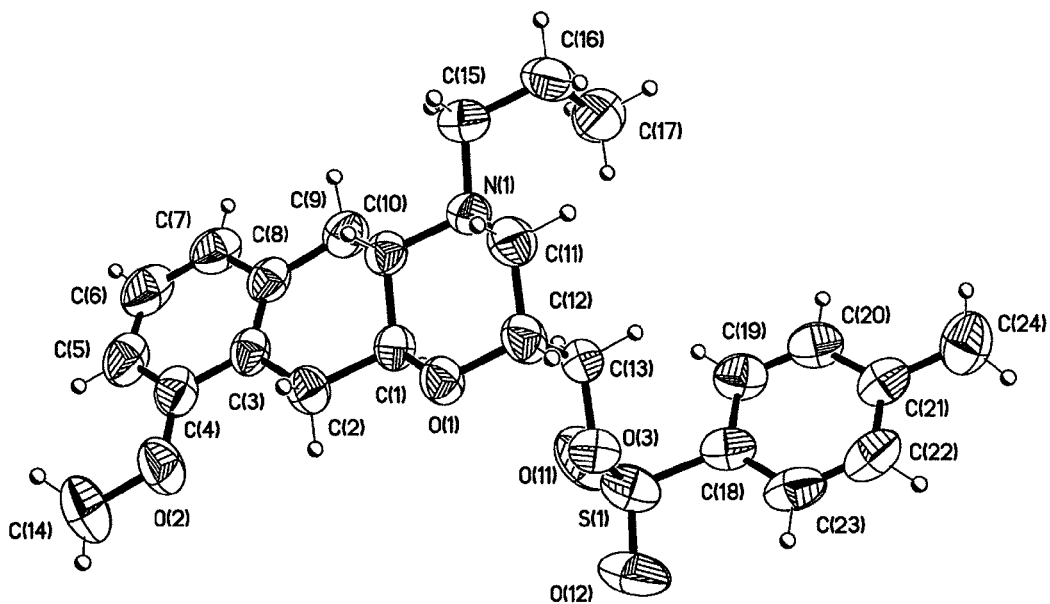
FIG. 3: Crystal structure of toluene-4-sulfonic acid (2R, 4aS,10aS)-9-methoxy-4-propyl-3,4,4a,5,10,10a-hexahydro-2H-naphtho[2,3-b][1,4]oxazin-2-ylmethyl ester (intermediate VB).

As used in the present invention, the term "$C_1$-$C_6$ alkyl" refers to a straight chained or branched saturated hydrocarbon having from one to six carbon atoms inclusive. Examples of such groups include, but are not limited to, methyl, 2-propyl, 1-butyl, 2-butyl, 2-methyl-2-propyl, 2-methyl-1-butyl and n-hexyl.

As used in the present invention, the term "$C_1$-$C_4$ alkyl" refers to a straight chained or branched saturated hydrocarbon having from one to four carbon atoms inclusive. Examples of such groups include, but are not limited to, methyl, ethyl, n-propyl, 2-propyl, 1-butyl and 2-butyl.

The term "$C_1$-$C_6$ alkanoyl" refers to a straight-chain or branched-chain alkanoyl group containing from 1 to six carbon atoms, examples of which include a formyl group, an acetyl group, a pivaloyl group, and the like.

The term "$C_1$-$C_6$ alkoxy" refers to a straight chain or branched saturated alkoxy group having from one to six carbon atoms inclusive with the open valency on the oxygen. Examples of such groups include, but are not limited to, methoxy, ethoxy, n-butoxy, 2-methyl-pentoxy and n-hexyloxy.

The term "$C_1$-$C_6$ alkylthio" refers to a straight chain or branched saturated alkylthio group having from one to six carbon atoms inclusive with the open valency on the sulphur. Examples of such groups include, but are not limited to, methylthio and ethylthio.

The term "$C_6$-$C_{10}$ aryl" refers to a mono- or polycyclic aromatic group, which contains from 6 to 10 ring carbon atoms, and partially saturated variants thereof. Typical examples, which should not be considered limiting, comprise phenyl, indenyl, indanyl, naphthyl and tetrahydronaphthyl.

The term "$C_6$-$C_{10}$ aryl-$C_1$-$C_6$ alkanoyl" refers to a $C_1$-$C_6$ alkanoyl as defined above, which is attached to a $C_6$-$C_{10}$ aryl group as defined above. Typical examples, which should not be considered limiting, comprise benzoyl and phenylacetyl The term "$C_1$-$C_6$-$C_6$-$C_{10}$ aryl" refers to a $C_1$-$C_6$ group as defined above, which is attached to a $C_6$-$C_{10}$ aryl group as defined above.

The term "$C_1$-$C_6$ alkylthio-$C_1$-$C_6$ alkyl" refers to a $C_1$-$C_6$ alkylthio group as defined above, which is attached to a $C_1$-$C_6$ alkyl group as defined above. Examples of such groups include, but are not limited to, methylthiomethyl and ethylthiomethyl.

The term "heteroaryl group" refers to a mono- or polycyclic aromatic group which contains up to 10 ring atoms of which 1 to 4 are selected from N, O or S, and the remaining atoms are carbon, and wherein the ring atoms selected from N, O or S may be placed in one or more rings, and partially saturated variants thereof Typical examples, which should not be considered limiting, comprise pyridyl, thienyl, furyl, indolyl, pyranyl, benzofuranyl, benzothienyl, quinoline, isoquinoline, naphthyridyl, dihydroquinolinyl, chromenyl, thiochromenyl, benzoquinolinyl and acridinyl.

The term "$C_1$-$C_6$ alkyl-heteroaryl" refers to a heteroaryl group as defined above, which is attached to a $C_1$-$C_6$ alkyl group as defined above.

The compounds of the present invention are all trans-fused morpholines, which contains at least two chiral centers (denoted with * below), while the compounds of the present invention with $R_4$ different from H also have a third chiral center (denoted with * below).

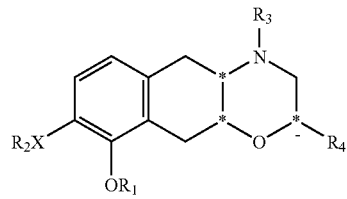

I

When $R_1$ and $R_2$ are not fused, the ring-atoms of the compounds of the invention are numbered as follows:

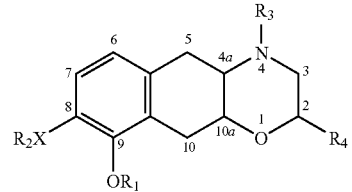

When $R_1$ and $R_2$ are fused to form a methylene group, the ring-atoms of the compounds of the invention are numbered as follows:

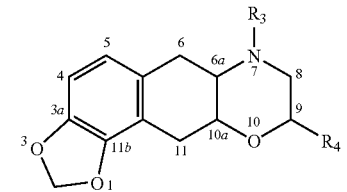

The compounds of the invention can exist in $2^3=8$ different enantiomeric forms, of which only the (R,R) and (S,S) trans-fused morpholine derivatives are comprised by the present invention, i.e.:

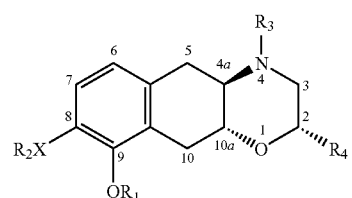

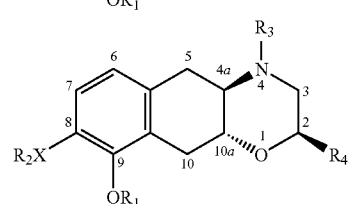

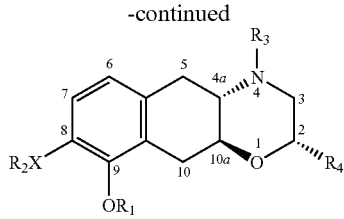

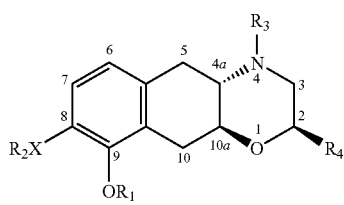

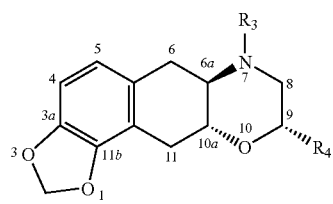

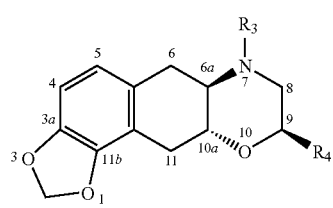

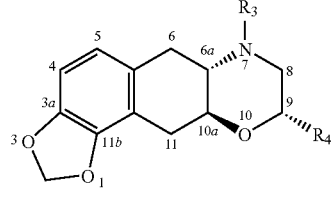

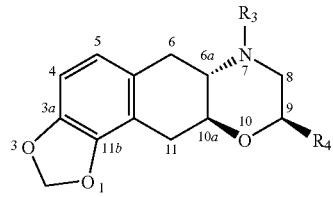

The compounds of Formula I have been found to behave as orally active Apomorphine, which renders them potentially useful in relation to treatment of Parkinson's disease and other diseases/disorders which responds favorably to an increased dopaminergic turnover.

The compounds of Formula I in which X=oxygen have been found to be metabolizable in an in vitro hepatocyte assay to a common catecholamine parent compound for which $R_1$ and $R_2$ are both hydrogen:

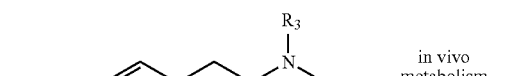

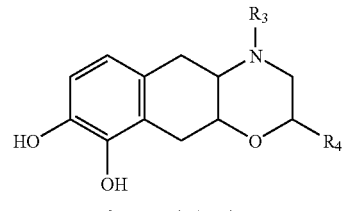

The specific metabolic pathway differs with the substitution pattern, and is not yet completely understood. Thus, for compounds of Formula I wherein X=oxygen and $R_1$ and $R_2$ are ester groups such as $C_1$-$C_6$ alkanoyl and $C_6$-$C_{10}$-aryl-$C_1$-$C_6$ alkanoyl, the metabolism amounts to a hydrolysis of the ester groups. For compounds of Formula I wherein X=oxygen and $R_1$ and $R_2$ are fused and form a methylene ($CH_2$) group, the conversion to the catecholamine occurs through an oxidation of the methylene group, presumably followed by a hydrolytic step.

A specific embodiment of the present invention relates to the use of a compound of Formula I or a pharmaceutically acceptable addition salt thereof for improving cognition in a mammal in a condition of cognitive impairment wherein the condition is associated with schizophrenia. In another embodiment of the invention the condition is associated with Parkinson's Disease. In another embodiment of the invention the condition is associated with dementia, such as AIDS dementia. In another embodiment of the invention the condition is associated with an anxiety disorder. In another embodiment of the invention the condition is associated with age associated memory impairment. In another embodiment of the invention the condition is associated with depression, including major depression, in particular in elderly. In another embodiment of the invention the condition is associated with the use of benzodiazepines. In another embodiment of the invention the condition is associated with the use of tricyclic antidepressants. In another embodiment of the invention the condition is associated with Alzheimer's Disease. In another embodiment of the invention the condition is associated with attention deficit hyperactivity disorder (ADHD). In another embodiment of the invention the condition is associated with post-traumatic stress disorder (PTSD).

In another embodiment, the present invention relates to the use of a compound of Formula I or a pharmaceutically acceptable addition salt thereof for the treatment of a mammal suffering from depression, such as major depression, bipolar disorder or anxiety.

The invention also relates to compounds of Formula I to be used as imaging ligands, in particular PET and SPECT ligands or as precursors therefore. The desired radiolabel can be introduced by reacting precursors of PET or SPECT ligands with radio-labeled reactants, including $^{11}$C-labelled reactants such as [$^{11}$C]methyl iodide, [$^{11}$C]methyl triflate, etc. The compounds may also be labeled with $^3$H, $^{18}$F or $^{123}$I. In a specific embodiment of the invention there is thus provided a radiolabeled compound of Formula I in which the radiolabel is selected from $^{11}C$, $^{3}H$, $^{18}F$ or $^{123}I$.

The radiolabeled compounds of Formula I wherein $R_1$ and $R_2$ are both hydrogen are particularly preferred as radioligands.

In a specific embodiment, the invention relates to a radiolabeled compound of Formula I wherein X=oxygen, $R_1$ and $R_2$ are both hydrogen and $R_3$ is 3-($^{18}F$)-fluoropropyl or 2-($^{18}F$)-fluoroethyl.

In another specific embodiment, the invention relates to a radiolabeled compound of Formula I wherein X is a bond, $R_1$ is hydrogen and $R_3$ is chosen from 3-($^{18}F$)-fluoropropyl, 2-($^{18}F$)-fluoroethyl, ($^{11}CH_3$)—, ($^{11}CH_3CH_2$)— or ($^{11}CH_3CH_2CH_2$)—.

In a preferred embodiment the invention relates to a radiolabeled compound of Formula I wherein X=oxygen, $R_1$ and $R_2$ are both hydrogen, $R_3$ is n-propyl and $R_4$ contains a radiolabel selected from $^{11}C$, $^{3}H$, and $^{18}F$. In one embodiment $R_4$ is chosen from 3-($^{18}F$)-fluoropropyl, 2-($^{18}F$)-fluoroethyl, ($^{11}CH_3$)—, ($^{11}CH_3CH_2$)— or ($^{11}CH_3CH_2CH_2$)—.

Further embodiments relates to the free base of a compound of Formula I or a salt thereof, or a pharmaceutical composition thereof and to the uses as described herein, wherein the compound of Formula I has a trans-diastereomeric excess of at least 10% (10% trans-diastereomeric excess means that the ratio of the trans- to the cis-diastereoisomer is 55:45 in the mixture in question), at least 25%, at least 50%, at least 70%, at least 80%, at least 90%, at least 95%, at least 97%, preferably at least 98%. As used herein, the terminology "cis" and "trans" relates exclusively to the configuration of the two carbons (marked with an * below) joining the morpholine ring with the central ring of the compounds of Formula I:

I

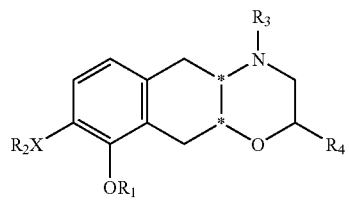

The trans-diastereoisomers of the present invention always have either (R,R) or (S,S) configuration, whereas the cis-diastereoisomers (which are not comprised by the present invention) have either (R,S) or (S,R) configuration.

Further embodiments relate to the free base of a compound of Formula I or a salt thereof, or a pharmaceutical composition thereof and to the uses as described herein, wherein the compound of Formula I has an enantiomeric excess of at least 10% (for example, 10% enantiomeric excess for a compound of Formula I having (4aR,10aR) configuration means that the ratio between the (4aR,10aR)- and (4aS,10aS)-enantiomers is 55:45 in the mixture in question), at least 25%, at least 50%, at least 70%, at least 80%, at least 90%, at least 95%, at least 97%, preferably at least 98%.

In another aspect the present invention relates to compounds of Formula I wherein the catechol moiety is masked as a methylenedioxy (MDO) prodrug derivative, which may be metabolized in vivo to generate the free catecholamines:

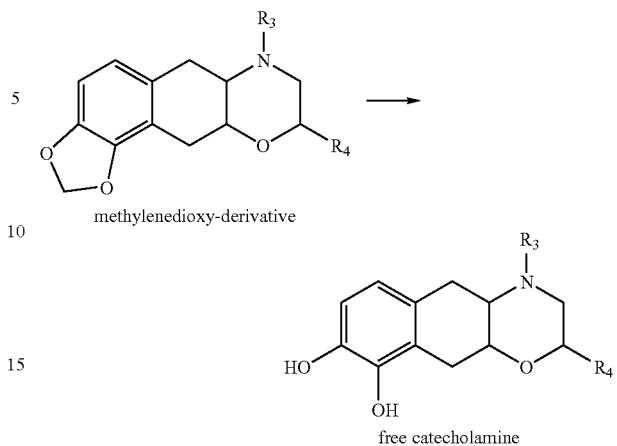

methylenedioxy-derivative free catecholamine

The invention thus also relates to compounds of Formula I wherein X=oxygen and $R_1$ and $R_2$ are fused and form a methylene ($CH_2$) group.

In another aspect the present invention relates to such compounds of Formula I wherein the catechol moiety is masked as a di-ester derivative which may also be cleaved in vivo to generate the free catecholamines (exemplified below for X=oxygen, and $R_1$ and $R_2$=acetyl):

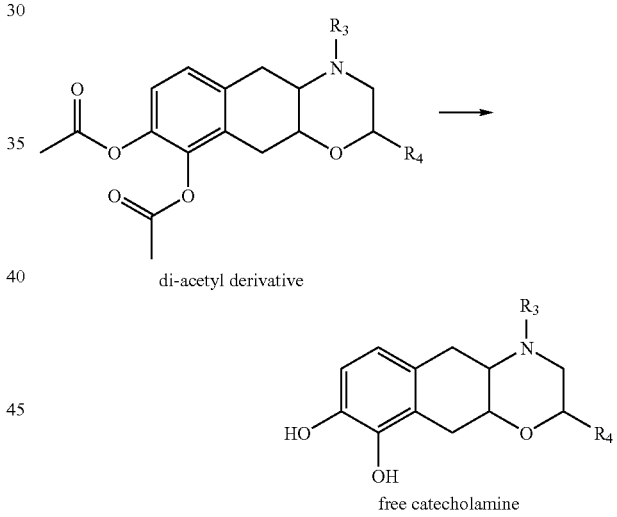

di-acetyl derivative free catecholamine

The present invention further comprises unsymmetrical di-ester derivatives of the compounds of Formula I, wherein $R_1$ and $R_2$ are two different substituents.

The invention furthermore relates to substantially pure trans-diastereoisomers of compounds of Formula I wherein X=oxygen, $R_1$ and $R_2$ are fused and form a methylene ($CH_2$) group, and $R_3$ is selected from the group consisting of hydrogen, methyl, ethyl, and n-propyl.

The invention also relates to substantially pure (6aR,10aR) enantiomers of compounds of Formula I wherein X=oxygen, $R_1$ and $R_2$ are fused and form a methylene ($CH_2$) group, and $R_3$ is selected from the group consisting of hydrogen, methyl, ethyl and n-propyl.

In separate embodiments the invention relates to compounds of Formula I wherein X=oxygen, $R_3$ is selected from the group consisting of hydrogen, methyl, ethyl and n-propyl and at least one of $R_1$ and $R_2$ is $C_1$-$C_6$ alkanoyl, or at least one of $R_1$ and $R_2$ is benzoyl, or at least one of $R_1$ and $R_2$ is phenylacetyl.

The invention furthermore relates to substantially pure trans-diastereoisomers of Formula I wherein X=oxygen, $R_3$ is selected from the group consisting of hydrogen, methyl, ethyl and n-propyl and at least one of $R_1$ and $R_2$ is $C_1$-$C_6$ alkanoyl such as pivaloyl, or at least one of $R_1$ and $R_2$ is benzoyl, or at least one of $R_1$ and $R_2$ is phenylacetyl.

The invention also relates to substantially pure (4aR,10aR) enantiomers of Formula I wherein X=oxygen, $R_3$ is selected from the group consisting of hydrogen, methyl, ethyl and n-propyl and at least one of $R_1$ and $R_2$ is $C_1$-$C_6$ alkanoyl such as pivaloyl, or at least one of $R_1$ and $R_2$ is benzoyl, or at least one of $R_1$ and $R_2$ is phenylacetyl.

In the present context, in particular for the pharmaceutical uses disclosed herein, it is understood that when specifying the compound of Formula (I) to be substantially enantiomerically or diastereomerically pure, then the compound is relatively stereochemically pure. Preferably the enantiomeric or diastereomeric excess is at least 60%, at least 70%, and more preferably at least 80% (80% enantiomeric excess means that the ratio of eg. (4aR,10aR) to (4aS,10aS) is 90:10 in the mixture in question), at least 90%, at least 96%, or preferably at least 98%.

General Synthetic Methods

Scheme 1 depicts the preparation of compounds of this invention, in which X is absent and $R_2$ and $R_4$=H.

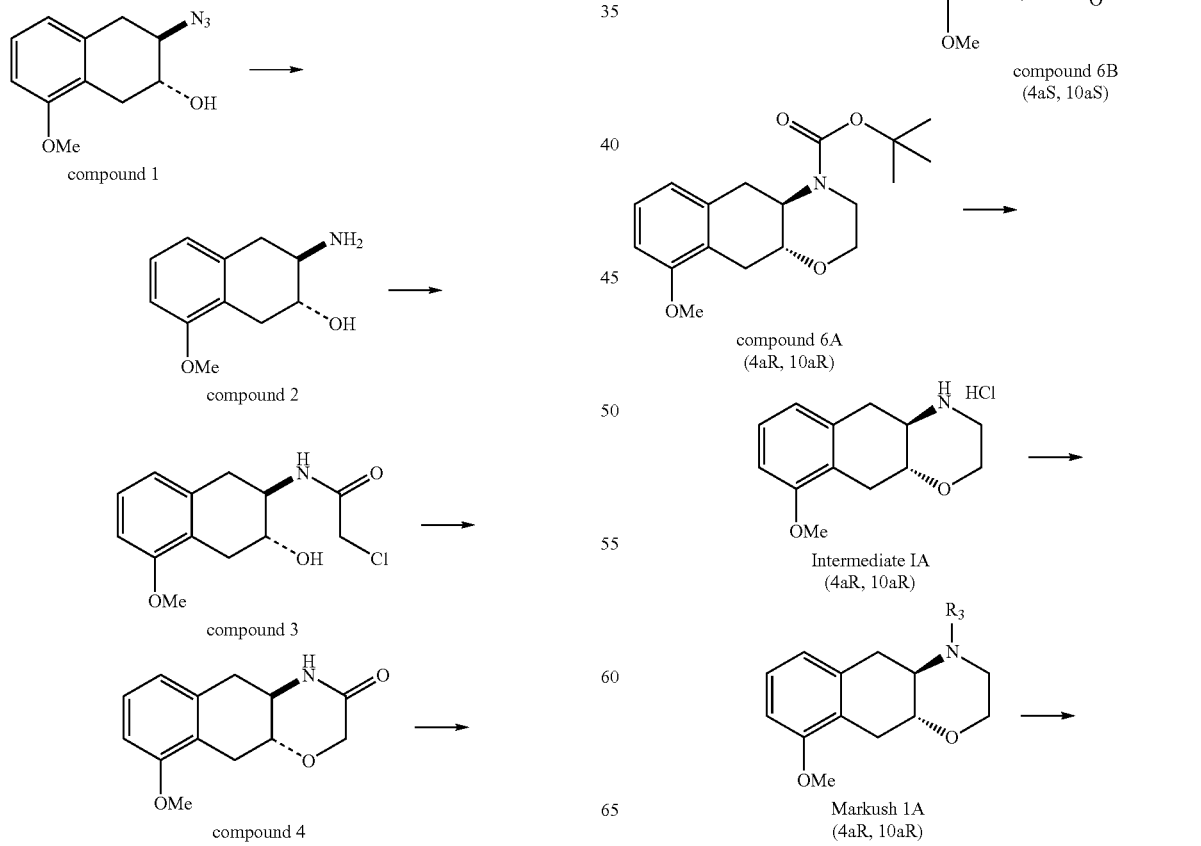

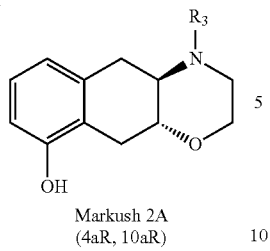

Markush 2A
(4aR, 10aR)

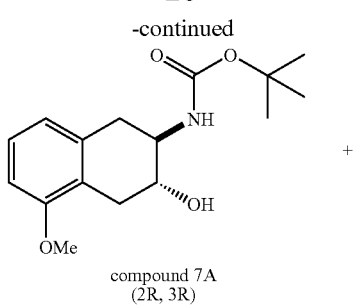

compound 7A
(2R, 3R)

Starting from known racemic trans-3-azido-8-methoxy-1,2,3,4-tetrahydro-naphthalen-2-ol [Nozulak, J.; Vigouret, J. M.; Jaton, A. L.; Hofmann, A.; Dravid, A. R.; Weber, H. P.; Kalkman, H. O.; Walkinshaw, M. D.; *J. Med. Chem.* 1992, 35, 480-489] (compound 1), reduction of the azido-group gives the corresponding trans-amino alcohol, which is acylated with chloro-acetyl chloride. Subsequent ring-closure under basic conditions followed by amide reduction and Boc-protection furnishes key compound 6 as a pure diastereomer. Resolution of compound 6 by chromatography followed by deprotection yields the two enantiomers 6A and 6B.

Preparation of Markush 1A: Starting from compound 6A the compounds of the invention with (4aR,10aR) configuration can be prepared by several methods. Reduction of compound 6A with LAH produces Markush 1A in which $R_3$=$CH_3$. Alternatively, the BOC group can be cleaved with acid. Subsequently, Markush 1A can be prepared for example by N-alkylation using alkyl iodides or alkyl bromides. Another method is acylation of the secondary amine, followed by reduction with e.g. LAH. A third method is reductive amination with aldehydes, ketones, or ketone surrogates such as (1-ethoxy-cyclo-propyl)-oxy]trimethylsilane.

Preparation of Markush 2A: One example of the preparation of Markush 2A constitutes of the cleavage of the methoxy group of Markush 1A. One method of cleaving the methoxy group is by using L-selectride in THF at high temperature. Another method involves treatment with thiophenol and KF in DMA at high temperature.

Starting from compound 6B the compounds of the invention with (4aS,10aS) configuration can be prepared analogously.

Scheme 2 depicts the preparation of the compounds of this invention, for which X is absent and $R_4$ is different from hydrogen.

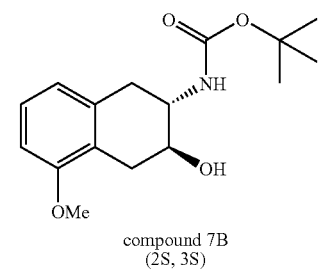

compound 7B
(2S, 3S)

Scheme 2

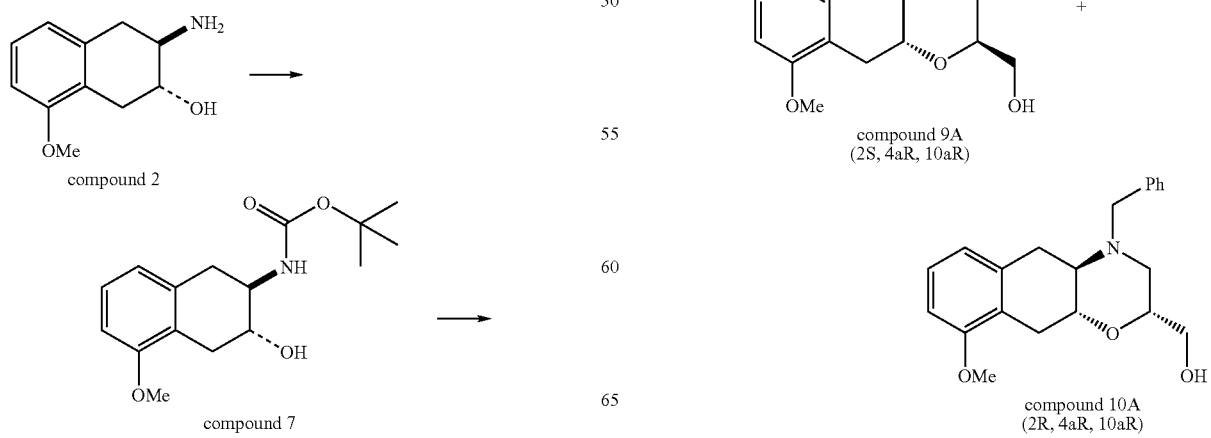

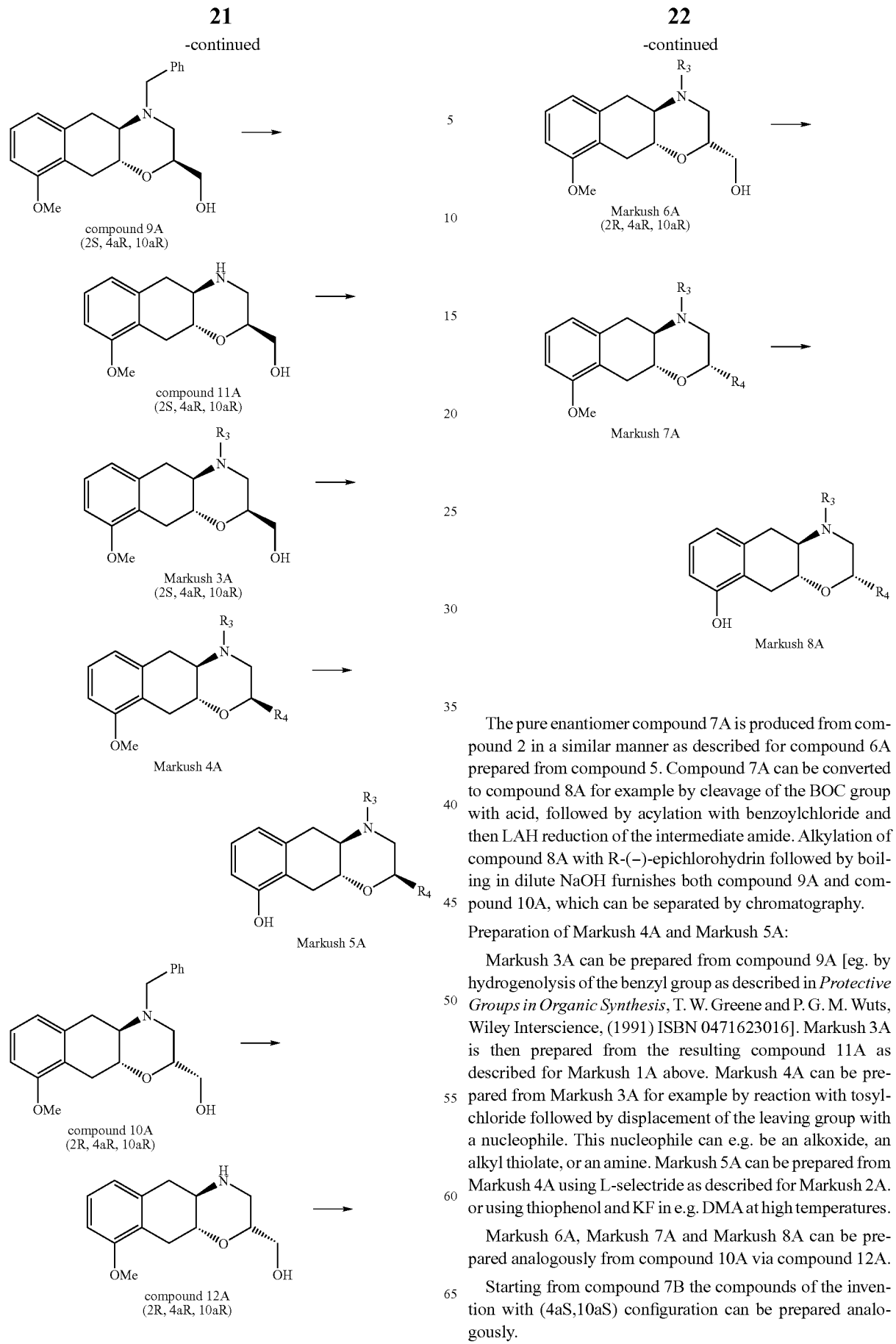

The pure enantiomer compound 7A is produced from compound 2 in a similar manner as described for compound 6A prepared from compound 5. Compound 7A can be converted to compound 8A for example by cleavage of the BOC group with acid, followed by acylation with benzoylchloride and then LAH reduction of the intermediate amide. Alkylation of compound 8A with R-(−)-epichlorohydrin followed by boiling in dilute NaOH furnishes both compound 9A and compound 10A, which can be separated by chromatography.

Preparation of Markush 4A and Markush 5A:

Markush 3A can be prepared from compound 9A [eg. by hydrogenolysis of the benzyl group as described in *Protective Groups in Organic Synthesis*, T. W. Greene and P. G. M. Wuts, Wiley Interscience, (1991) ISBN 0471623016]. Markush 3A is then prepared from the resulting compound 11A as described for Markush 1A above. Markush 4A can be prepared from Markush 3A for example by reaction with tosylchloride followed by displacement of the leaving group with a nucleophile. This nucleophile can e.g. be an alkoxide, an alkyl thiolate, or an amine. Markush 5A can be prepared from Markush 4A using L-selectride as described for Markush 2A. or using thiophenol and KF in e.g. DMA at high temperatures.

Markush 6A, Markush 7A and Markush 8A can be prepared analogously from compound 10A via compound 12A.

Starting from compound 7B the compounds of the invention with (4aS,10aS) configuration can be prepared analogously.

Scheme 3.

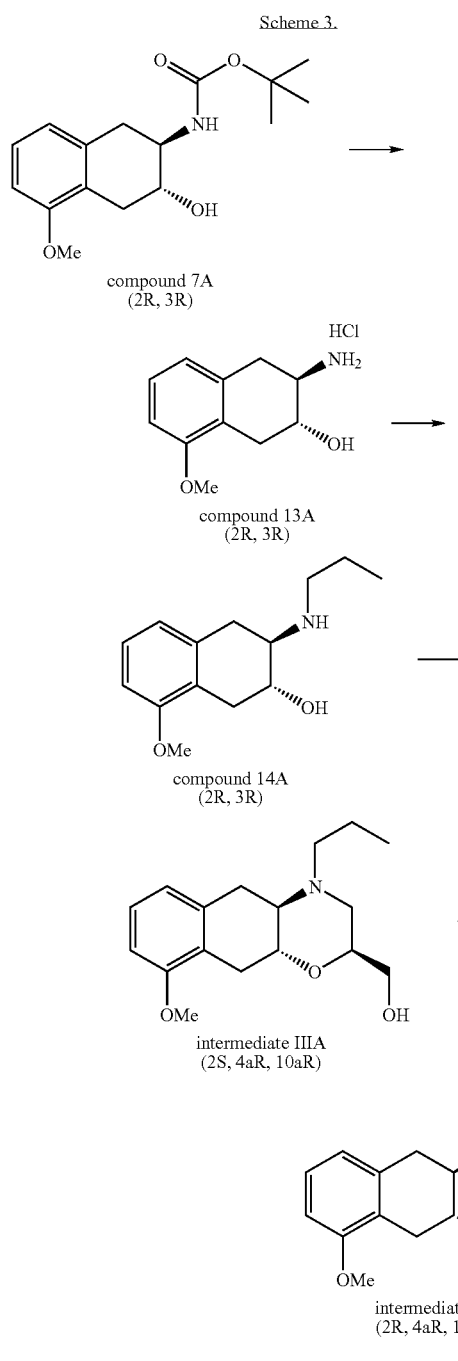

Scheme 4.

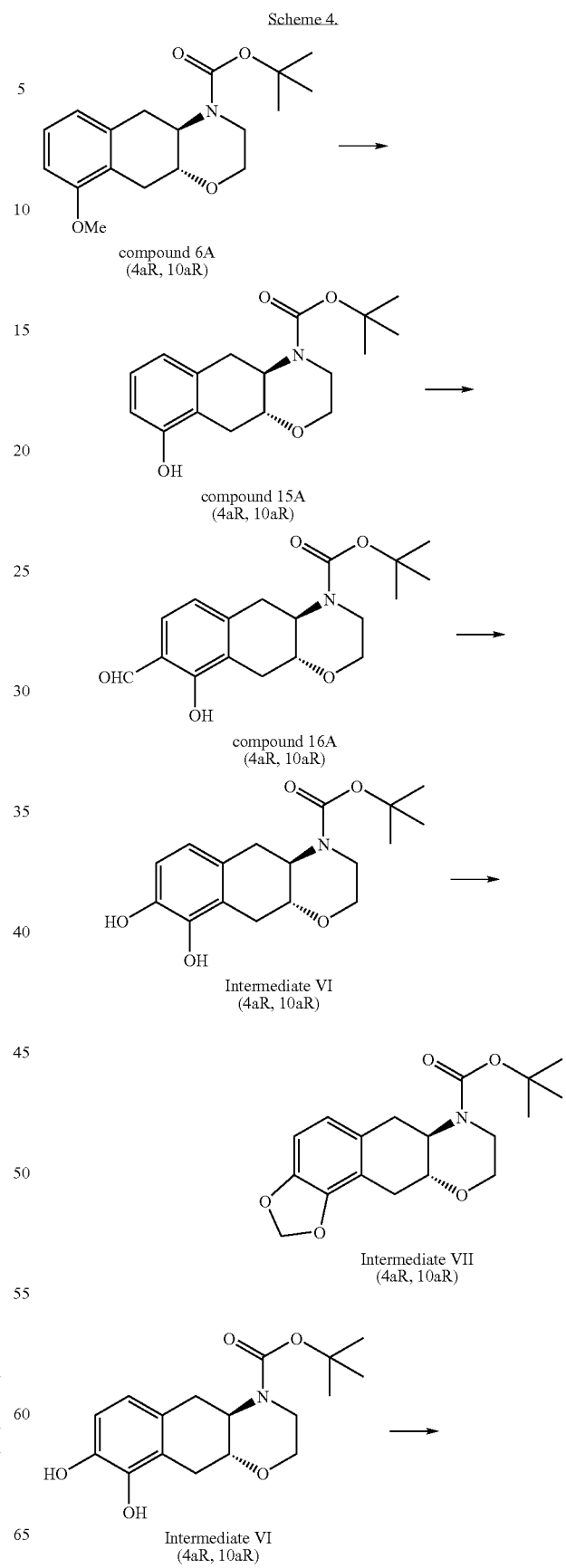

Markush 3A and 6A, in which $R_3$=n-propyl (intermediate IIIA and IIA), can also be prepared from compound 7A as depicted in Scheme 3. Cleavage of the BOC group with acid, followed by acylation with propionylchloride and then LAH reduction of the intermediate amide to produce compound 14A. Alkylation of compound 14A with R-(−)-epichlorohydrin or with S-(+)-epichlorohydrin followed by boiling in dilute NaOH furnishes a mixture of intermediates IIA and IIIA. These two diastereomers can be separated by chromatography.

Starting from compound 7B the compounds of the invention with (4aS,10aS) configuration can be prepared analogously.

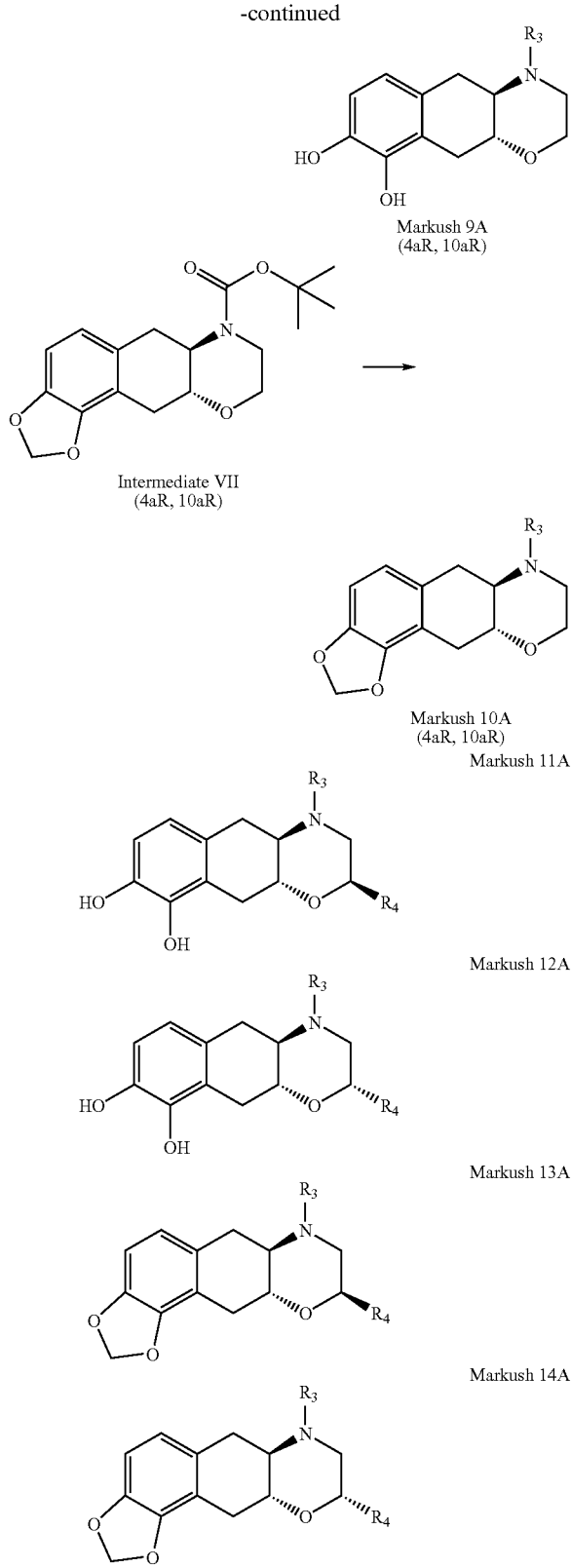

Preparation of Markush 9A and Markush 10A: Starting from compound 6A, Markush 9A and Markush 10A can be prepared for example by cleavage of the methoxy group with L-selectride in THF at high temperature to produce compound 15A. This material can be converted into compound 16A with paraformaldehyde and a Grignard reagent under the proper conditions as described herein. Dakin oxidation furnishes intermediate VI, which can be converted into intermediate VII, e.g. by using bromochloromethane and a base in a suitable solvent. Markush 9A and Markush 10A can then be prepared by the methods described for the preparation Markush 1A from compound 6A.

Markush 11A, 12A, 13A, and 14A can be prepared in a similar manner.

Experimental Section

General Methods

Analytical LC/MS data were obtained on a PE Sciex API 150EX instrument equipped with atmospheric pressure photo ionisation and a Shimadzu LC-8A/SLC-10A LC system. Purity was determined by integration of the UV (254 nm) and ELSD trace. MS instruments are from PESciex (API), equipped with APPI-source and operated in positive ion mode. The retention times in the UV-trace (RT) are expressed in min. Solvents A was made of 0.05% TFA in water, while solvent B was made of 0.035% TFA and 5% water in acetonitrile. Several different methods have been used:

Method 25: API 150EX and Shimadzu LC10AD/SLC-10A LC system. Column: dC-18 4.6×30 mm, 3 μm (Atlantis, Waters). Column temperature: 40° C. Gradient: reverse phase with ion pairing. Flow: 3.3 mL/min. injection volume: 15 micro-L. Gradient: 2% B in A to 100% B over 2.4 min then 2% B in A for 0.4 min. Total run time: 2.8 min.

Method 101: API 150EX and Shimadzu LC8/SLC-10A LC system. Column: C-18 4.6×30 mm, 3.5 μm (Symmetry, Waters). Column temperature: 60° C. Gradient, reverse phase with ion pairing. Flow: 3.3 mL/min. Injection volume: 15 micro-L. Gradient: 10% B in A to 100% B over 2.4 min then 10% B in A for 0.4 min. Total run time: 2.8 min.

Method 102: API 150EX and Shimadzu LC8/SLC-10A LC system. Column: dC-18 4.6×30 mm, 3 μm (Atlantis, Waters). Column temperature: 40° C. Gradient, reverse phase with ion pairing. Flow: 3.3 mL/min. Injection volume: 15 micro-L. Gradient: 2% B in A to 100% B over 2.4 min then 2% B in A for 0.4 min. Total run time: 2.8 min.

Method 111: API 150EX and Shimadzu LC8/SLC-10A LC system. Column: C-18 4.6×30 mm, 3.5 μm (Symmetry, Waters). Column temperature: 60° C. Gradient, reverse phase with ion pairing. Flow: 3.3 mL/min. Injection volume: 10 micro-L (1 micro-L injected onto the column). Gradient: 10% B in A to 100% B over 2.4 min then 10% B in A for 0.4 min. Total run time: 2.8 min.

Method 350: API 300 and waters UPLC system. Column: Acquity UPLC BEH C-18 2.1×50 mm, 1.7 μm (Waters). Column Temperature: 60° C. Flow 1.2 mL/min. Injection volume: 1 micro-L. Gradient: 10% B in A over to 100% B over 1 min. Then 10% B for A in 0.15 min. Total run time: 1.15 min.

Hydrogenation reactions were performed using a standard Parr shaker (1-3 bar hydrogen pressure).

Unless stated specifically, the term "chromatography" refers to HPLC, "silica gel chromatography", or to "chiral SFC".

"Chiral SFC" was performed on a Berger SFC multigram II instrument equipped with a chiral column typically using a mixture of supercritical $CO_2$ and various modifiers as the eluent.

Preparative HPLC-purification was performed on the same instrument with atmospheric pressure chemical ionisation. Column: 50×20 mm YMC ODS-A with 5-μm particle size. Method: linear gradient elution with 80% A to 100% B in 7 min and with a flow rate of 22.7 mL/min. Fraction collection was performed by split-flow MS detection.

The term "silica gel chromatography (EtOAc/heptane)" has the following meaning: The compound to be purified was usually dissolved in a small amount of DCM and loaded onto a column pre-packed with silica gel and eluted using a mixture of EtOAc and heptane, either in a isocratic fashion or with a gradient such as 0-100% of EtOAc in heptane. One example of a column loaded with silica gel used is "ISOLUTE SPE COLUMNS" [e.g. 20 g FLASH Si 70 mL from International sorbent technology]. Alternatively, classical manual chromatographic purifications were performed using silica gel [e.g. Machery-Nagel 60 M; 0.04-0.063 mm, 230-400 mesh] with compound identification by standard TLC analysis performed on aluminium plates precoated with silica gel [e.g. Merck 60 $F_{254}$]. Compounds were visualized by illumination using a UV lamp (254 nm) or by charring after dipping in a solution of ammonium molybdate (6.25 g) and cerium(IV)sulfate (2.5 g) in 10% aqueous sulphuric acid (250 mL).

Microwave-accelerated reactions were performed in sealed microwave reactor vials. The experiments were performed on a Smith Synthesizer from Personal Chemistry.

The term "lyophilized" refers to the freeze-drying of a material using a Christ Alpha 2-4 LSC instrument from WWR International.

The terms "dried ($Na_2SO_4$)" and "dried ($Mg_2SO_4$)" refers to the removal of water from organic layers by the addition of dry $Na_2SO_4$ or $Mg_2SO_4$, respectively, followed by stirring for an appropriate amount of time to ensure an effective drying process. Then the solid is removed by filtration, and the filtrate is typically concentrated in vacuo (see below).

The term "concentrated in vacuo" has the following meaning: The volatile components were removed from the mixture using a standard rotary evaporator at reduced pressure. The term "dried in vacuo at 40° C." refers to the use of a standard vacuum oven heated to 40° C. connected to an oil pump. The term "dried in vacuo" refers to a drying process in which the material to be dried is placed in a flask connected directly to an oil pump for a sufficient period of time to remove volatile components.

X-ray crystal structure determinations were performed as follows. The crystal of the compounds was cooled to 120 K using a Cryostream nitrogen gas cooler system. The data were collected on a Siemens SMART Platform diffractometer with a CCD area sensitive detector. The structures were solved by direct methods and refined by full-matrix least-squares against $F^2$ of all data. The hydrogen atoms in the structures could be found in the electron density difference maps. The non-hydrogen atoms were refined anisotropically. All the hydrogen atoms were at calculated positions using a riding model with O—H=0.84, C—H=0.99-1.00, N—H=0.92-0.93 Å. For all hydrogen atoms the thermal parameters were fixed [U(H)=1.2 U for attached atom]. The Flack x-parameters are in the range 0.0(1)-0.05(1), indicating that the absolute structures are correct. Programs used for data collection, data reduction and absorption were SMART, SAINT and SADABS [cf. "*SMART and SAINT, Area Detector Control and Integration Software*", Version 5.054, Bruker Analytical X-Ray Instruments Inc., Madison, USA (1998), Sheldrick "*SADABS, Program for Empirical Correction of Area Detector Data*" Version 2.03, University of Göttingen, Germany (2001)]. The program SHELXTL [cf. Sheldrick "*SHELXTL, Structure Determination Programs*", Version 6.12, Bruker Analytical X-Ray Instruments Inc., Madison, USA (2001)] was used to solve the structures and for molecular graphics.

Preparation of the Intermediates of the Invention

The following intermediates, which constitute further aspects of the invention, are useful for the preparation of the compounds of the invention:

Intermediates I-VII.

intermediate IA

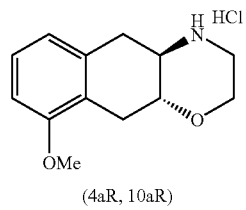

(4aR, 10aR)

intermediate IB

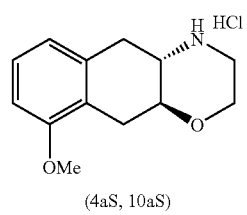

(4aS, 10aS)

intermediate IIA

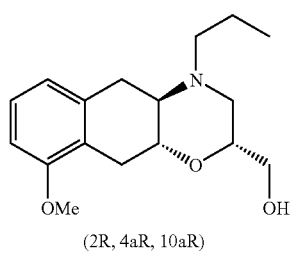

(2R, 4aR, 10aR)

intermediate IIB

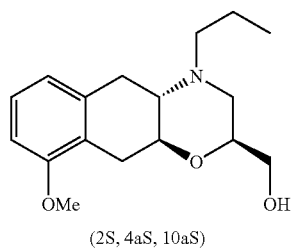

(2S, 4aS, 10aS)

intermediate IIIA

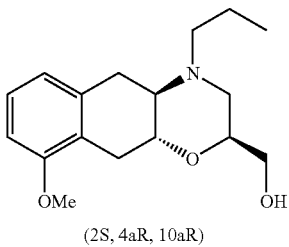

(2S, 4aR, 10aR)

intermediate IIIB

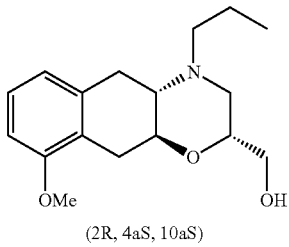

(2R, 4aS, 10aS)

-continued

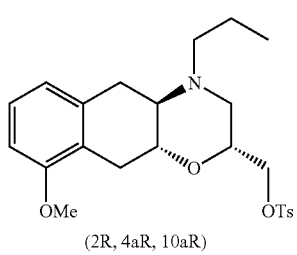
(2R, 4aR, 10aR)

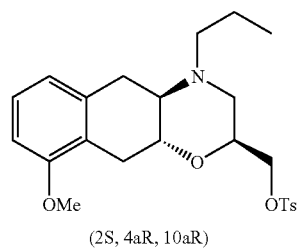
(2S, 4aR, 10aR)

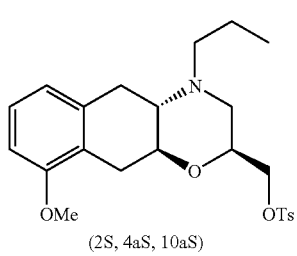
(2S, 4aS, 10aS)

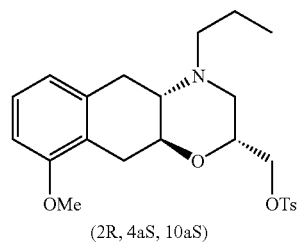
(2R, 4aS, 10aS)

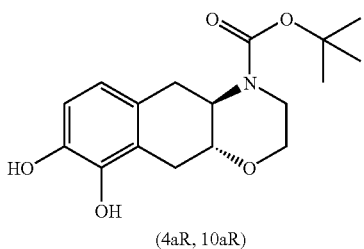
(4aR, 10aR)

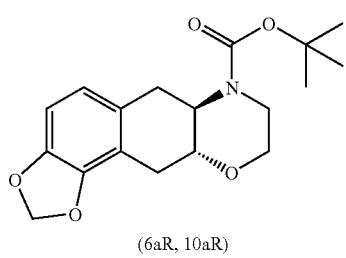
(6aR, 10aR)

intermediate IVA intermediate VA intermediate IVB intermediate VB intermediate VI intermediate VII Preparation of Intermediates IA and IB

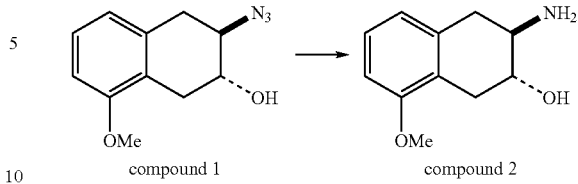

compound 1 → compound 2

Racemic trans-3-amino-8-methoxy-1,2,3,4-tetrahydro-naphthalen-2-ol (Compound 2)

Compound 1 (6.17 g; prepared as described by Nozulak et al [Nozulak, J.; Vigouret, J. M.; Jaton, A. L.; Hofmann, A.; Dravid, A. R.; Weber, H. P.; Kalkman, H. O.; Walkinshaw, M. D. *J. Med. Chem.* 1992, 35, 480-489]) was dissolved in 99% EtOH (280 mL) and 10% Pd/C (617 mg) was added under an argon atmosphere. The mixture was hydrogenated at rt at 2.5 bar of $H_2$ pressure for 3 h. The crude mixture was filtered through Celite, concentrated, and dried in vacuo to give compound 2 as a white solid. Yield: 5.24 g.

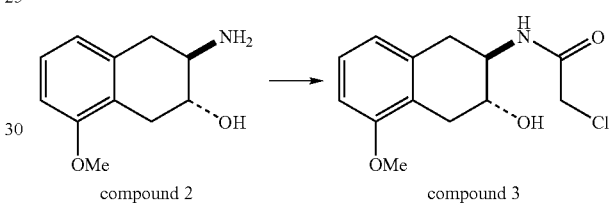

compound 2 → compound 3

Racemic trans-2-chloro-N-3-hydroxy-5-methoxy-1,2,3,4-tetrahydro-naphthalen-2-yl)-acetamide (Compound 3)

At 0° C. ClAcCl (2.90 mL) in THF (14 mL) was added over 2-3 min to a stirred solution of compound 2 (5.22 g) in THF (260 mL) and $Et_3N$ (6.30 mL). The mixture was stirred for 2 h at rt. EtOAc (500 mL) and 1 M HCl (500 mL) were added and the organic layer was extracted with water (500 mL). The combined aqueous layers were extracted with EtOAc (500 mL). The combined organic layers were washed with brine (500 mL), dried ($MgSO_4$), filtered, and concentrated in vacuo to give 7.57 g of compound 3 as a pale yellow solid.

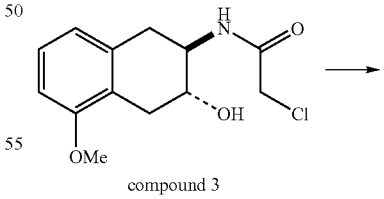

compound 3

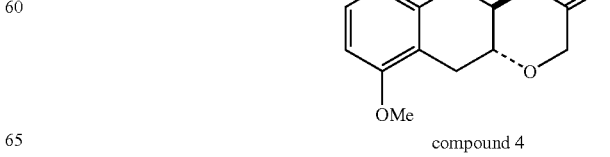

compound 4

Racemic trans-9-methoxy-4a,5,10,10a-hexahydro-4H-naphtho[2,3-b][1,4]oxazine-3-one. (Compound 4)

60% NaH dispersion (1.29 g) and TBAI (1.05 g) were suspended in THF (46 mL) [forming a hard solid, which was chopped into small pieces]. Compound 3 (7.57 g) in THF (300 mL) was added drop-wise over 20 min. The mixture was stirred overnight at rt. The solution was subsequently concentrated in vacuo, and the residue was dissolved in DCM and washed with ice-cold water. The organic layer was washed with 1 M HCl, washed with brine, dried (MgSO₄), and concentrated in vacuo to give 2.83 g of compound 4 as a colorless solid after silica gel chromatography (EtOAc).

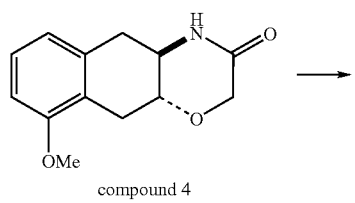

compound 4

Racemic trans-9-methoxy-3,4,4a,5,10,10a-hexahydro-2H-naphtho[2,3-b][1,4]oxazine (Compound 5)

1 M LAH in THF (15 mL) was added drop-wise to a stirred mixture of compound 4 (1.61 g) in THF (83 mL). The mixture was stirred for 3 h at rt. The solution was quenched with ice-cold water and Et₂O was added. The aqueous layer was extracted with Et₂O. The combined organic layers were washed with brine, dried (MgSO₄), filtered, and concentrated in vacuo to give compound 5 as a yellow oil. This material was used directly in the next step.

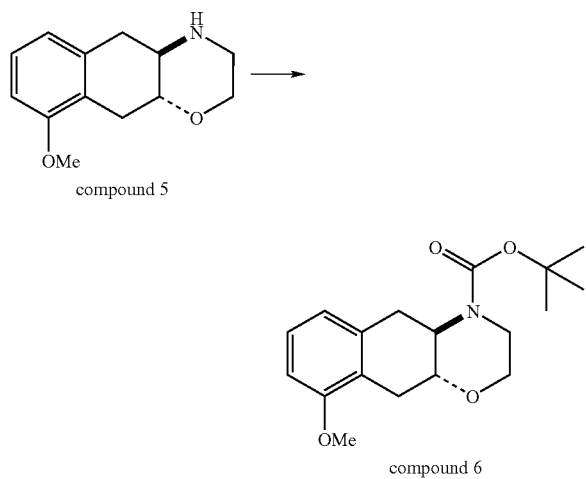

Racemic trans-9-methoxy-2,3,4a,5,10,10a-hexahydro-naphtho[2,3-b][1,4]oxazine-4-carboxylic acid tert-butyl ester (Compound 6)

Compound 5 from the previous step was dissolved in THF (70 mL), and Et₃N (1.45 mL) and Boc₂O (1.52 g) were added, before the mixture was stirred for 3 days at rt. The solution was concentrated in vacuo to afford 1.45 g of compound 6 as a pale yellow oil after purification by silica gel chromatography (EtOAc/heptane).

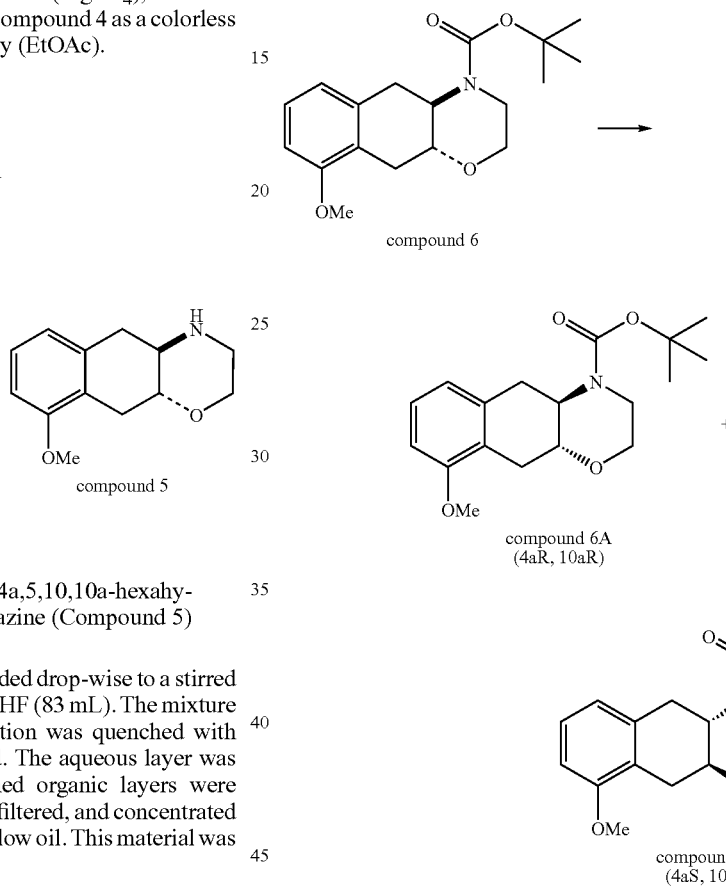

Resolution of racemic trans-9-methoxy-2,3,4a,5,10,10a-hexahydro-naphtho[2,3-b][1,4]oxazine-4-carboxylic acid tert-butyl ester (Resolution of Compound 6 into Compounds 6A and 6B)

Compound 6 (1.38 g) was resolved by chiral SFC on a Berger SFC multigram II instrument equipped with a Chiralpak AD 21.2×250 mm column. Solvent system: CO₂/EtOH/Et₂NH (70:29.9:0.1) Method: constant gradient with a flow rate of 50 mL/min. Fraction collection was performed by UV 230 nm detection. Fast eluting enantiomer (4aS,10aS enantiomer; compound 6B): 0.622 g as a white solid. Mp=89-90° C. $\alpha_D$+190.1 (C=0.25, MeOH). Slow eluting enantiomer (4aR, 10aR enantiomer; compound 6A): 0.633 g as a white solid. Mp=89-90° C. $\alpha_D$−184.8 (C=0.25, MeOH). The configuration of the stereogenic centers was determined by X-ray crystallography of a derivative (example 5d2).

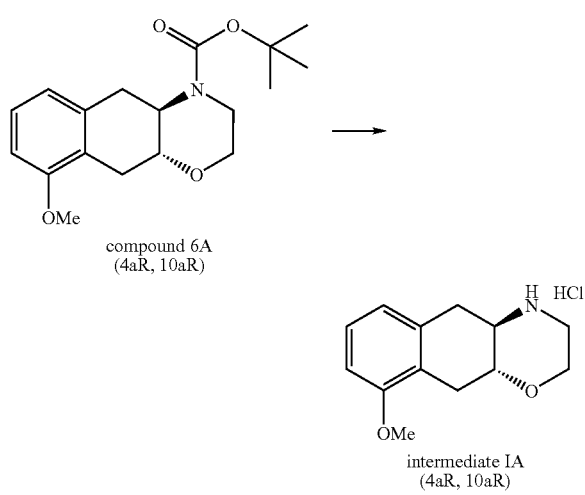

compound 6A
(4aR, 10aR)

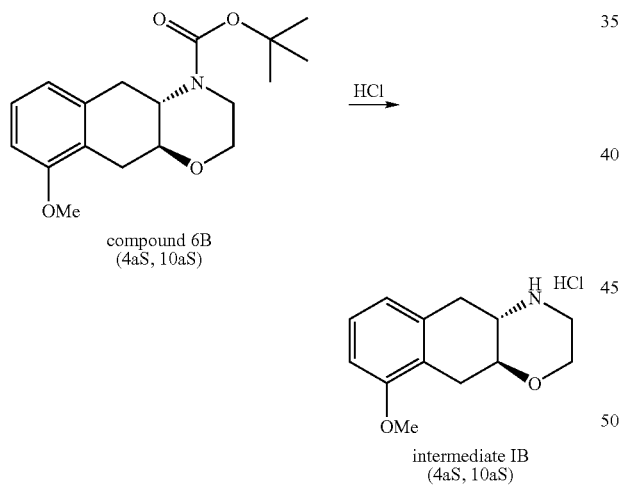

compound 6B
(4aS, 10aS)

intermediate IA
(4aR, 10aR)

intermediate IB
(4aS, 10aS)

(4aR,10aR)-9-methoxy-3,4,4a,5,10,10a-hexahydro-2H-naphtho[2,3-b][1,4]oxazine hydrochloride (Intermediate IA)

To a stirred solution of compound 6A (545 mg) in MeOH (11 mL) was added HCl (14 mL, 5M in Et$_2$O). After stirring for 45 min, the mixture was concentrated in vacuo. Yield: 418 mg of intermediate IA as a white solid. mp dec.>280° C.; LC/MS: ELSD: 99.6%; UV: 99.2%; MH$^+$: 220.2. NMR data identical to the data reported for intermediate IB. Anal. Calcd for C$_{13}$H$_{17}$NO$_2$.HCl: C, 61.05; H, 7.09; N, 5.48. Found: C, 60.93; H, 7.26; N, 5.42.

(4aS,10aS)-9-methoxy-3,4,4a,5,10,10a-hexahydro-2H-naphtho[2,3-b][1,4]oxazine hydrochloride (Intermediate IB)

To a stirred solution of compound 6B (543 mg) in MeOH (11 mL) was added HCl (14 mL, 5M in Et$_2$O). After stirring for 45 min, the mixture was concentrated in vacuo. Yield: 436 mg of intermediate IB as a white solid. mp dec.>280° C.; LC/MS: ELSD: 98.7%; UV: 93.7%; MH$^+$: 220.2. $^1$H NMR (500 MHz, DMSO) δ 2.40 (dd, 1H), 3.00-3.20 (br m, 4H), 3.30 (m, 1H), 3.75 (s, 3H), 3.90 (m, 2H), 4.00 (dd, 1H), 6.75 (d, 1H), 6.80 (d, 1H), 7.15 (t, 1H), 9.75 (b, 1H). $^{13}$C NMR (DMSO) δ: 157.0, 133.3, 127.6, 121.6, 120.8, 108.6, 73.2, 63.1, 55.7, 54.3, 43.2, 31.4, 29.1. Anal. Calcd for C$_{13}$H$_{17}$NO$_2$.HCl: C, 61.05; H, 7.09; N, 5.48. Found: C, 61.11; H, 7.25; N, 5.41.

Preparation of Intermediates IIA, IIIA, IVA, VA, VI and VII.

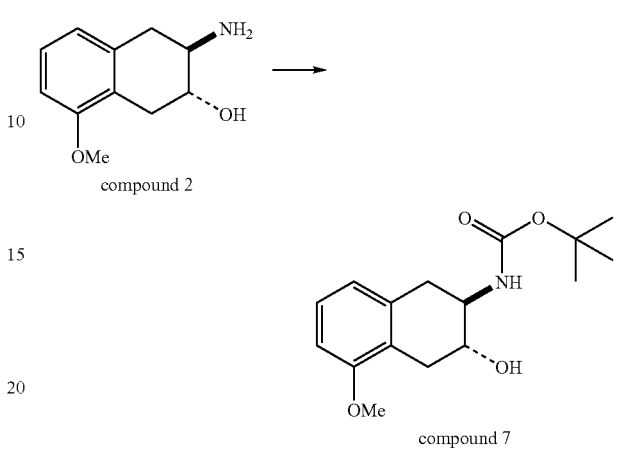

compound 2

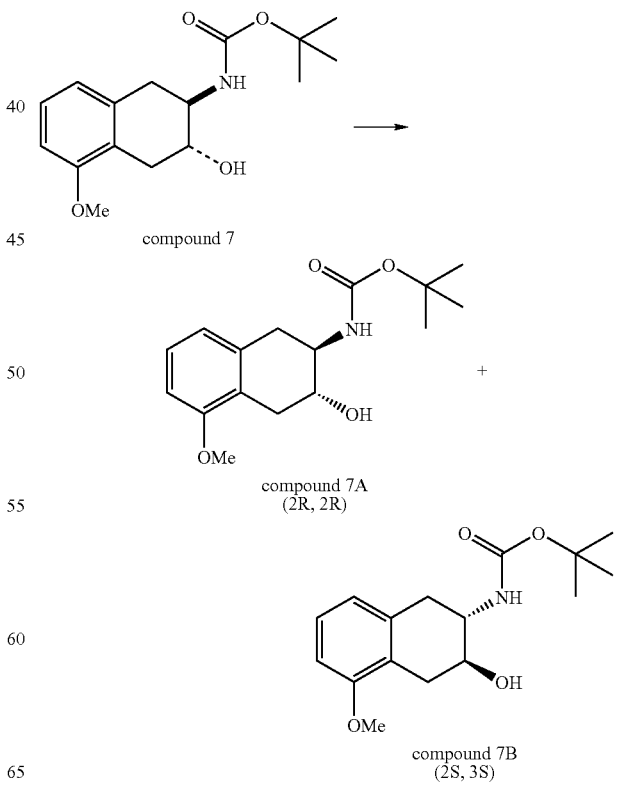

compound 7

Racemic trans-3-hydroxy-5-methoxy-1,2,3,4-tetrahydro-naphthalen-2-yl)-carbamic acid tert-butyl ester (Compound 7)

Compound 2 (7.36 g) was dissolved in THF (175 mL), and Et$_3$N (7.7 mL) and Boc$_2$O (7.74 g) were added. The mixture was stirred at rt overnight and concentrated in vacuo. The crude product was purified by silica gel chromatography (EtOAc/heptane) to afford 6.90 g of compound 7 as a white solid.

compound 7 compound 7A
(2R, 2R)

compound 7B
(2S, 3S)

Resolution of racemic trans-3-hydroxy-5-methoxy-1,2,3,4-tetrahydro-naphthalen-2-yl)-carbamic acid tert-butyl ester (Resolution of Compound 7 into Compounds 7A and 7B)

Compound 7 (13 g) was resolved by chiral SFC on a Berger SFC multigram II instrument equipped with a Chiralpak AD 21.2×250 mm column. Solvent system: $CO_2$/EtOH/$Et_2$NH (70:29.9:0.1) Method: constant gradient with a flow rate of 50 mL/min. Fraction collection was performed by UV 230 nm detection. Fast eluting enantiomer (2S,3S enantiomer; compound 7B): 5.14 g as a white solid. Mp=161-162° C. Slow eluting enantiomer (2R,3R enantiomer; compound 7A): 5.17 g as a white solid. Mp=161-162° C.

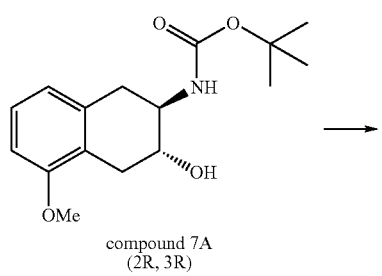

compound 7A
(2R, 3R)

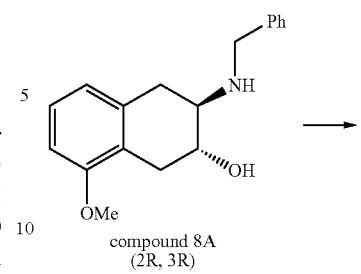

compound 8A
(2R, 3R)

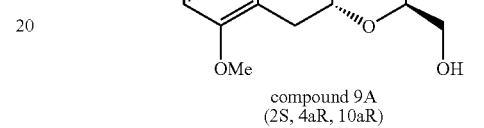

(2R,3R)-3-Benzylamino-8-methoxy-1,2,3,4-tetrahydro-naphthalen-2-ol (Compound 8A)

To a stirred solution of compound 7A (5.10 g) in MeOH (35 mL) was added HCl (70 mL, 5M in $Et_2O$). After stirring overnight at rt, the mixture was concentrated in vacuo. Yield: 4.09 g of the hydrochloride salt of (2R,3R)-3-amino-8-methoxy-1,2,3,4-tetrahydro-naphthalen-2-ol as a white solid. 3.84 g of this material was suspended in THF (140 mL) and $Et_3N$ (4.6 mL) and benzoylchloride (2.58 g) were added. The mixture was stirred at rt for 3.5 h overnight and then quenched by adding EtOAc (400 mL) and 2M HCl (300 mL). The organic phase was washed with brine and concentrated in vacuo. LAH (1M in THF, 20 mL) was added to this material (4.63 g) at 5° C. The reaction mixture were heated to 100° C. for 1200 sec in a sealed microwave process vial and then quenched by adding wet $Na_2SO_4$. The solution were diluted by adding diethyl ether (60 mL) and THF (60 mL) and then filtered through dry $Na_2SO_4$ and concentrated in vacuo. Yield: 3.69 g of compound 8A as a white solid.

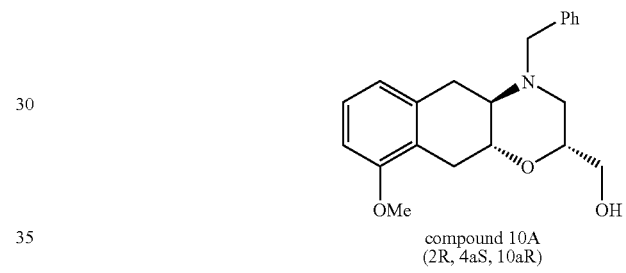

compound 9A
(2S, 4aR, 10aR)

+ compound 10A
(2R, 4aS, 10aR)

((2S,4aR,10aR)-4-Benzyl-9-methoxy-3,4,4a,5,10,10a-hexahydro-2H-naphtho[2,3-b][1,4]oxazin-2-yl)-methanol (Compound 9A) and ((2R,4aR,10aR)-4-benzyl-9-methoxy-3,4,4a,5,10,10a-hexahydro-2H-naphtho[2,3-b][1,4]oxazin-2-yl)-methanol (Compound 10A)

R-(−)-epichlorohydrin (1.95 mL dissolved in 10 mL heptane) was added to a stirred solution of compound 8A (1.42 g) suspended in 1,2-DCE (5 mL). The reaction mixture was refluxed at 115° C. overnight. The solvent was evaporated off and the residue was purified by silicagel chromatography (10-50% EtOAc in heptane). Yield of this intermediate: 1.60 g, LC/MS (m102): 1.15 min (MH 376.1), ELSD 99%, WV 76%. 2M NaOH (50 mL) was added to this intermediate (1.60 g) and the solution was refluxed at 130° C. overnight, cooled to rt and then quenched by adding THF (75 mL). The phases were separated and the organic phase were washed with brine and concentrated in vacuo. The crude product were purified by silica gel chromatography (EtOAc/heptane) to afford 0.457 g of compound 9A as a white solid (fast eluting isomer) and 0.340 g of compound 10A as a white solid (slow eluting isomer).

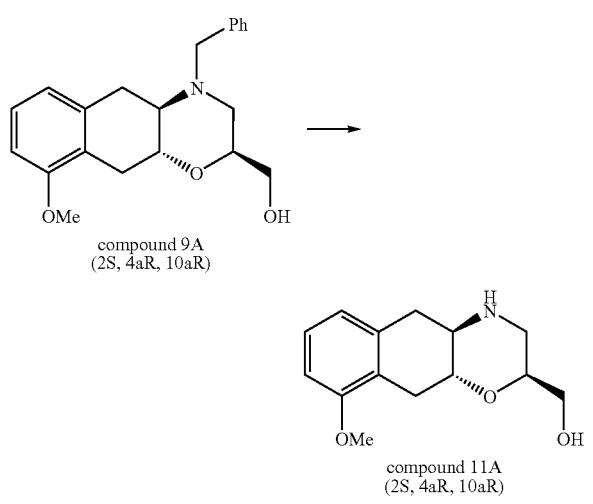

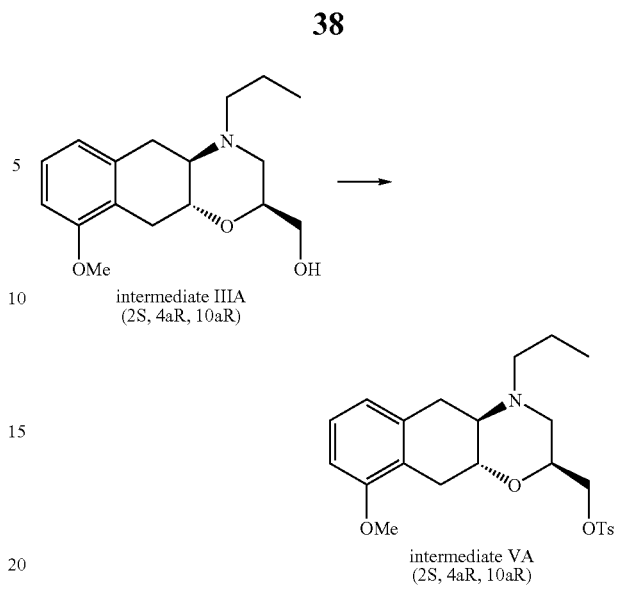

((2S,4aR,10aR)-9-Methoxy-3,4,4a,5,10,10a-hexahydro-2H-naphtho[2,3-b][1,4]oxazin-2-yl)-methanol (Compound 11A)

Compound 9A (447 mg) was dissolved in EtOH (56 mL). 10% Pd/C (110 mg) was added and the solution was hydrogenated overnight. The catalyst was filtered off and the solvent was evaporated off. Yield of compound 11A: 316 mg.

Toluene-4-sulfonic acid (2S,4aR,10aR)-9-methoxy-4-n-propyl-3,4,4a,5,10,10a-hexahydro-2H-naphtho[2,3-b][1,4]oxazin-2-ylmethyl ester (Intermediate VA)

TsCl (160 mg) was added to a stirred solution of intermediate IIIA (160 mg) in pyridine (3 mL). The reaction mixture was stirred at rt for 5 h and then quenched by addition of water (0.2 mL). After 20 min EtOAc (25 mL) and saturated aqueous NaHCO$_3$ (10 mL) were added. The organic phase were washed with saturated NaHCO$_3$ (10 mL) and then washed with brine, and the solvent was evaporated off to afford 187 mg of intermediate VA as a solid. LC/MS (method 101): RT 1.12 min, ELSD 98.4%, UV 73.5%. MH$^+$: 446.7.

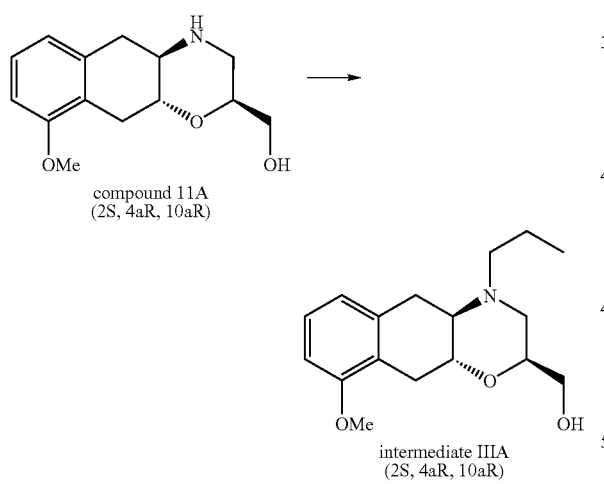

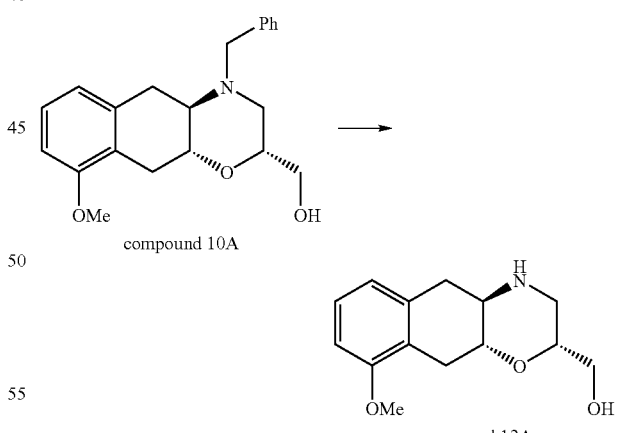

((2S,4aR,10aR)-9-Methoxy-4-n-propyl-3,4,4a,5,10,10a-hexahydro-2H-naphtho[2,3-b][1,4]oxazin-2-yl)-methanol (Intermediate IIIA)

To a stirred solution of compound 11A (316 mg) in DMF (6.3 mL) was added K$_2$CO$_3$ (369 mg) and then n-propyliodide (0.11 mL). The reaction mixture was stirred at rt overnight and then quenched by addition of EtOAc (40 mL) and brine (25 mL). The organic phase was washed with more brine, and the solvent was evaporated off. The crude product was purified by silica gel chromatography (EtOAc/heptane) to afford 196 mg of intermediate IIIA.

((2R,4aR,10aR)-9-Methoxy-3,4,4a,5,10,10a-hexahydro-2H-naphtho[2,3-b][1,4]oxazin-2-yl)-methanol (Compound 12A)

This material was prepared from compound 10A (340 mg) in a similar manner as described for compound 11A. Yield: 288 mg.

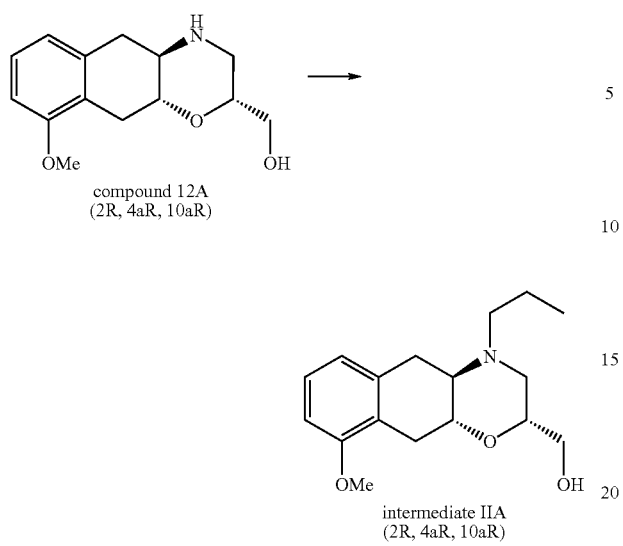

compound 12A
(2R, 4aR, 10aR)

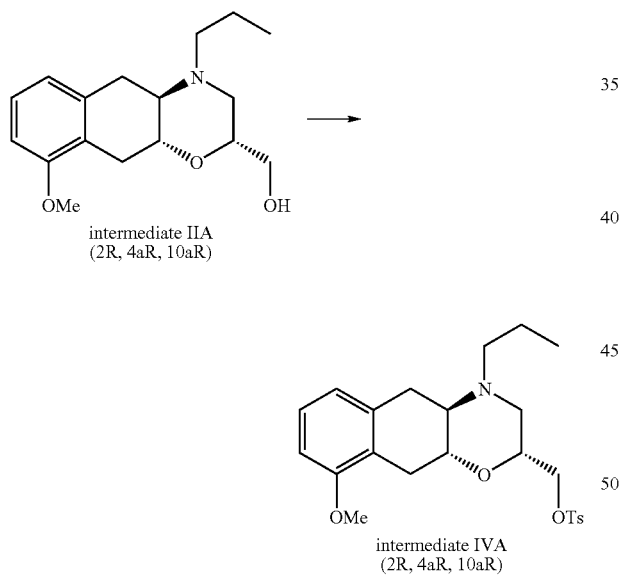

intermediate IIA
(2R, 4aR, 10aR)

((2R,4aR,10aR)-9-Methoxy-4-n-propyl-3,4,4a,5,10,10a-hexahydro-2H-naphtho[2,3-b][1,4]oxazin-2-yl)-methanol (Intermediate IIA) was prepared from compound 12A in a similar manner as described for Intermediate IIA. Yield: 149 mg intermediate IIA
(2R, 4aR, 10aR)

intermediate IVA
(2R, 4aR, 10aR)

Toluene-4-sulfonic acid (2R,4aR,10aR)-9-methoxy-4-n-propyl-3,4,4a,5,10,10a-hexahydro-2H-naphtho[2,3-b][1,4]oxazin-2-ylmethyl ester (Intermediate IVA)

This material was prepared from intermediate IIA in a similar manner as described for intermediate VA. Yield: 238 mg. LC/MS (method 101): RT 1.09 min, ELSD 98%, UV 65%. MH+: 446.7.

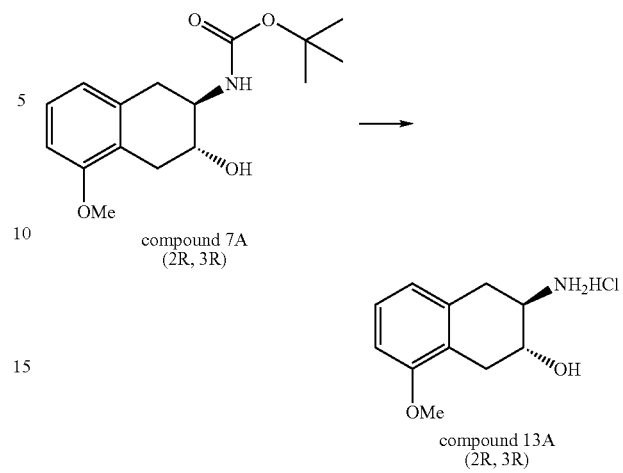

compound 7A
(2R, 3R)

compound 13A
(2R, 3R)

(2R,3R)-3-Amino-8-methoxy-1,2,3,4-tetrahydro-naphthalen-2-ol (Compound 13A)

To a stirred solution of compound 7A (7.19 g in MeOH (100 mL) was added HCl (99mL, 2M in Et$_2$O). After stirring for two hours the solution was filtered to afford compound 13A as a white solid. Yield: 5.05 g. LC/MS (method 350): RT 0.32 min, ELSD 97.0%, UV 100%. MH$^2$: 194.1. $\alpha_D$–105.5 (C=0.25, MeOH) $^1$H NMR (500 MHz, DMSO) δ : 2.41 (dd, 1H), 2.95 (dd, 1H), 3.09-3.17 (m, 3H), 3.77 (s, 3H), 3.87 (m, 1H), 5.75 (1, 1H), 6.71 (d, 1H), 6.79 (d, 1H), 7.13 (t, 1H), 8.32 (s, 3H). $^{13}$C NMR (DMSO) δ : 157.0, 133.8, 127.3, 122.7, 120.7, 108.3, 67.2, 55.7, 52.3, 32.6, 31.9.

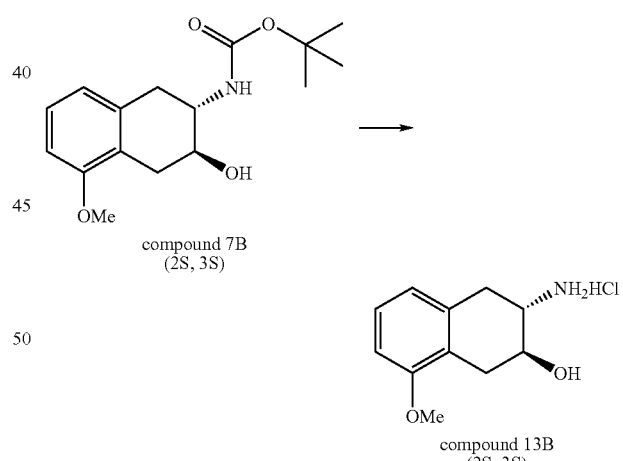

compound 7B
(2S, 3S)

compound 13B
(2S, 3S)

(2S,3S)-3-Amino-8-methoxy-1,2,3,4-tetrahydro-naphthalen-2-ol (Compound 13B)

This material was synthesized from compound 7B (7.44 g) in a similar manner as described for compound 13A. Yield: 5.34 g of compound 13B as a white solid. LC/MS (method 350): RT 0.32 min, ELSD 100%, UV 100%. MH: 194.1. $\alpha_D$+104.6 (C=0.25, MeOH). NMR data identical to the data reported for compound 13A.

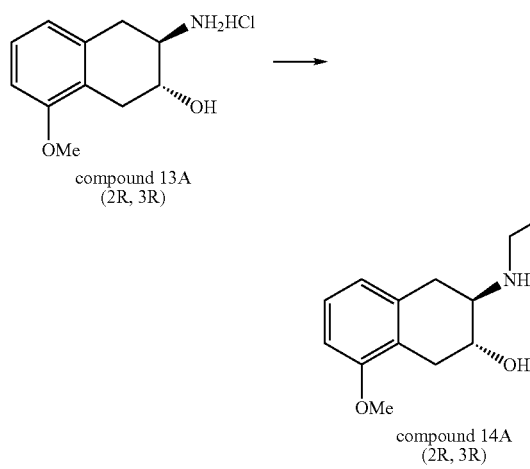

(2R,3R)-8-Methoxy-3-n-propylamino-1,2,3,4-tetrahydro-naphthalen-2-ol (Compound 14A)

Compound 13A (1.50 g) was suspended in THF (15 mL) and Et₃N (1.80 mL) and propionyl chloride (0.60 mL) were added. The solution was stirred for 20 minutes. LAH (1M in THF, 10 mL) was added drop-wise under stirring at rt and the reaction mixture were heated to 90° C. for 1200 sec. in a sealed microwave process vial. The reaction was quenched with wet Na₂SO₄. The mixture was diluted with THF (50 mL), filtered over dry Na₂SO₄ and concentrated in vacuo. Yield: 1.21 g of compound 14A as an oil. LC/MS (method 350): RT 0.40 min, ELSD 100%, UV 100%. MH⁺: 235.9. ¹H NMR (500 MHz, CDCl₃) δ 0.89 (t, J=7.6 Hz, 3H), 1.43-1.52 (m, 2H), 2.37-2.51 (m, 3H), 2.61-2.68 (m, 1H), 2.74-2.80 (m, 1H), 3.14 (dd, J=4.93, J=16.0, 1H), 3.22-3.29 (dd, J=16.9, J=5.9, 1H), 3.56-3.63 (m, 1H), 3.73 (s, 1H), 6.60 (d, J=8.05, 1H), 6.62 (d, J=7.89, 1H), 7.03 (t, J=7.86, 1H). ¹³C NMR (500 MHz, CDCl₃) δ: 157.7 136.4, 127.0, 123.8, 121.2, 107.7, 71.0, 59.8, 55.7, 49.5, 35.7, 32.1, 24.1, 12.2.

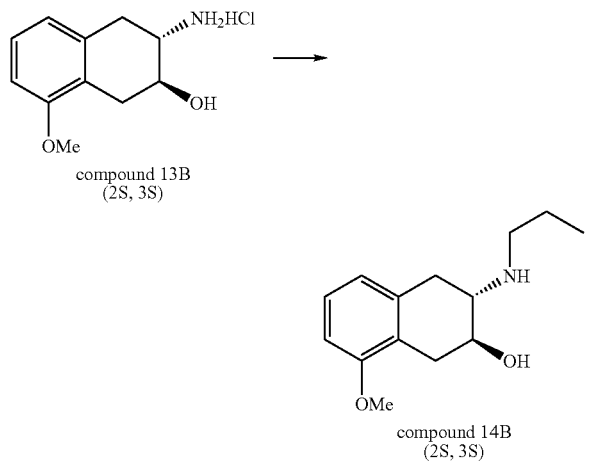

(2S,3S)-8-Methoxy-3-n-propylamino-1,2,3,4-tetrahydro-naphthalen-2-ol (Compound 14B)

This material was synthesized from compound 13B (1.15 g). Yield: 960 mg of compound 14B as an oil. LC/MS (method 350): RT 0.40 mm, ELSD 99.2%, UV 100%. MH⁺: 235.9.

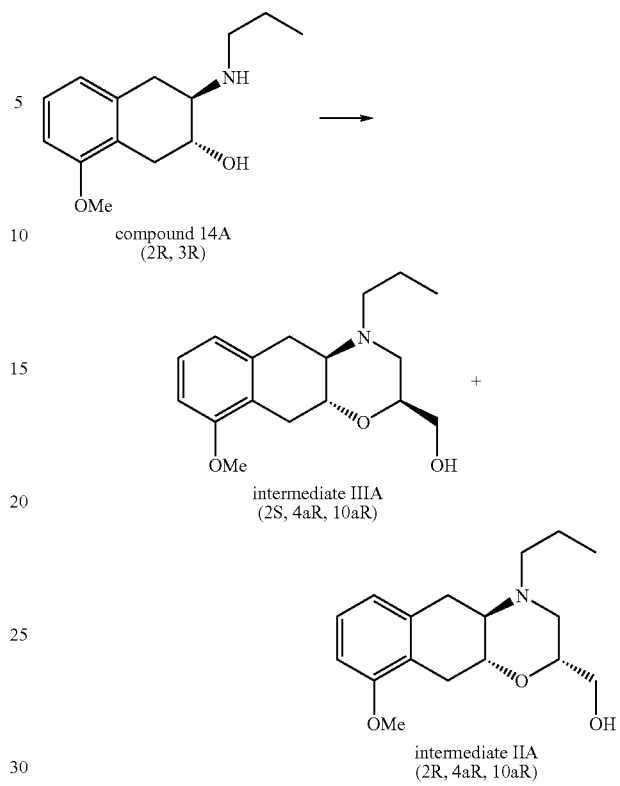

Intermediate IIA and intermediate IIIA. S-(+)-epichlorohydrin (1.22 mL) was added to a stirred solution of compound 14A (751 mg) dissolved in 1,2-DCE (3.2 mL). The reaction mixture was refluxed at 120° C. overnight, and concentrated in vacuo. NaOH (8.7 mL, 2M) was added to the residue and the mixture was refluxed at 130° C. overnight. The solution was allowed to cool to rt, before THF (17.5 mL) was added. The organic phase was washed with brine (5 mL) and concentrated in vacuo. The two isomers was separated by silica-gel chromatography (using 0-100% EtOAc in heptane) to afford 116 mg of the fast eluting isomer ((2S,4aR,10aR)-9-methoxy-4-n-propyl-3,4,4a,5,10,10a-hexahydro-2H-naphtho[2,3-b][1,4]oxazin-2-yl)-methanol (intermediate IIIA): LC/MS: ELSD: 100.0%; UV: 90.4%; MH⁺291.8. ¹H NMR (500 MHz, CDCl₃) δ 0.87 (t, J=7.48, 3H), 1.38-1.59 (m, 2H), 2.09-2.15 (m, 1H), 2.30-2.40 (m, 1H), 2.59 (dd, J=15.86, J=11.69, 1H), 2.65 (dd, J=11.87, J=3.99, 1H), 2.99 (d, J=11.81, 1H), 3.11 (t, J=5.59, 1H), 3.14 (t, J=5.14, 1H), 3.74 (s, 3H), 3.83-3.92 (m, 2H), 4.07-4.14 (m, 2H), 6.60 (d, J=8.21, 1H), 6.63 (d, J=7.86, 1H), 7.04 (t, J=8.03, 1H). ¹³C NMR (500 MHz, CDCl₃) δ: 157.5 135.5, 127.1, 123.4, 121.1, 107.7, 72.4, 72.3, 67.0, 60.9, 55.7, 55.1, 53.2, 33.9, 30.7, 19.1, 12.3.

and 76 mg of the slow eluting isomer ((2R,4aR,10aR)-9-methoxy-4-n-propyl-3,4,4a,5,10,10a-hexahydro-2H-naphtho[2,3-b][1,4]oxazin-2-yl)-methanol (intermediate IIA) LC/MS: ELSD: 100.0%; UV: 100.0%; MH⁺291.8; R_f=0.41. ¹H NMR (500 MHz, CDCl₃) δ 0.85 (t, J=7.3 Hz, 3H), 1.45-1.59 (m, 2H), 2.24-2.32 (m, 3H), 2.43 (dd, J=16.9, J=10.6, 1H), 2.60 (dd, J=11.8, J=15.4, 1H), 2.73 (m, 1H), 2.79 (d, J=11.18, 1H), 3.10-3.19 (m, 2H), 3.55 (dd, J=6.35, J=11.64, 1H), (3.58-3.66 (m, 2H), 3.74 (s, 3H), 3.78 (br, 1H), 6.61 (d, J=8.21, 1H), 6.66 (d, J=7.92, 1H), 7.05 (t, J=7.88, 1H). $^{13}$C NMR (500 MHz, CDCl$_3$) δ:157.5 135.8, 127.1, 123.4, 121.2, 107.7, 76.9, 76.0, 64.7, 60.9, 55.7, 55.6, 53.4, 33.9, 30.1, 18.7, 12.4.

Intermediates IIA and IIIA were prepared from compound 14A (1.1 g) and R-(−)-epichlorohydrin (1.76 ml) under the conditions described above. Yield 338 mg of Intermediate IIA and 247 mg of Intermediate IIA.

Preparation of Intermediates IIB and IIIB.

Intermediates IIB and IIIB were prepared from compound 7B in several steps, in a similar manner as described for the enantiomer 7A using S-(+)-epichlorohydrin. Intermediates IIB and IIIB were also prepared from compound 14B in a similar manner as described for the enantiomer 14A, using either S-(+)-epichlorohydrin or R-(−)-epichlorohydrin.

Preparation of Intermediate IVB and VB.

Intermediates IVB and VB were prepared from intermediate IIB and IIIB in a similar manner as described for the enantiomers.

Preparation of Intermediate VI and VII

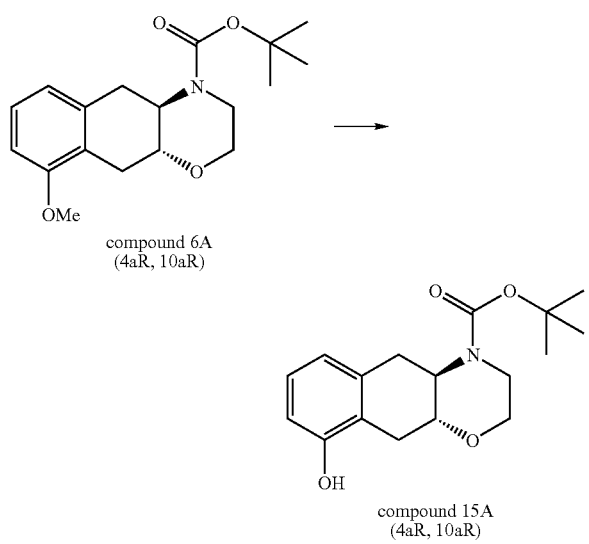

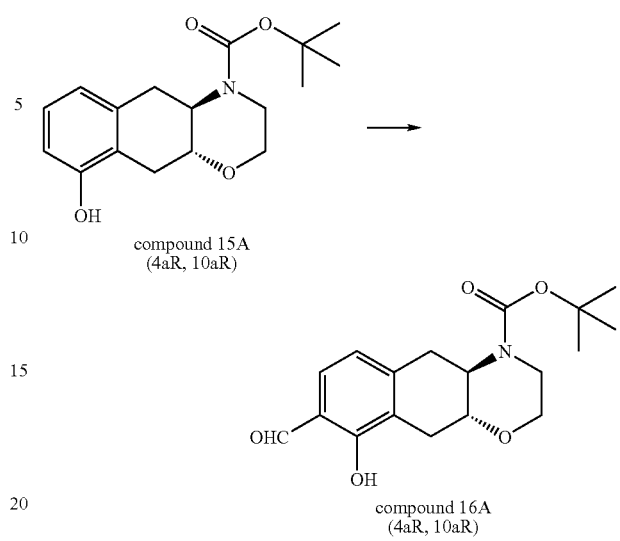

(4aR,10aR)-8-Formyl-9-hydroxy-2,3,4a,5,10,10a-hexahydro-naphtho[2,3-b][1,4]oxazine-4-carboxylic acid tert-butyl ester (Compound 14A)

Compound 15A (375 mg) was dissolved in dry toluene (4 mL). The toluene was removed by concentration in vacuo, and more toluene (20 mL) was added. Ethyl magnesium bromide (0.45 mL; 3M in Et$_2$O) was added drop-wise at rt and the solution was stirred for 15 min. Approximately ¼ of the solvent was removed by concentration in vacuo and paraformaldehyde (95 mg) and then HMPA (0.21 mL) were added. The solution was stirred at 90° C. for 2.5 h and then transferred using a syringe to a sealed microwave reactor vial and heated for 120° C. for 0.5 h. The solution was kept at rt for 3 days. The solution was portioned between sat. NH$_4$Cl (30 mL) and Et$_2$O (120 mL). The organic layer was washed with brine, dried (Na$_2$SO$_4$), and concentrated in vacuo. The crude product was purified by silica gel chromatography (EtOAc/heptane) to give 230 mg of compound 16A as a white solid.

(4aR,10aR)-9-Hydroxy-2,3,4a,5,10,10a-hexahydro-naphtho[2,3-b][1,4]oxazine-4-carboxylic acid tert-butyl ester (Compound 15A)

L-selectride (13.5 mL, 1M in THF) was added to compound 6A (901 mg) at rt. The solution was heated at 110° C. in a sealed microwave reactor vial for 6 h. More L-selectride (1.5 mL, 1M in THF) was added and the solution was heated at 110° C. for 1 h. The yellow solution was poured into an ice/water mixture (45 mL) and sat. NaHCO$_3$ (45 mL). The mixture was extracted with Et$_2$O (3×90 mL). The combined organic layers were washed with brine, dried (Na$_2$SO$_4$), and concentrated in vacuo. The crude product was purified by silica gel chromatography (MeOH/EtOAc/heptane) to give 530 mg of compound 15A as a white solid.

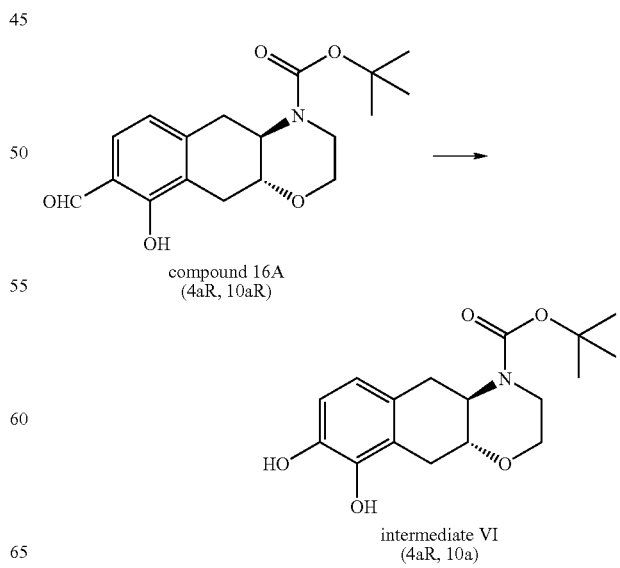

(4aR,10aR)-8,9-Dihydroxy-2,3,4a,5,10,10a-hexahydro-naphtho[2,3-b][1,4]oxazine-4-carboxylic acid tert-butyl ester (Intermediate VI)

A solution of compound 16A (225 mg) in MeOH (3.4 mL) was degassed. 1M NaOH (0.67 mL) and 35% $H_2O_2$ (0.28 mL) were added drop-wise and the red solution was stirred for 10 min at rt. A mixture of HCl (10 mL, 2M in $Et_2O$) and MeOH (20 mL) were added and the solution became yellow. $Et_2O$ (30 mL) and brine (5 mL) were immediately added. The organic layer was washed with brine, dried ($Na_2SO_4$), and concentrated in vacuo to give intermediate VI as a brown powder.

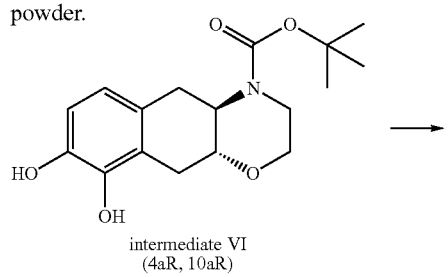

intermediate VI
(4aR, 10aR)

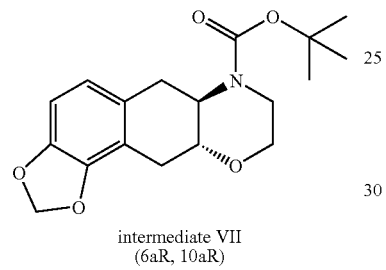

intermediate VII
(6aR, 10aR)

(6aR,10aR)-6,6a,8,9,10a,11-Hexahydro-1,3,10-trioxa-7-aza-cyclopenta[a]anthracene-7-carboxylic acid tert-butyl ester (Intermediate VII)

Intermediate VI (60 mg), $Cs_2CO_3$ (33 mg) and $CH_2BrCl$ (48 mg) and DMF (1 mL) were heated to 110° C. for 0.5 h in a sealed microwave reactor vial. More $CH_2BrCl$ (33 mg in 0.2 mL DMF) was added and the mixture was heated 110° C. for 0.5 h. The reaction mixture was purified by silica gel chromatography (EtOAc/heptane). Yield: 18 mg of intermediate VII.

Preparation of the Compounds of the Invention

The invention disclosed herein is further illustrated by the following non-limiting examples.

Example 1

1a1. (4aR,10aR)-9-Methoxy-4-methyl-3,4,4a,5,10,10a-hexahydro-2H-naphtho[2,3-b][1,4]oxazine

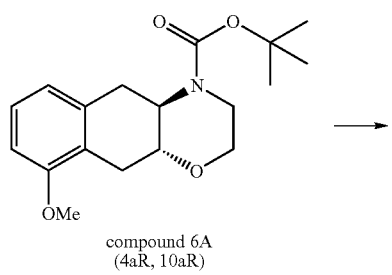

compound 6A
(4aR, 10aR)

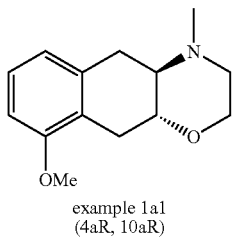

example 1a1
(4aR, 10aR)

Compound 6A was dissolved in dry THF (5 mL). LAH (1M in THF, 1.5 mL) was added drop-wise at rt and the solution was heated to 90° C. for 15 minutes in a sealed microwave process vial. After cooling to rt, MeOH (0.3 mL) and ice-cold water (10 mL) was slowly added, and the product was extracted with $Et_2O$ (3×20 mL). The combined organic phases were washed with brine, dried ($MgSO_4$), and concentrated in vacuo to give example 1a1. Yield: 107 mg. TLC: Rf=0.19 (EtOAc).

1a2. (4aS,10aS)-9-Methoxy-4-methyl-3,4,4a,5,10,10a-hexahydro-2H-naphtho[2,3b][1,4]oxazine

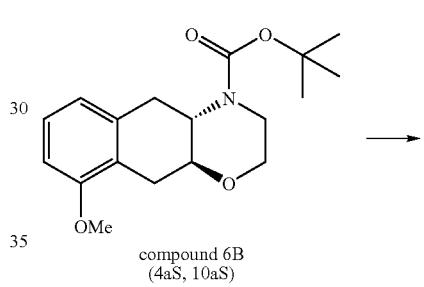

compound 6B
(4aS, 10aS)

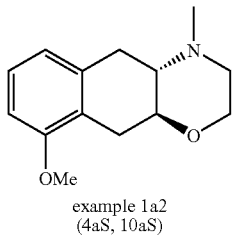

example 1a2
(4aS, 10aS)

The procedure described for example 1a1 was followed starting from compound 6B (160 mg) to give example 1a2. Yield: 78 mg.

Example 2

2a1. (4aR,10aR)-4-Ethyl-9-methoxy-3,4,4a,5,10,10a-hexahydro-2H-naphtho[2,3b][1,4]oxazine

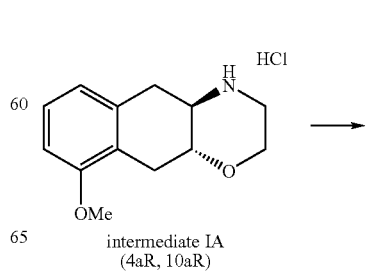

intermediate IA
(4aR, 10aR)

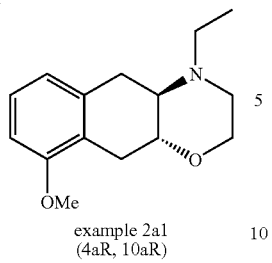

example 2a1
(4aR, 10aR)

K$_2$CO$_3$ (1.50 mmol) and ethyl iodide (2.2 mmol) are added to a stirred solution of intermediate IA (0.39 mmol) in DMF (9 mL). The mixture is stirred at 55° C. for 3 h. Water (20 mL) is added and the product is extracted into Et$_2$O (3×10 mL). The combined organic phases is washed with brine and sat. NH$_4$Cl, dried (MgSO$_4$), and concentrated in vacuo to give example 2a1.

2a2. (4aS,10aS)-4-Ethyl-9-methoxy-3,4,4a,5,10,10a-hexahydro-2H-naphtho[2,3b][1,4]oxazine

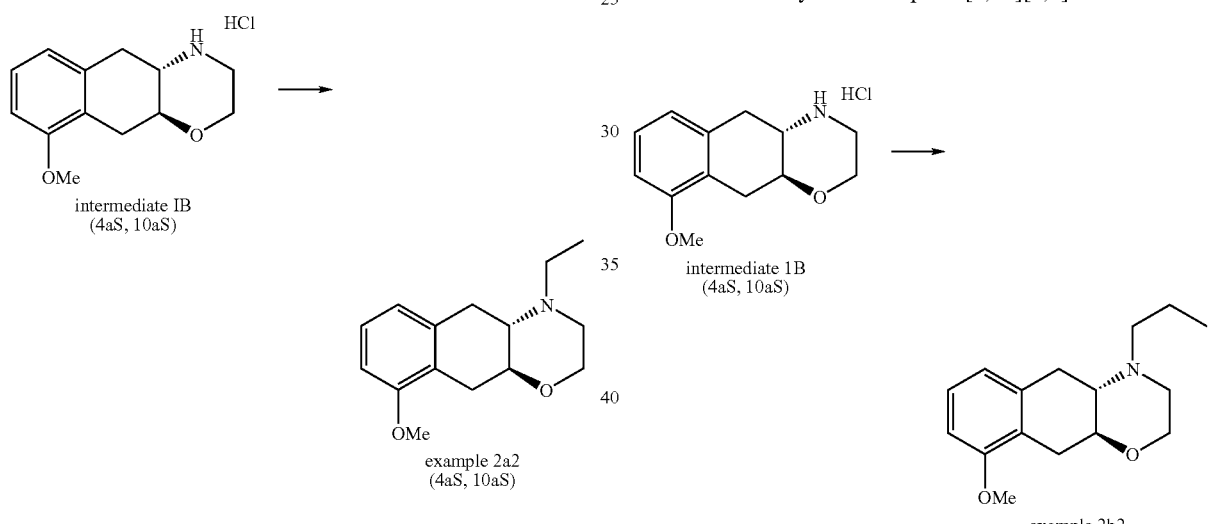

intermediate IB
(4aS, 10aS)

example 2a2
(4aS, 10aS)

K$_2$CO$_3$ (1.50 mmol) and ethyl iodide (2.2 mmol) are added to a stirred solution of intermediate IB (0.39 mmol) in DMF (9 mL). The mixture is stirred at 55° C. for 3 h. Water (20 mL) is added and the product is extracted into Et$_2$O (3×10 mL). The combined organic phases is washed with brine and sat. NH$_4$Cl, dried (MgSO$_4$), and concentrated in vacuo to give example 2a2.

2b1. (4aR,10aR)-9-methoxy-4-n-Propyl-3,4,4a,5,10,10a-hexahydro-2H-naphtho[2,3b][1,4]oxazine

intermediate IA
(4aR, 10aR)

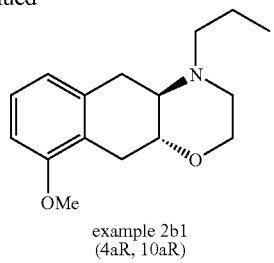

example 2b1
(4aR, 10aR)

K$_2$CO$_3$ (176 mg, 1.50 mmol) and n-propyl iodide (375 mg, 2.2 mmol) were added to a stirred solution of intermediate IA (100 mg, 0.39 mmol) in DMF (9 mL). The mixture was stirred at 55° C. for 3 h. Water (20 mL) was added and the product was extracted into Et$_2$O (3×10 mL). The combined organic phases were washed with brine and sat. NH$_4$Cl, dried (MgSO$_4$), and concentrated in vacuo to give example 2b1 as a white solid. Yield: 93 mg. LC/MS (method 25): RT 0.58 min, ELSD 100%, UV 92%. TLC: Rf=0.51 (EtOAC)

2b2. (4aS,10aS)-9-Methoxy-4-n-propyl-3,4,4a,5,10,10a-hexahydro-2H-naphtho[2,3b][1,4]oxazine The procedure described for example 2b1 was followed starting from intermediate IB (100 mg) to give example 2b2. Yield: 102 mg. LC/S (method 25): RT 0.60 min, ELSD 100%, UV 93%. TLC: Rf=0.51 (EtOAc).

2c1. (4aR,10aR)-4-Allyl-9-methoxy-3,4,4a,5,10,10a-hexahydro-2H-naphtho[2,3b][1,4]oxazine intermediate 1A
(4aR, 10aR)

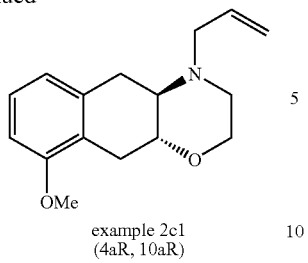

example 2c1
(4aR, 10aR)

K$_2$CO$_3$ (202 mg) and allyl bromide (300 mg) were added to a stirred solution of intermediate IA (115 mg) in DMF (10 mL). The mixture was stirred at 55° C. for 5 h. Water (20 mL) and sat. NaHCO$_3$ (10 mL) were added and the product was extracted into Et$_2$O (3×20 mL). The combined organic phases were washed with brine, dried (MgSO$_4$), and concentrated in vacuo to give example 2c1 as a white solid. Yield: 117 mg. LC/MS (method 25): RT 0.97 min, ELSD 97%, UV 48%. MH$^+$: 260.3.

2c2. (4aS,10aS)-4-Allyl-9-methoxy-3,4,4a,5,10,10a-hexahydro-2H-naphtho[2,3b][1,4]oxazine

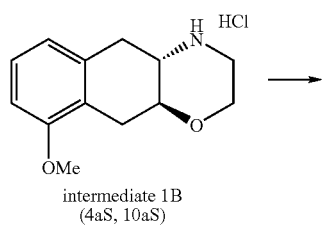

intermediate 1B
(4aS, 10aS)

→ example 2c2
(4aS, 10aS)

The procedure described for example 2c1 was followed starting from intermediate IB (115 mg) to give example 2c2. Yield: 117 mg. LC/MS (method 25): RT 0.97 min, ELSD 98%, UV 47%. MH$^+$: 260.3.

2d1. (4aR,10aR)-4-cyclo-Propylmethyl-9-methoxy-3,4,4a,5,10,10a-hexahydro-2H-naphtho[2,3b][1,4]oxazine

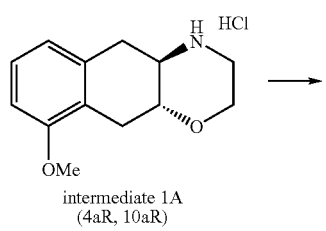

intermediate 1A
(4aR, 10aR)

→

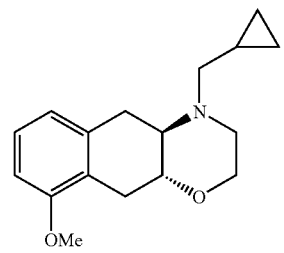

example 2d1
(4aR, 10aR)

K$_2$CO$_3$ (176 mg) and allyl bromide (292 mg) were added to a stirred solution of intermediate IA (100 mg) in DMF (9 mL). The mixture was stirred at 55° C. for 3 h. Water (20 mL) and sat. NaHCO$_3$ (10 mL) was added and the product was extracted into Et$_2$O (3×20 mL). The combined organic phases were washed with brine, dried (MgSO$_4$), and concentrated in vacuo to give example 2d1 as a white solid. Yield: 107 mg. LC/MS (method 25): RT 0.72 min, ELSD 100%, UV 92%. MH$^+$: 274.3.

2d2. (4aS,10aS)-4-cyclo-Propylmethyl-9-methoxy-3,4,4a,5,10,10a-hexahydro-2H-[2,3b][1,4]oxazine

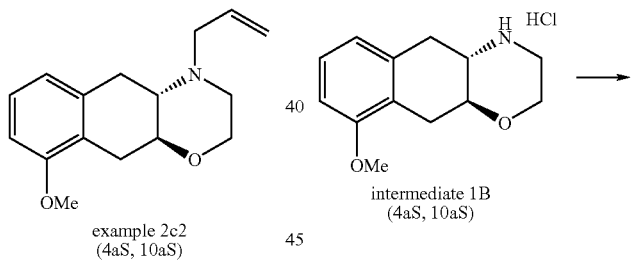

intermediate 1B
(4aS, 10aS)

→

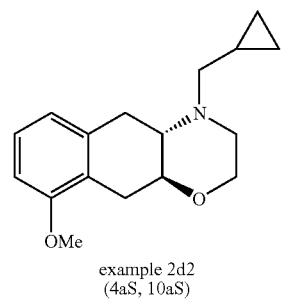

example 2d2
(4aS, 10aS)

The procedure described for example 2d1 was followed starting from intermediate IB (100 mg) to give example 2d2. Yield: 107 mg. LC/MS (method 25): RT 0.72 min, ELSD 99%, UV 90%. MH$^+$: 274.1.

Example 3

3a. (2S,4aR,10aR)-9-Methoxy-4-n-propyl-2-[1,2,4]triazol-1-ylmethyl-3,4,4a,5,10,10a-hexahydro-2H-naphtho[2,3-b][1,4]oxazine

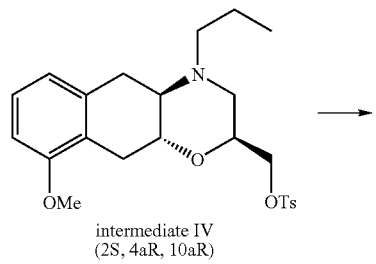
intermediate IV
(2S, 4aR, 10aR)

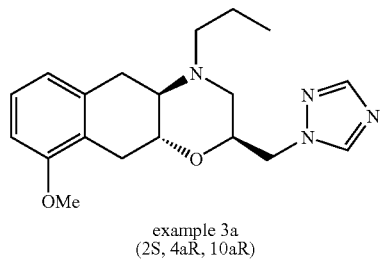
example 3a
(2S, 4aR, 10aR)

Intermediate IV (21 mg) was added to a stirred solution of 1,2,4-triazole (11 mg) and NaH (60% oil dispersion, 4 mg) in DMF at rt. The solution was heated to 100° C. for 30 minutes in a sealed microwave process vial, and then to 130° C. for 30 minutes. After cooling to rt, EtOAc (5 mL) was added, and the organic phase was washed with brine (2×5 mL), dried (MgSO$_4$), and concentrated in vacuo. The crude product was purified by silicagel chromatography (Eluent: 0-30% MeOH in EtOAc). Yield: 6 mg of example 3a as a clear oil. LC/MS (method 101): RT 0.69 min, ELSD 100%, UV 55%. MH$^+$: 343.2

3b. (2R,4aR,10aR)-9-Methoxy-4-n-propyl-2-[1,2,4]triazol-1-ylmethyl-3,4,4a, 5,10,10a-hexahydro-2H-naphtho[2,3-b][1,4]oxazine

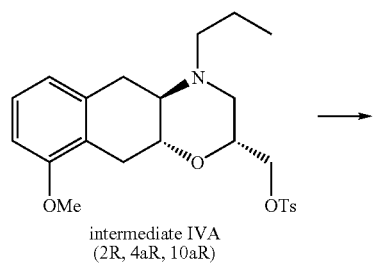
intermediate IVA
(2R, 4aR, 10aR)

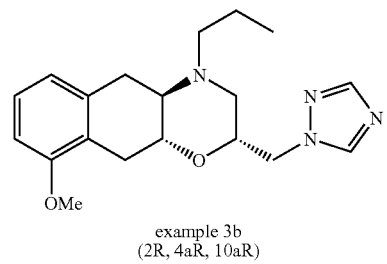
example 3b
(2R, 4aR, 10aR)

The procedure described for example 3a was followed starting from intermediate IVA (21 mg) to give example 3b. LC/MS (method 111): RT 0.59 min, ELSD 100%, UV 100%. MH$^+$: 343.1.

3c. (2S,4aR,10aR)-9-Methoxy-2-methylsulfanylmethyl-4-n-propyl-3,4,4a,5,10,10a-hexahydro-2H-naphtho[2,3-b][1,4]oxazine

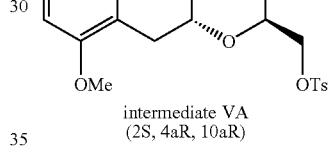
intermediate VA
(2S, 4aR, 10aR)

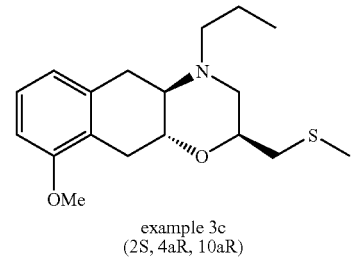
example 3c
(2S, 4aR, 10aR)

The procedure described for example 3d is followed starting from intermediate VA to give example 3c.

3d. (2R,4aR,10aR)-9-Methoxy-2-methylsulfanylmethyl-4-n-propyl-3,4,4a,5,10,10a-hexahydro-2H-naphtho[2,3-b][1,4]oxazine

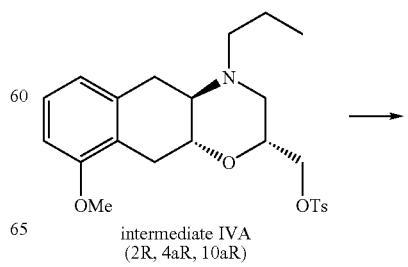
intermediate IVA
(2R, 4aR, 10aR)

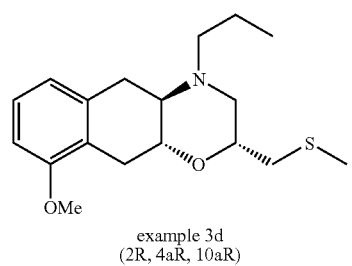

example 3d
(2R, 4aR, 10aR)

S-Methylisothiourea sulfate (25 mg) was added to a stirred suspension of KOH (20 mg) in MeOH (0.6 mL). The mixture was stirred for 10 min at rt and intermediate IVA (21 mg) was added. The solution was stirred at 65° C. for 3 h. After cooling to rt, 1,2-DCE (4 mL) was added, and the organic phase was washed with water (2 mL), dried (MgSO$_4$), and concentrated in vacuo. The crude product was purified by HPLC. Yield: 5 mg of example 3d as a clear oil. LC/MS (method 101): RT 0.84 min, ELSD 100%, UV 70%. MH$^+$: 322.1

3e. (2R,4aR,10aR)-2-Imidazol-1-ylmethyl-9-methoxy-4-n-propyl-3,4,4a,5,10,10a-hexahydro-2H-naphtho[2,3-b][1,4]oxazine

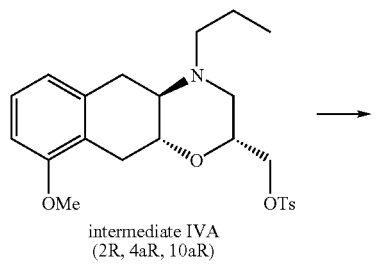

intermediate IVA
(2R, 4aR, 10aR)

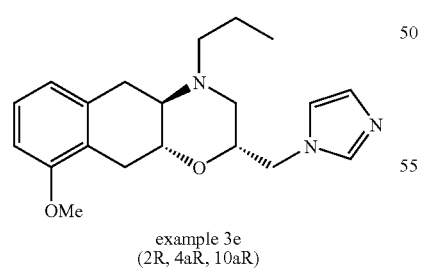

example 3e
(2R, 4aR, 10aR)

The procedure described for example 3a was followed starting from intermediate IVA (21 mg) and imidazole (11 mg) to give example 3e. Yield: 10 mg. LC/S (method 111): RT 0.49 min, ELSD 100%, UV 79%. MH$^+$: 342.3.

3f. (2R,4aR,10aR)-9-Methoxy-2-methoxymethyl-4-n-propyl-3,4,4a,5,10,10a-hexahydro-2H-naphtho[2,3-b][1,4]oxazine

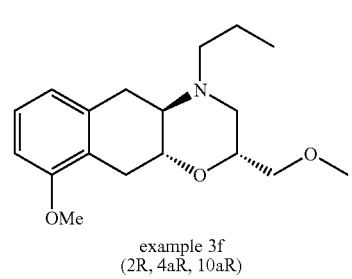

intermediate IVA
(2R, 4aR, 10aR)

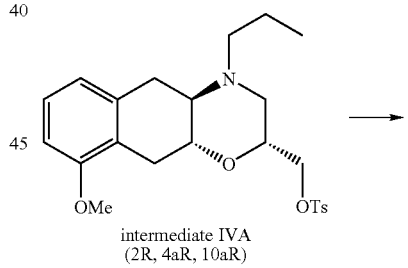

example 3f
(2R, 4aR, 10aR)

Sodium methoxide (5 M in MEOH, 0.1 mL) is added to a stirred solution of intermediate IVA (11 mg) in MeOH (0.4 mL). The solution is heated to 100° C. for 15 minutes in a sealed microwave process vial. After cooling to rt, EtOAc (1 mL) is added, and the organic phase is washed with brine (0.5 mL). The phases are separated and the crude product is purified by chromatography.

3g. ((2S,4aR,10aR)-9-Methoxy-4-n-propyl-3,4,4a,5,10,10a-hexahydro-2H-naphtho[2,3-b][1,4]oxazin-2-ylmethyl)-dimethyl-amine

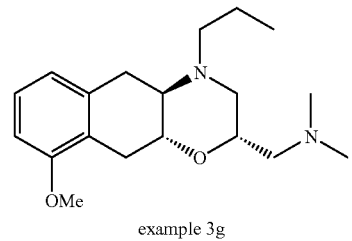

intermediate IVA
(2R, 4aR, 10aR)

example 3g
(2S, 4aR, 10aR)

Dimethylamine (0.1 mL, 8 M in MeOH) is added to a stirred solution of intermediate IVA (11 mg) in MeOH (0.4 mL). The solution is heated to 120° C. for 30 minutes in a sealed microwave process vial. After cooling to rt, EtOAc (1 mL) is added, and the organic phase is washed with brine (0.5 mL). The phases are separated and the crude product is purified by chromatography.

3h. (2R,4aR,10aR)-2-Fluoromethyl-9-methoxy-4-n-propyl-3,4,4a,5,10,10a-hexahydro-2H-naphtho[2,3-b][1,4]oxazine

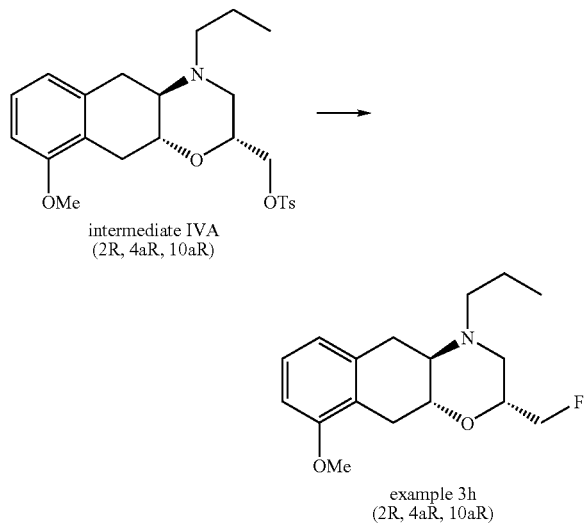

TBAF (1 M in THF, 0.5 mL) is added to intermediate IVA (11 mg). The solution is heated to 100° C. for 15 minutes in a sealed microwave process vial. After cooling to rt, EtOAc (1 mL) is added, and the organic phase is washed with brine (0.5 mL). The phases are separated and the crude product is purified by chromatography.

3i. (2S,4aR,10aR)-9-Methoxy-2-methyl-4-n-propyl-3,4,4a,5,10,10a-hexahydro-2H-naphtho[2,3b][1,4]oxazine

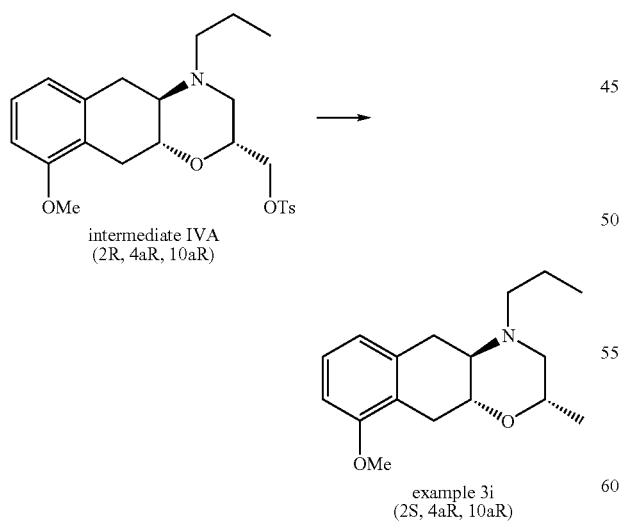

LAH (1M in THF, 0.5 mL) is added to a stirred solution of intermediate IVA (11 mg) in THF (0.5 mL). The solution is heated to 100° C. for 15 minutes in a sealed microwave process vial. After cooling to rt, EtOAc (1 mL) is added, and the organic phase is washed with brine (0.5 mL). The phases are separated and the crude product is purified by chromatography.

3j1. (2R,4aR,10aR)-9-Methoxy-4-n-propyl-2-pyrazol-1-ylmethyl-3,4,4a,5,10,10a-hexahydro-2H-naphtho[2,3-b][1,4]oxazine hydrochloride

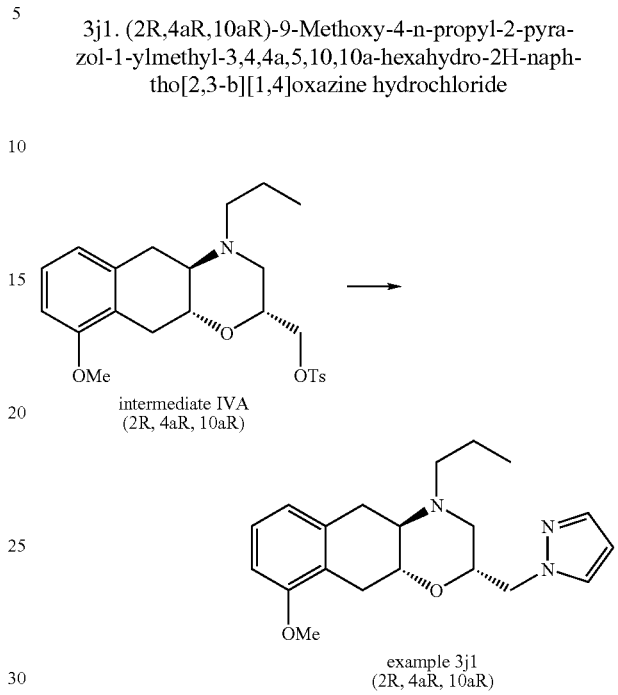

The procedure described for example 3a was followed starting from intermediate IVA (42 mg) and pyrazole (19 mg) to give example 3j1. HCl (2 mL, 2M in $Et_2O$) was added, and the volatiles components were removed in vacuo to deliver example 3j1 as a white solid. Yield: 20 mg. LC/MS (method 350): RT 0.41 min, ELSD 100%, UV 100%. $MH^+$: 342.1. Anal. Calcd for $C_{20}H_{28}N_3O_2Cl.2H_2O$: C, 58.00; H, 7.73; N, 10.14. Found: C, 58.47; H, 7.39; N, 10.04. $^1$H NMR (500MHz, DMSO) δ 0.95 (t, J=7.34 Hz, 3H), 1.63-1.81 (m, 2H), 2.39 (dd, J=16.71, J=10.83, 1H), 2.90-3.06 (mm, 2H), 3.07-3.19 (m, 2H), 3.30-3.40 (m, 3H), 3.48 (dd, J=16.03, J=5.34, 1H), 3.65 (s, 1H) 3.76 (s, 3H), 4.08-4.16 (m, 1H), 4.29 (dd, J=14.32, J=6.74, 1H), 4.39 (dd, J=14.32, J=4.29, 1H), 4.43-4.49 (m, 1H), 6.28 (t, J=2.04, 1H), 6.76 (d, J=7.93, 1H), 6.82 (d, J=8.21, 1H), 7.17 (t, J=8.00, 1H), 7.50 (d, J=1.89, 1H), 7.74 (d, J=2.23, 1H).

3j2. (2S,4aS,10aS)-9-Methoxy-4-n-propyl-2-pyrazol-1-ylmethyl-3,4,4a,5,10,10a-hexahydro-2H-naphtho[2,3-b][1,4]oxazine hydrochloride

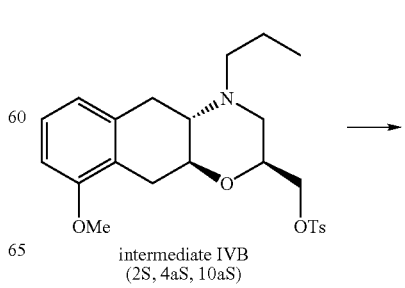

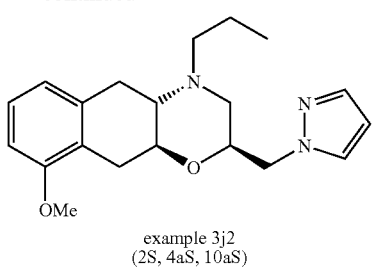

example 3j2
(2S, 4aS, 10aS)

The procedure described for example 3a was followed starting from intermediate IVB (42 mg, 0.09 mmol) and pyrazole (19 mg) to give example 3j2. HCl (2 mL, 2M in Et$_2$O) was added, and the volatiles components were removed in vacuo to deliver example 3j2 as a white solid. Yield: 16.1 mg. LC/MS (method 350): RT 0.41 min, ELSD 100%, UV 100%. MH$^+$: 342.1. Anal. Calcd for C$_{20}$H$_{28}$N$_3$O$_2$Cl.6H$_2$O: C, 49.40; H, 8.23; N, 8.64. Found: C, 49.13; H, 7.34; N, 8.46. $^1$H NMR data identical to the data reported for example 3j1.

3k1. (2S,4aR,10aR)-9-Methoxy-4-n-propyl-2-pyrazol-1-ylmethyl-3,4,4a,5,10,10a-hexahydro-2H-naphtho[2,3-b][1,4]oxazine hydrochloride

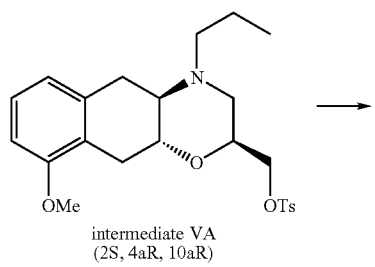

intermediate VA
(2S, 4aR, 10aR)

example 3k1
(2S, 4aR, 10aR)

The procedure described for example 3a was followed starting from intermediate VA (42 mg) and pyrazole (19 mg) to give example 3k1 as an oil. HCl (2 mL, 2M in Et$_2$O) was added, and the volatiles components were removed in vacuo to deliver example 3k1 as a white solid. Yield: 33 mg. LC/MS (method 350): RT 0.41 min, ELSD 100%, UV 100%. MH$^+$: 342.1. Anal. Calcd for C$_{20}$H$_{28}$N$_3$O$_2$Cl.3.5H$_2$O: C, 54.42; H, 7.90; N, 9.52. Found: C, 54.35; H, 7.57; N, 9.25. $^1$H NMR (500 MHz, DMSO) δ 0.95 (t, J=7.34 Hz, 3H), 1.67-1.82 (m, 2H), 2.33 (dd, J=16.80, J=10.21, 1H), 2.99-3.08 (mm, 2H), 3.32-3.52 (m, 7H), 3.77 (s, 3H), 4.35-4.42 (m, 1H), 4.44-4.51 (m, 1H), 4.69 (dd, J=14.29, J=6.06, 1H), 5.13 (dd, J=14.33, J=9.29, 1H), 6.27 (t, J=1.87, 1H), 6.78 (d, J=7.60, 1H), 6.82 (d, J=7.98, 1H), 7.18 (t, J=7.78, 1H), 7.50 (d, J=1.70, 1H), 7.92 (d, J=2.08, 1H).

3k2. (2R,4aS,10aS)-9-Methoxy-4-n-propyl-2-pyrazol-1-ylmethyl-3,4,4a,5,10,10a-hexahydro-2H-naphtho[2,3-b][1,4]oxazine hydrochloride

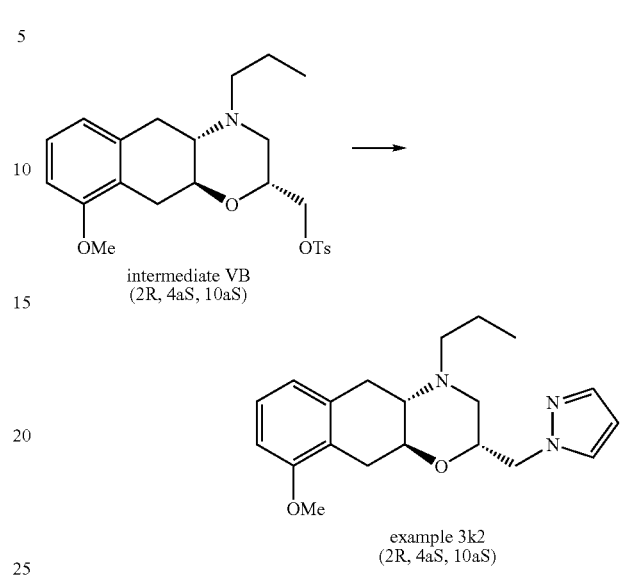

intermediate VB
(2R, 4aS, 10aS)

example 3k2
(2R, 4aS, 10aS)

The procedure described for example 3a was followed starting from intermediate VB (42 mg) and pyrazole (19 mg) to give example 3k2 as an oil. HCl (2 mL, 2M in Et$_2$O) was added, and the volatiles components were removed in vacuo to deliver example 3k2 as a white solid. Yield: 20 mg. LC/MS (method 350): RT 0.41 min, ELSD 100%, UV 100%. MH$^+$: 342.1. Anal. Calcd for C$_{20}$H$_{28}$N$_3$O$_2$Cl.2.5H$_2$O: C, 56.79; H, 7.88; N, 9.94. Found: C, 56.99; H, 7.49; N, 9.90. $^1$H NMR data identical to the data reported for example 3k1.

3l. (2R,4aR,10aR)-2-(4-Chloro-pyrazol-1-ylmethyl)-9-methoxy-4-n-propyl-3,4,4a,5,10,10a-hexahydro-2H-naphtho[2,3-b][1,4]oxazine

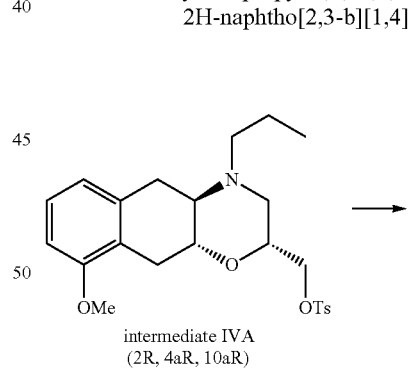

intermediate IVA
(2R, 4aR, 10aR)

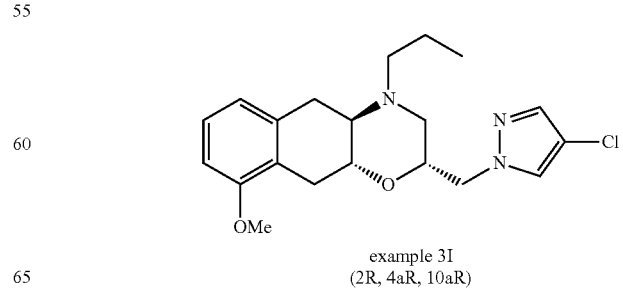

example 3l
(2R, 4aR, 10aR)

The procedure described for example 3a was followed starting from intermediate IVA (42 mg) and pyrazole (28 mg) to give 13 mg of example 3l as a white solid. LC/MS (method 350): RT 0.60 min, ELSD 100%, UV 100%. MH+: 376.3. $^1$H NMR (500 MHz, CDCl$_3$) δ 1.05 (t, J=7.20 Hz, 3H), 1.69-1.83 (m, 1H), 1.88-2.04 (m, 1H), 2.50 (dd, J=17.01, J=10.40, 1H), 2.57 (dd, J=18.94, J=9.44, 1H), 2.90 (bs, 2H), 3.21 (dd, J=15.56, J=4.75, 1H), 3.29 (t, J=11.30, 1H), 3.37 (dd, J=17.08, J=6.31, 1H), 3.54 (d, J=11.18, 1H), 3.67 (t, J=13.14, 1H), 3.84 (s, 3H), 4.29-4.41 (m, 2H), 4.55-4.66 (m, 1H), 4.91 (d, J=8.33, 1H), 6.69 (d, J=7.74, 1H), 6.72 (d, J=8.17, 1H), 6.82 (d, J=8.21, 1H), 7.15 (t, J=8.00, 1H), 7.44 (s, 1H), 7.52 (s, 1H). $^{13}$C NMR (500 MHz, CDCl$_3$) δ: 157.3 138.6, 132.3, 129.6, 128.0, 121.4, 121.0, 111.0, 108.4, 73.7, 70.6, 62.3, 55.8, 54.9, 54.6, 52.4, 30.1, 29.9, 16.4, 11.6.

3m. (2S,4aR,10aR)-2-(4-Chloro-pyrazol-1-ylmethyl)-9-methoxy-4-n-propyl-3,4,4a,5,10,10a-hexahydro-2H-naphtho[2,3-b][1,4]oxazine

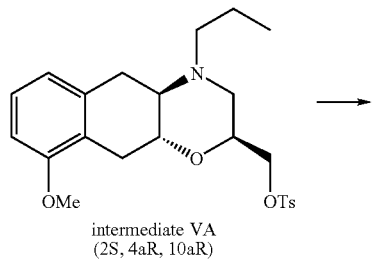

intermediate VA
(2S, 4aR, 10aR)

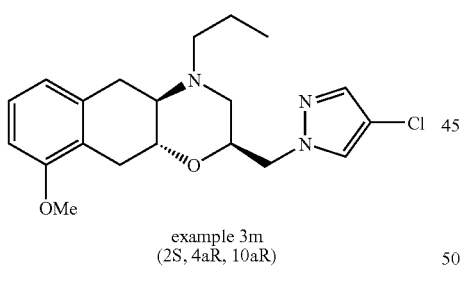

example 3m
(2S, 4aR, 10aR)

The procedure described for example 3a was followed starting from intermediate VA (42 mg) and pyrazole (28 mgl) to give example 3m as an oil. Yield: 43 mg. LC/MS (method 350): RT 0.58 min, ELSD 100%, UV 100%. MH+: 376.1.

$^1$H NMR (500 MHz, CDCl$_3$) δ 1.08 (bs, 3H), 1.73 (bs, 1H), 1.99 (bs, 1H), 2.51 (dd, J=9.25, J=16.47, 1H), 2.97-3.44 (m, 7H), 3.83 (s, 3H), 3.94 (m, 1H), 4.51 (bs, 1H), 4.80 (bs, 1H), 5.57 (bs, 1H), 6.72 (d, J=8.21, 2H), 7.17 (bs, 1H), 7.52 (s, 1H), 8.23 (s, 1H). $^{13}$C NMR (500 MHz, CDCl$_3$) δ: 157.3 138.3, 132.3, 131.2, 128.1, 121.2, 121.0, 110.9, 108.4, 69.5, 68.5, 62.9, 55.8, 55.5, 51.7, 49.2, 30.1, 29.8, 16.5, 11.8.

3n. (2R,4aR,10aR)-9-methoxy-2-(3-phenyl-pyrazol-1-ylmethyl)-4-n-propyl-3,4,4a,5,10,10a-hexahydro-2H-naphtho[2,3-b][1,4]oxazine

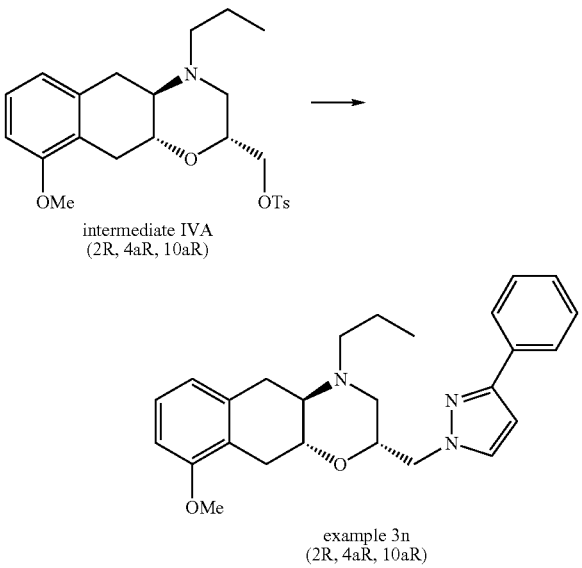

intermediate IVA
(2R, 4aR, 10aR)

example 3n
(2R, 4aR, 10aR)

The procedure described for example 3a was followed starting from intermediate IVA (42 mg) and 3-phenylpyrazole (39 mg) to give example 3n as an oil. Yield: 60 mg. LC/MS (method 350): RT 0.67 min, ELSD 99.9%, UV 71.5%. MH+: 418.1.

3o. (2S,4aR,10aR)-9-Methoxy-2-(3-phenyl-pyrazol-1-ylmethyl)-4-n-propyl-3,4,4a,5,10,10a-hexahydro-2H-naphtho[2,3-b][1,4]oxazine

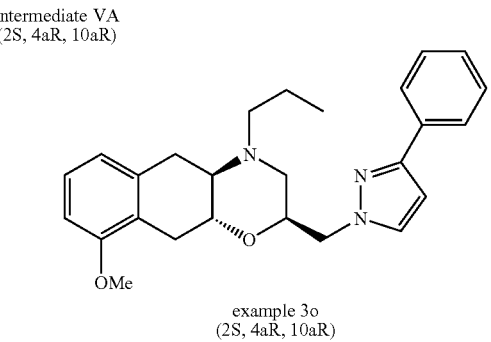

intermediate VA
(2S, 4aR, 10aR)

example 3o
(2S, 4aR, 10aR)

The procedure described for example 3a was followed starting from intermediate VA (42 mg) and 3-phenylpyrazole (39 mg) to give example 3o as an oil. Yield: 66 mg. LC/MS (method 350): RT 0.67 min, ELSD 91.9%, UV 79.7%. MH+: 418.1.

Example 4

4a1. (4aR,10aR)-4-Ethyl-3,4,4a,5,10,10a-hexahydro-2H-naphtho[2,3-b][1,4]oxazin-9-ol hydrochloride

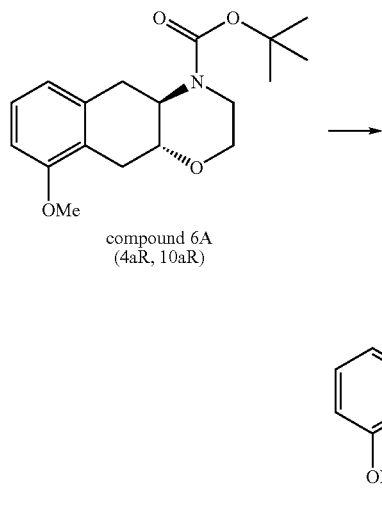

compound 6A
(4aR, 10aR)

example 4a1
(4aR, 10aR)

L-selectride (1M in THF, 18 mL) was added drop-wise at rt to a solution of compound 6A (577 mg) in THF (5 mL). The solution was heated to 100° C. for 6 h in a sealed microwave process vial. After cooling to 0° C., ice-cold water (125 mL) and sat. NaHCO$_3$ (50 mL) were slowly added, and the product was extracted with Et$_2$O (3×75 mL). The combined organic phases were washed with brine, dried (MgSO$_4$), and concentrated in vacuo. The residue was purified by silicagel chromatography to give (4aR,10aR)-9-hydroxy-2,3,4a,5,10,10a-hexahydro-naphtho[2,3-b][1,4]oxazine-4-carboxylic acid tert-butyl ester as a white solid. Yield: 297 mg. Mp: 203-205° C. 141 mg of this material was dissolved in MeOH (4 mL) and HCl (5 M in Et$_2$O) was added. The solution was stirred for 45 min at rt and concentrated in vacuo. The residue was dissolved in abs EtOH (2.3 mL). NaCNBH$_3$ (129 mg), acetic acid (0.3 mL) and acetaldehyde (122 mg) were added and the solution was heated to 90° C. for 15 min in a sealed microwave process vial. After cooling to 0° C., ice-cold water (25 mL) and sat. NaHCO$_3$ (10 mL) were slowly added, and the product was extracted with Et$_2$O (3×15 mL). The combined organic phases were washed with brine, dried (MgSO$_4$), and concentrated in vacuo. The crude product was purified by chromatography to give 49 mg. The product was dissolved in MeOH (1 mL) and HCl (1.5 mL, 5M in Et$_2$O) was added. The generated HCl salt was isolated and dried in vacuo. Yield of example 4a1: 38 mg as a white solid. mp dec.>280° C.; LC/MS (method 25): RT 0.66 min, ELSD 99%, UV 100%. MH+: 234.1. $^1$H NMR (500 MHz, DMSO) δ 1.25 (t, 3H), 2.40 (dd, 1H), 3.05-3.20 (br m, 4H), 3.35-3.50 (m, 3H), 4.00-4.10 (br m, 3H), 6.60 (d, 1H), 6.65 (d, 1H), 7.00 (t, 1H), 9.55 (s, 1H), 11.45-11.55 (b, 1H). Anal. Calcd for C$_{14}$H$_{19}$NO$_2$.HCl: C, 61.31; H, 7.53; N, 5.11. (¼H2O). Found: C, 61.69; H, 7.57; N, 5.12. α$_D$: −116.6 (C=0.5, DMSO).

4a2. (4aS,10aS)-4-Ethyl-3,4,4a,5,10,10a-hexahydro-2H-naphtho[2,3-b][1,4]oxazin-9-ol hydrochloride

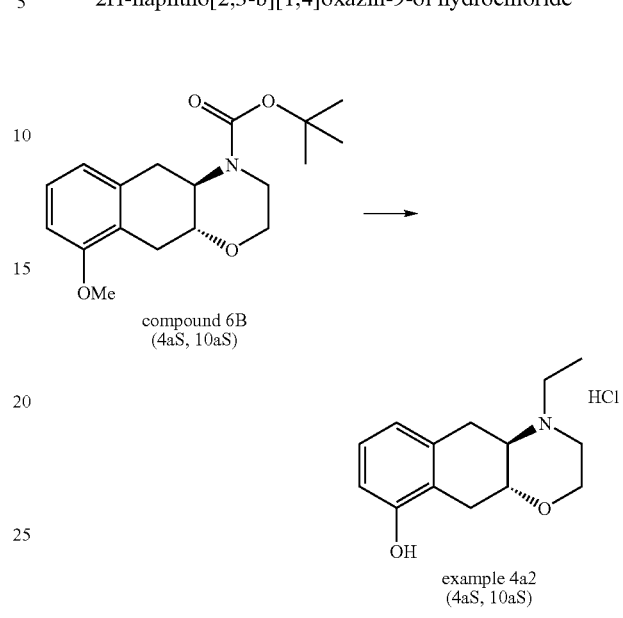

compound 6B
(4aS, 10aS)

example 4a2
(4aS, 10aS)

The procedure described for example 4a1 was followed starting from compound 6B (191 mg) to give example 4a2. Yield: 73 mg as a white solid. mp dec.>280° C.; LC/MS (method 25): RT 0.66 min, ELSD 99%, UV 100%. MH+: 234.1. $^1$H NMR data identical to the data reported for example 4a1. Anal. Calcd for C$_{14}$H$_{19}$NO$_2$.HCl: C, 61.31; H, 7.53; N, 5.11. Found: C, 61.97; H, 7.55; N, 5.13. α$_D$+122.2 (C=0.5, DMSO).

Example 5

5a1. (4aR,10aR)-4-Methyl-3,4,4a,5,10,10a-hexahydro-2H-naphtho[2,3-b][1,4]oxazin-9-ol hydrochloride

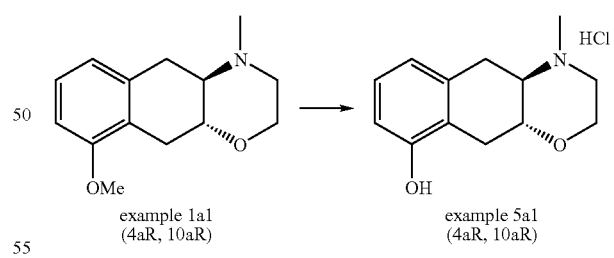

example 1a1
(4aR, 10aR)

example 5a1
(4aR, 10aR)

L-selectride (1M in THF, 4.6 mL) was added drop-wise at rt to example 1a1 (107 mg). The solution was heated to 100° C. for 6 h in a sealed microwave process vial. After cooling to 0° C., ice-cold water (25 mL) and sat. NaHCO$_3$ (10 mL) were slowly added, and the product was extracted with Et$_2$O (3×15 mL). The combined organic phases were washed with brine, dried (MgSO$_4$), and concentrated in vacuo. The crude product was purified by silicagel chromatography. The free base was dissolved in MeOH (1 mL) and precipitated as the HCl salt using 5M HCl in Et$_2$O (1.5 mL). Yield: 49 mg of example 5a1 as a white solid. Mp dec.>280° C.; LC/MS (method 25):

ELSD: 99.0%, UV: 100.0%, MH⁺: 220.3. ¹H NMR (500 MHz, DMSO) δ 2.40 (dd, 1H), 2.85 (s, 3H), 3.05-3.20 (br m, 2H), 3.25 (m, 1H), 3.35-3.50 (br m, 2H), 3.95-4.05 (br m, 3H), 6.60 (d, 1H), 6.65 (d, 1H), 7.00 (t, 1H), 9.55 (s, 1H), 11.30-11.40 (b, 1H). Anal. Calcd for $C_{13}H_{17}NO_2 \cdot HCl$: C, 61.05; H, 7.09; N, 5.48. Found: C, 60.46; H, 7.18; N, 5.28. $\alpha_D$-122.9 (C=0.5, DMSO).

5a2. (4aS,10aS)-4-Methyl-3,4,4a,5,10,10a-hexahydro-2H-naphtho[2,3-b][1,4]oxazin-9-ol hydrochloride

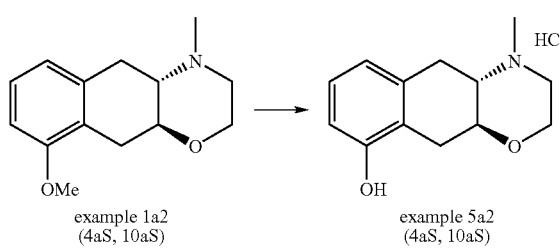

example 1a2
(4aS, 10aS)

example 5a2
(4aS, 10aS)

The procedure described for example 5a1 was followed starting from example 1a2 (78 mg) to give example 5a2. Yield: 50 mg as a white solid. mp dec.>280° C.; LC/MS (method 25): RT 0.56 min, ELSD 99%, UV 100%. MH⁺: 220.2. ¹H NMR data identical to the data reported for example 5a1. Anal. Calcd for $C_{14}H_{19}NO_2 \cdot HCl$: C, 61.05; H, 7.09; N, 5.48. Found: C, 60.49; H, 7.16; N, 5.31. $\alpha_D$+117 (C=0.5, DMSO).

5b1. (4aR,10aR)-4-n-Propyl-3,4,4a,5,10,10a-hexahydro-2H-naphtho[2,3-b][1,4]oxazin-9-ol hydrochloride

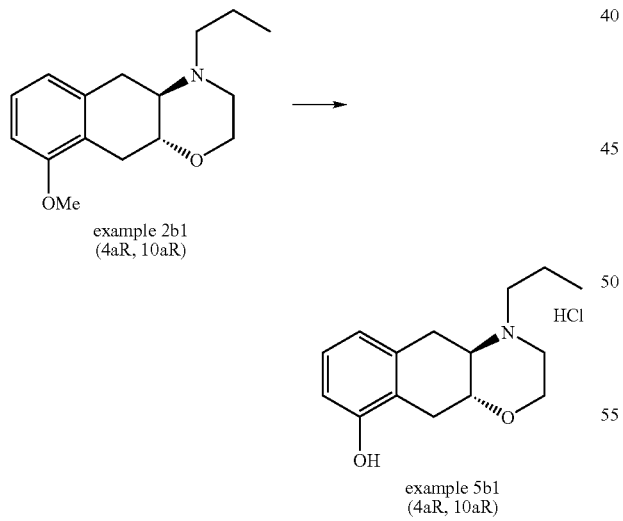

example 2b1
(4aR, 10aR)

example 5b1
(4aR, 10aR)

The procedure described for example 5a1 was followed starting from example 2b1 (102 mg) to give example 5b1. Yield: 61 mg as a white solid. mp dec.>300° C.; LC/MS (method 25): RT 0.56 min, ELSD 100%, UV 98%. MH⁺: 248.2. ¹H NMR (500 MHz, DMSO) δ 0.95 (t, 3H), 1.73 (m, 2H), 2.40 (dd, 1H), 3.00 (m, 1H), 3.10-3.20 (br m, 4H), 3.35-3.50 (br m, 2H), 4.05 (m, 3H), 6.60 (d, 1H), 6.65 (d, 1H), 7.00 (t, 1H), 9.55 (s, 1H), 11.30-11.40 (b, 1H); Anal. Calcd for $C_{15}H_{21}NO_2 \cdot HCl \cdot 0.25H_2O$: C, 62.48; H, 7.88; N, 4.86. Found: C, 62.71; H, 7.99; N, 5.05. $\alpha_D$-109.3 (C=0.5, DMSO).

5b2. (4aS,10aS)-4-n-Propyl-3,4,4a,5,10,10a-hexahydro-2H-naphtho[2,3-b][1,4]oxazin-9-ol hydrochloride

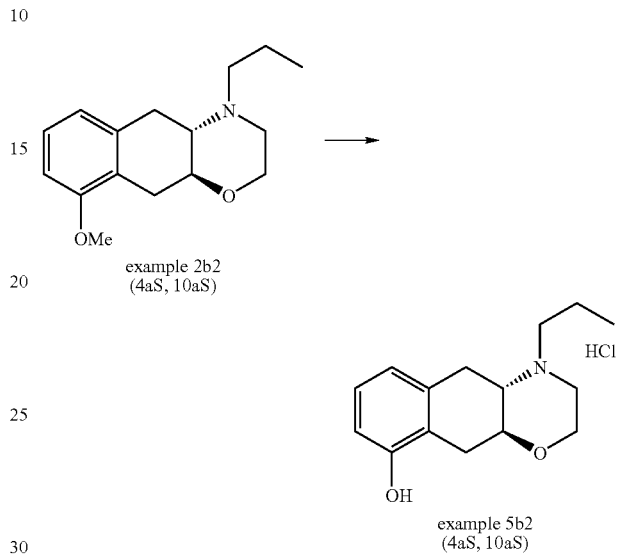

example 2b2
(4aS, 10aS)

example 5b2
(4aS, 10aS)

The procedure described for example 5a1 was followed starting from example 2b2 (102 mg) to give example 5b2. Yield: 60 mg as a white solid. mp dec.>300° C.; ¹H NMR data identical to the data reported for example 5b1. Anal. Calcd for $C_{15}H_{21}NO_2 \cdot HCl \cdot 0.25H_2O$: C, 62.48; H, 7.88; N, 4.86. Found: C, 62.67; H, 7.78; N, 5.00. $\alpha_D$+111.4 (C=0.5, DMSO).

5c1. (4aR,10aR)-4-Allyl-3,4,4a,5,10,10a-hexahydro-2H-naphtho[2,3-b][1,4]oxazin-9-ol hydrochloride

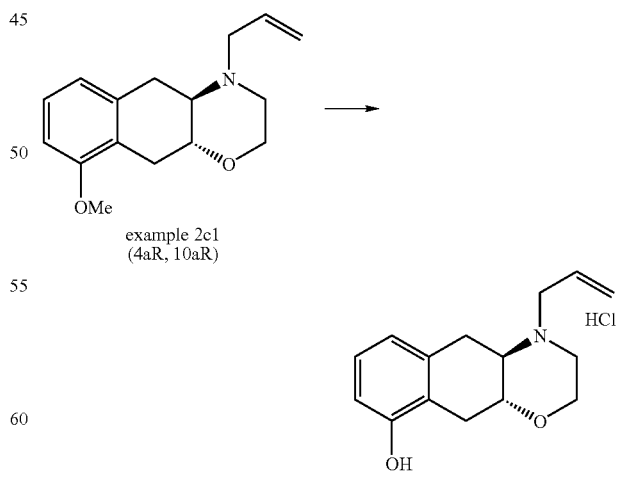

example 2c1
(4aR, 10aR)

example 5c1
(4aR, 10aR)

The procedure described for example 5a1 was followed starting from example 2c1 (117 mg) to give example 5e1.

Yield: 28 mg as a white solid. mp dec.>280° C.; LC/MS (method 25): RT 0.74 min, ELSD 99%, UV 96%. MH+: 246.2. ¹H NMR (500 MHz, DMSO) δ 2.40 (dd, 1H), 3.10-3.20 (br m, 3H), 3.40 (m, 1H), 3.45 (dd, 1H), 3.75 (m, 1H), 4.00-4.10 (br m, 4H), 5.55 (d, 1H), 5.65 (d, 1H), 6.05 (m, 1H), 6.60 (d, 1H), 6.65 (d, 1H), 7.00 (t, 1H), 9.55 (s, 1H), 11.65-11.75 (b, 1H). Anal. Calcd for $C_{15}H_{19}NO_2 \cdot HCl \cdot 0.25H_2O$: C, 62.93; H, 7.22; N, 4.89. Found: C, 62.53; H, 7.48; N, 4.71. $\alpha_D$ −115.4 (C=0.5, DMSO).

5c2. (4aS,10aS)-4-Allyl-3,4,4a,5,10,10a-hexahydro-2H-naphtho[2,3-b][1,4]oxazin-9-ol hydrochloride

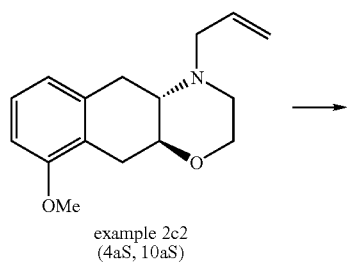

example 2c2
(4aS, 10aS)

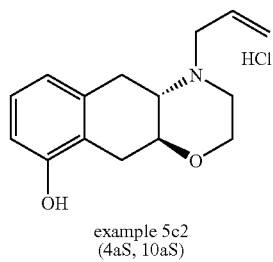

example 5c2
(4aS, 10aS)

The procedure described for example 5a1 was followed starting from example 2c2 (117 mg) to give example 5c2. Yield: 22 mg as a white solid. mp dec.>280° C.; LC/MS (method 25): RT 0.75 min, ELSD 99%, WV 95%. MH+: 246.3. ¹H NMR data identical to the data reported for example 5c1. Anal. Calcd for $C_{15}H_{21}NO_2 \cdot HCl \cdot 0.25H_2O$: C, 61.96; H, 7.28; N, 4.82. Found: C, 62.26; H, 7.51; N, 4.57. $\alpha_D$+118.4 (C=0.5, DMSO).

5d1. (4aR,10aR)-4-cyclo-Propylmethyl-3,4,4a,5,10,10a-hexahydro-2H-naphtho[2,3b][1,4]oxazin-9-ol hydrochloride

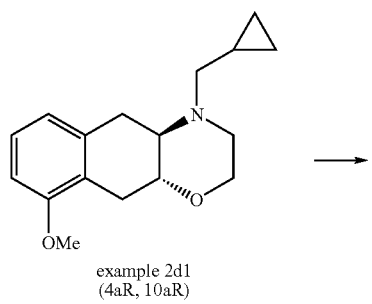

example 2d1
(4aR, 10aR)

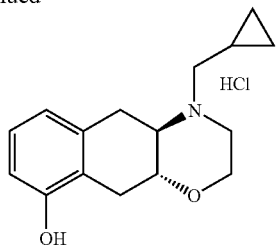

example 5d1
(4aR, 10aR)

The procedure described for example 5a1 was followed starting from example 2d1 (107 mg) to give example 5d1. Yield: 79 mg as a white solid. mp dec.>280° C.; LC/MS (method 25): RT 0.80 min, ELSD 99%, UV 98%. MH+: 260.2. ¹H NMR (500 MHz, DMSO) δ 0.45 (m, 2H), 0.65 (m, 2H), 1.15 (m, 1H), 2.40 (dd, 1H), 3.05-3.20 (br m, 3H), 3.25 (m, 1H), 3.35-3.45 (br m, 2H), 3.70 (d, 1H), 4.00-4.10 (br m, 3H), 6.60 (d, 1H), 6.65 (d, 1H), 7.00 (t, 1H), 9.55 (s, 1H), 11.10-11.20 (b, 1H). $\alpha_D$−109.5 (C=0.5, DMSO).

5d2. (4aS,10aS)-4-cyclo-Propylmethyl-3,4,4a,5,10,10a-hexahydro-2H-naphtho[2,3-b][1,4]oxazin-9-ol hydrochloride

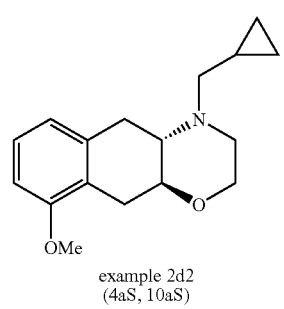

example 2d2
(4aS, 10aS)

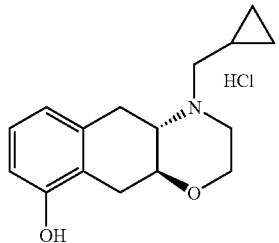

example 5d2
(4aS, 10aS)

The procedure described for example 5a1 was followed starting from example 2d2 (107 mg) to give example 5d2. Yield: 73 mg as a white solid. mp dec.>280° C.; LC/MS (method 25): RT 0.77 min, ELSD 99%, UV 96%. MH+: 260.2. ¹H NMR data identical to the data reported for example 5d1. Anal. Calcd for $C_{16}H_{21}NO_2 \cdot HCl$: C, 64,48; H, 7.52; N, 4.70. (⅛ H₂O). Found C, 64.32; H, 7.66; N, 4.64. $\alpha_D$+114.9 (C=0.5, DMSO).

The compound of Example 5d2 was subjected to X-ray analysis in order to determine the absolute configuration of the two stereocenters (cf. FIG. 1).

5e1. (2R,4aR,10aR)-2-Hydroxymethyl-4-n-propyl-3,4,4a,5,10,10a-hexahydro-2H-naphtho[2,3-b][1,4]oxazin-9-ol trifluoroacetate

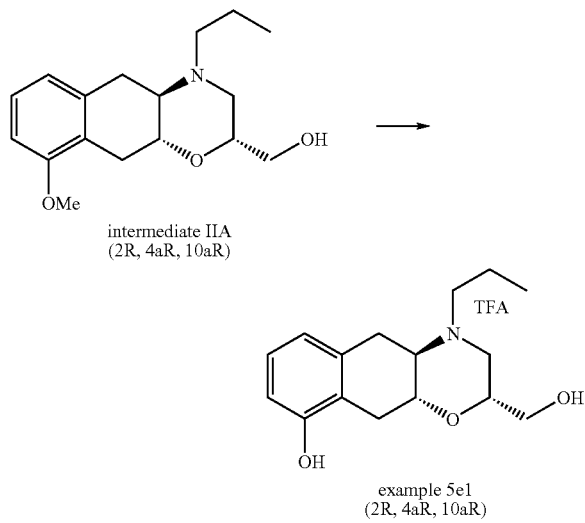

L-selectride (1M in THF, 0.75 mL) was added to intermediate IIA (20 mg). The solution was heated to 120° C. for 8 h in a sealed microwave process vial. After cooling to rt, ice-cold water (0.3 mL) and sat. NaHCO₃ (1 mL) were slowly added. The pH of the solution was adjusted to ~8.5 with dilute HCl. The product was extracted into 1,2-DCE (2×5 mL). The combined organic phases were washed with brine, and concentrated in vacuo. The crude product was purified by silica-gel chromatography (o-30% MeOH in EtOAc), and further by HPLC. Yield of 5e1: 3.7 mg as a clear oil. LC/MS (method 101): RT 0.47 min ELSD: 100%, UV: 96%, MH⁺=278.2.

5e2. (2S,4aS,10aS)-2-Hydroxymethyl-4-n-propyl-3,4,4a,5,10,10a-hexahydro-2H-naphtho[2,3-b][1,4]oxazin-9-ol trifluoroacetate

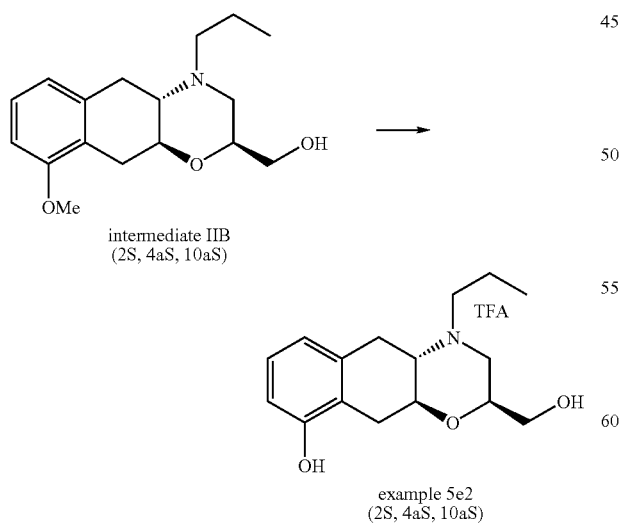

The procedure described for example 5e1 was followed starting from intermediate IB (12 mg) to give example 5e2. Yield: 5.0 mg as a clear oil. LC/MS (method 101): RT 0.47 min, ELSD 98%, UV 92%. MH⁺=278.2.

5f1. (2S,4aR,10aR)-2-Hydroxymethyl-4-n-propyl-3,4,4a,5,10,10a-hexahydro-2H-naphtho[2,3-b][1,4]oxazin-9-ol trifluoroacetate

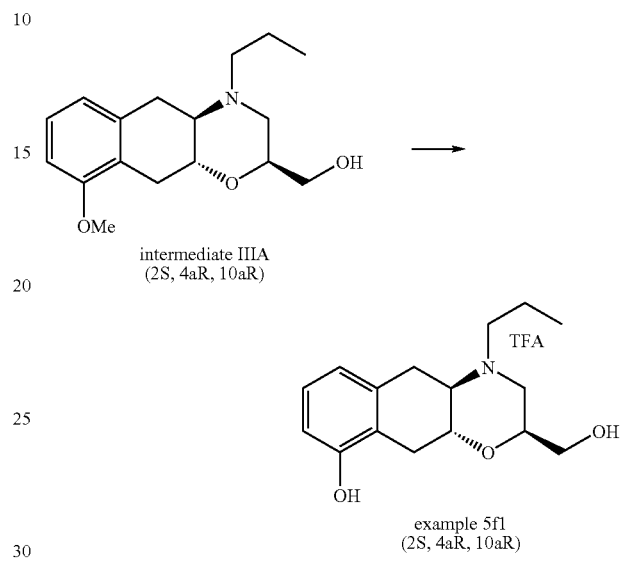

The procedure described for example 5e1 was followed starting from intermediate IIIA (25 mg) to give example 5f1. Yield: 5.8 mg as a clear oil. LC/MS (method 101): RT 0.47 min, ELSD 100%, UV 92%. MH⁺=278.2.

5f2. (2R,4aS,10aS)-2-Hydroxymethyl-4-n-propyl-3,4,4a,5,10,10a-hexahydro-2H-naphtho[2,3-b][1,4]oxazin-9-ol trifluoroacetate

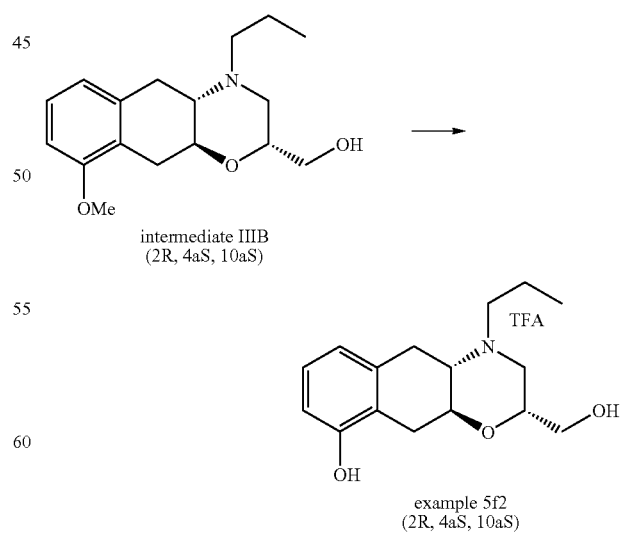

The procedure described for example 5e1 was followed starting from intermediate IIIB (25 mg) to give example 5f2.

Yield: 4.3 mg as a clear oil. LC/MS (method 101): RT 0.47 min, ELSD 100%, UV 88%. MH+=278.2.

5g. (2S,4aR,10aR)-4-n-Propyl-2-[1,2,4]triazol-1-ylmethyl-3,4,4a,5,10,10a-2H-naphtho[2,3-b][1,4]oxazin-9-ol trifluoroacetate

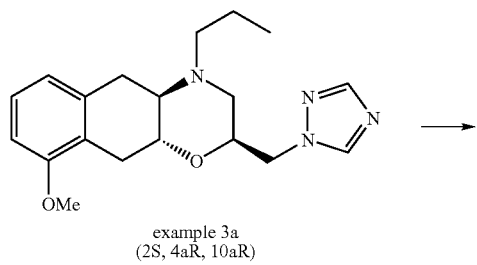

example 3a
(2S, 4aR, 10aR)

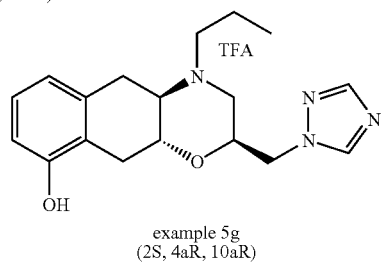

example 5g
(2S, 4aR, 10aR)

L-selectride (1M in THF, 1 mL) was added to example 3a (6 mg). The solution was heated to 100° C. for 6 h in a sealed microwave process vial. After cooling to rt, a small amount of wet Na$_2$SO$_4$ was slowly added. The solution was diluted by THF (2 mL) and filtered through dry Na$_2$SO$_4$. The solvent was evaporated off, and the residue was purified by HPLC. Yield of example 5g: 4.3 mg as a clear oil. LC/MS (method 101): RT=0.43 min. ELSD: 100%, UV: 93%, MH+=329.4.

5h. (2R,4aR,10aR)-4-n-Propyl-2-[1,2,4]triazol-1-ylmethyl-3,4,4a,5,10,10a-hexahydro-2H-naphtho[2,3-b][1,4]oxazin-9-ol trifluoroacetate

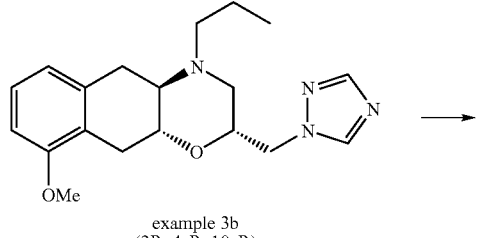

example 3b
(2R, 4aR, 10aR)

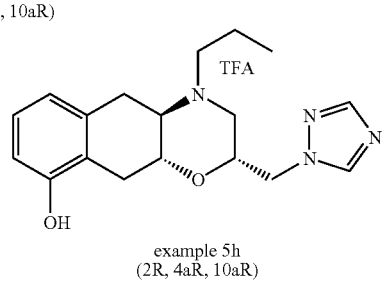

example 5h
(2R, 4aR, 10aR)

The procedure described for example 5g was followed starting from example 3b (12 mg) to give example 5h. Yield: 1.7 mg as a white oil. LC/MS (method 111): RT 0.44 min, ELSD 100%, UV 100%. MH+=329.5.

5i. (2S,4aR,10aR)-2-Methylsulfanylmethyl-4-n-propyl-3,4,4a,5,10,10a-hexahydro-2H-naphtho[2,3-b][1,4]oxazin-9-ol trifluoroacetate

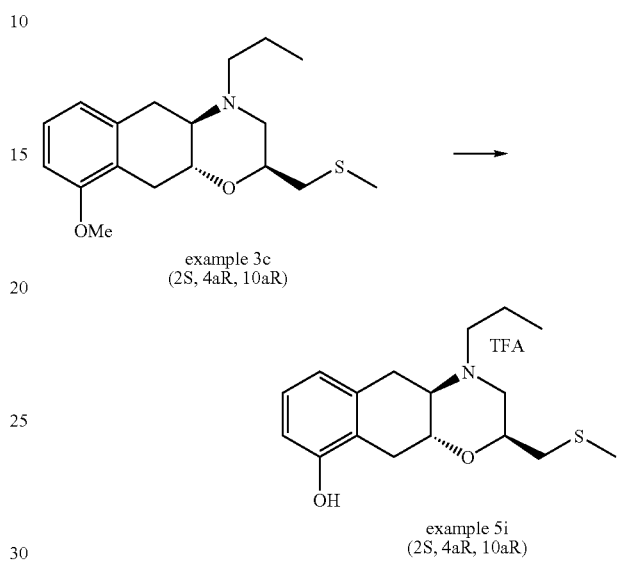

example 3c
(2S, 4aR, 10aR)

example 5i
(2S, 4aR, 10aR)

Example 5i can be prepared from example 3c using the method described for the preparation of example 5g.

5j. (2R,4aR,10aR)-2-methylsulfanylmethyl-4-n-propyl-3,4,4a,5,10,10a-hexahydro-2H-naphtho[2,3-b][1,4]oxazin-9-ol trifluoroacetate

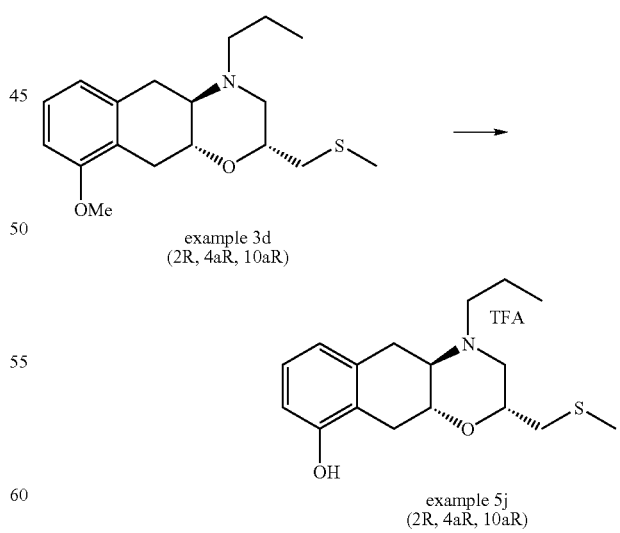

example 3d
(2R, 4aR, 10aR)

example 5j
(2R, 4aR, 10aR)

The procedure described for example 5g was followed starting from example 3d (2.3 mg) to give example 5j. Yield: 0.8 mg as a clear oil. LC/MS (method 350): RT 0.43 min, ELSD 100%, UV 100%. MH+=308.3.

The compound of Example 5j hydrochloride was subjected to X-ray analysis in order to determine the absolute configuration of the two stereocenters (cf. FIG. 1).

5k. (2S,4aR,10aR)-2-Methyl-4-n-propyl-3,4,4a,5,10,10a-hexahydro-2H-naphtho[2,3-b][1,4]oxazin-9-ol trifluoroacetate

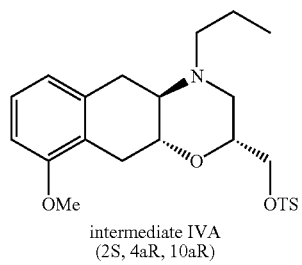

intermediate IVA
(2S, 4aR, 10aR)

→ example 5k
(2S, 4aR, 10aR)

The procedure described for example 5g was followed starting from intermediate IVA (3.9 mg) to give example 5k. Yield: 1.4 mg as a clear oil. LC/MS (method 111): RT 0.43 min, ELSD 84%, UV 62%. MH$^+$=262.1.

5l. (2R,4aR,10aR)-2-Imidazol-1-ylmethyl-4-n-propyl-3,4,4a,5,10,10a-hexahydro-2H-naphtho[2,3-b][1,4]oxazin-9-ol trifluoroacetate

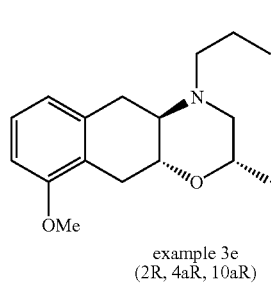

example 3e
(2R, 4aR, 10aR)

→ example 5l
(2R, 4aR, 10aR)

The procedure described for example 5g was followed starting from example 3e (10 mg) to give example 5l. Yield: 5.8 mg as a clear oil. LC/MS (method 350): RT 0.29 min, ELSD 100%, UV 100%. MH$^+$=328.0.

5m. (2R,4aR,10aR)-2-Methoxymethyl-4-n-propyl-3,4,4a,5,10,10a-hexahydro-2H-naphtho[2,3-b][1,4]oxazin-9-ol trifluoroacetate

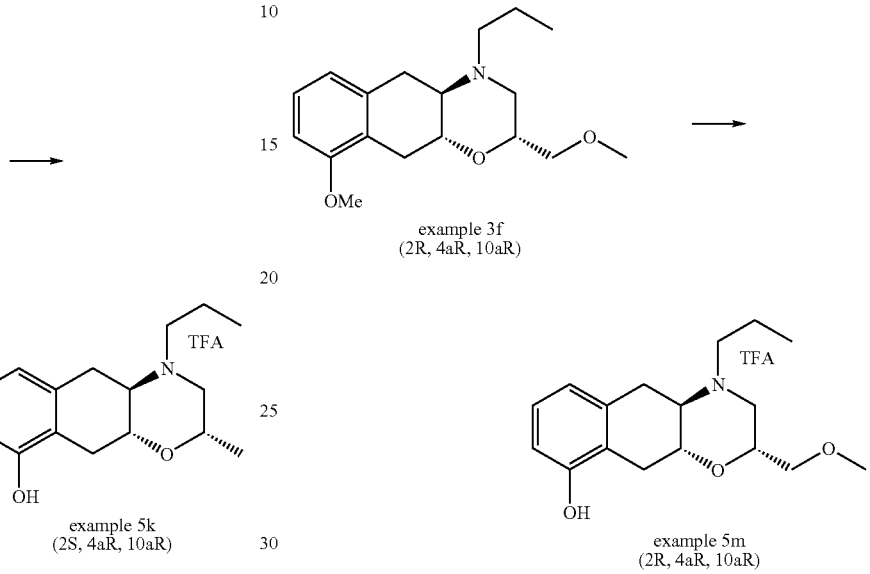

example 3f
(2R, 4aR, 10aR)

→ example 5m
(2R, 4aR, 10aR)

Example 5m can be prepared from example 3f using the method described for the preparation of example 5g.

5n. (2S,4aR,10aR)-2-Dimethylaminomethyl-4-n-propyl-3,4,4a,5,10,10a-hexahydro-2H-naphtho[2,3-b][1,4]oxazin-9-ol trifluoroacetate

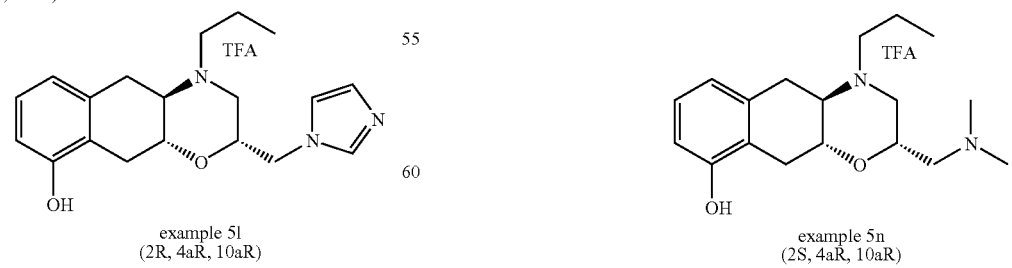

example 3g
(2S, 4aR, 10aR)

→ example 5n
(2S, 4aR, 10aR)

Example 5n can be prepared from example 3g using the method described for the preparation of example 5g.

5o. (2R,4aR,10aR)-2-Fluoromethyl-4-n-propyl-3,4,4a,5,10,10a-hexahydro-2H-naphtho[2,3-b][1,4]oxazin-9-ol trifluoroacetate

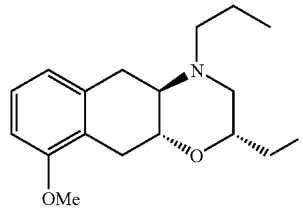

example 3h
(2R, 4aR, 10aR)

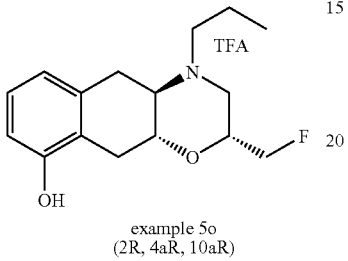

example 5o
(2R, 4aR, 10aR)

Example 5o can be prepared from example 3 h using the method described for the preparation of example 5g.

Example 6

6a1. (2R,4aR,10aR)-2-Pyrazol-1-ylmethyl-4-n-propyl-3,4,4a,5,10,10a-hexahydro-2H-naphtho[2,3-b][1,4]oxazin-9-ol trifluoroacetate

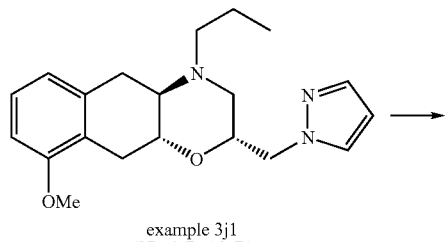

example 3j1
(2R, 4aR, 10aR)

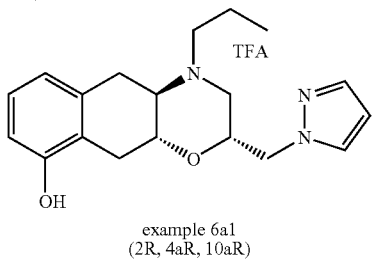

example 6a1
(2R, 4aR, 10aR)

Example 3j1 (27 mg, 0.08 mmol) was dissolved in DMA (2.5 mL) and KF (9 mg, 0.16 mmol) and thiophenol (0.04 mL, 0.40 mmol) were added. The solution was heated to 210° C. for 1 h in a sealed microwave process vial. After cooling to rt, the crude product was purified by silicagel chromatography (Eluent 0-100% EtOAc in heptane, 0-10% MeOH in EtOAc), and then by HPLC. Yield: 7.5 mg of 6a1 as an oil. LC/MS (method 350): RT 0.40 min, ELSD 99.9%, UV 100%. MH$^+$: 328.0. $^1$H NMR (500 MHz, DMSO) δ 0.96 (t, J=7.27 Hz, 3H), 1.54-1.67 (m, 1H), 1.70-1.82 (mn, 1H) 2.41 (dd, J=16.92, J=10.69, 1H), 2.51 (bs, 1H), 2.85 (t, J=13.90, 2H), 2.97-3.14 (mn, 2H), 3.34-3.71 (m, 3H), 3.92-3.99 (m, 1H), 4.25-4.42 (m, 3H), 6.29 (s, 1H), 6.60 (dd, J=7.45, 1H), 6.66 (d, J=7.66, 1H), 6.99 (t, J=7.89, 1H), 7.51 (s, 1H), 7.75 (d, J=1.53, 1H); HRMS C$_{19}$H$_{26}$N$_3$O$_2$ [M+H$^+$] calcd 328.2020. found 328.2011.

6a2. (2S,4aS,10aS)-2-Pyrazol-1-ylmethyl-4-n-propyl-3,4,4a,5,10,10a-hexahydro-2H-naphtho[2,3b][1,4]oxazin-9-ol trifluoroacetate

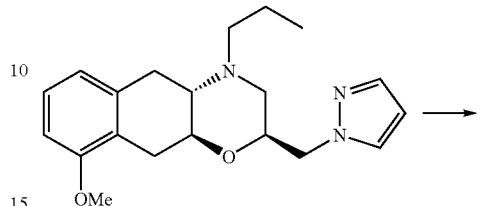

example 3j2
(2S, 4aS, 10aS)

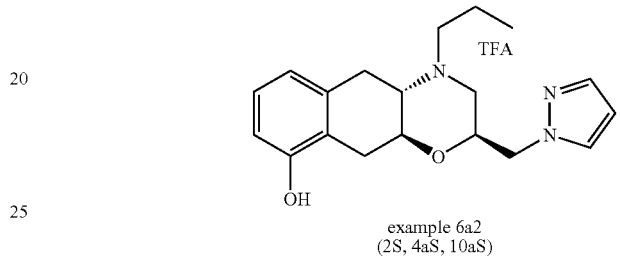

example 6a2
(2S, 4aS, 10aS)

The procedure described for example 6a1 was followed starting from example 3j2 to give example 6a2. Yield: 8.0 mg as an oil. LC/MS (method 350): RT 0.41 min, ELSD 100%, UV 100%. MH$^+$: 328.0. $^1$H NMR data identical to the data reported for example 6a1. HRMS C$_{19}$H$_{26}$N$_3$O$_2$ [M+H$^+$] calcd 328.2020. found 328.2020.

6b1. (2S,4aR,10aR)-2-Pyrazol-1-ylmethyl-4-n-propyl-3,4,4a,5,10,10a-hexahydro-2H-naphtho[2,3-b][1,4]oxazin-9-ol trifluoroacetate

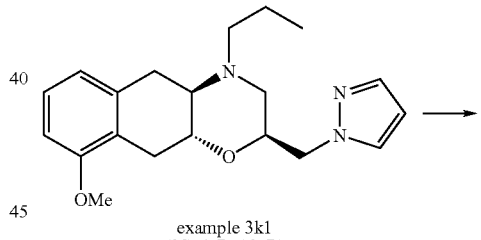

example 3k1
(2S, 4aR, 10aR)

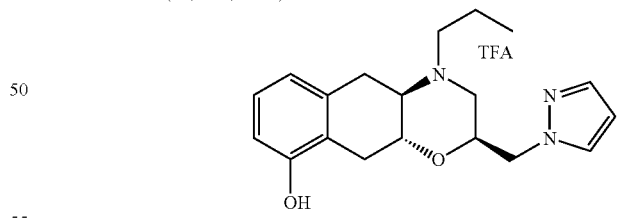

example 6b1
(2S, 4aR, 10aR)

The procedure described for example 6a1 was followed starting from example 3k1 to give example 6b1. Yield: 12 mg as an oil. LC/MS (method 350): RT 0.39 min, ELSD 99.4%, UV 100%. MH$^+$: 328.0. $^1$H NMR (500 MHz, DMSO) δ 0.77 (t, J=7.27 Hz, 3H), 1.41-1.62 (m, 2H), 2.14 (dd, J=16.67, J=10.24, 1H), 2.31 (bs, 1H), 2.77-2.94 (m, 3H), 3.19-3.32 (m, 4H), 3.38 (d, J=13.28, 3H), 4.15 (dd, J=16.23, J=10.05, 1H), 4.22-4.34 (m, 2H), 4.70 (dd, J=14.11, J=9.45 1H), 6.09 (s, 1H), 6.43 (dd, J=7.62, 1H), 6.48 (d, J=7.99, 1H), 6.81 (t, J=7.62, 1H), 7.31 (s, 1H), 7.63 (s, 1H); HRMS C$_{19}$H$_{26}$N$_3$O$_2$ [M+H$^+$] calcd 328.2020. found 328.2016.

6b2. (2R,4aS,10aS)-2-Pyrazol-1-ylmethyl-4-n-propyl-3,4,4a,5,10,10a-hexahydro-2H-naphtho[2,3-b][1,4]oxazin-9-ol trifluoroacetate

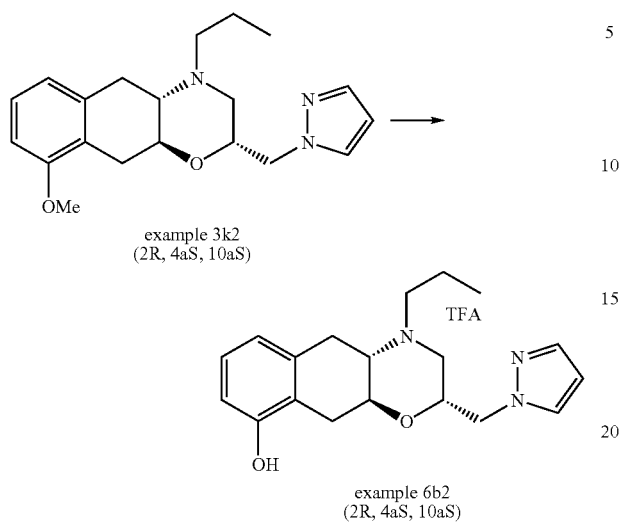

example 3k2
(2R, 4aS, 10aS)

example 6b2
(2R, 4aS, 10aS)

The procedure described for example 6b2 was followed starting from example 3k2 (40 mg) to give example 6b2. Yield: 7 mg as an oil. LC/MS (method 350): RT 0.40 min, ELSD 100%, UV 100%. MH$^+$: 328.0. $^1$H NMR data identical to the data reported for example 6a2. HRMS C$_{19}$H$_{26}$N$_3$O$_2$ [M+H$^+$] calcd 328.2020. found 328.2012.

6c. (2R,4aR,10aR)-2-(4-Chloro-pyrazol-1-ylmethyl)-4-n-propyl-3,4,4a,5,10,10a-hexahydro-2H-naphtho[2,3-b][1,4]oxazin-9-ol trifluoroacetate

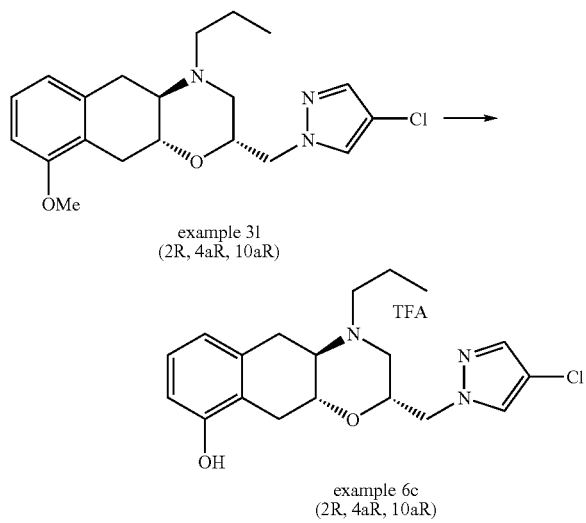

example 3l
(2R, 4aR, 10aR)

example 6c
(2R, 4aR, 10aR)

Example 3l (8 mg, 0.02 mmol) was dissolved in DMA (0.7 mL) and KF (2 mg, 0.04 mmol) and thiophenol (0.01 mL, 0.11 mmol) were added. The solution was heated to 220° C. for 1 h in a sealed microwave process vial. After cooling to rt, the solvent was evaporated off, and the residue was purified by silicagel chromatography and then by HPLC. Yield: 2.6 mg of example 6c as a white solid. LC/MS (method 350): RT 0.48 min, ELSD 100%, UV 100%. MH$^+$: 362.4. $^1$H NMR (500 MHz, DMSO) δ 0.95 (t, J=7.26 Hz, 3H), 1.55-1.68 (m, 1H), 1.69-1.81 (m, 2H), 2.40 (dd, J=16.60, J=10.62, 1H), 2.51 (bs, 1H), 2.82-3.05 (m, 2H), 3.10 (dd, J=16.71, J=5.83, 1H), 3.25-3.72 (m, 2H), 3.95 (d, J=5.99, 1H), (dd, J=15.78, J=10.27, 1H), 4.24-4.40 (m, 3H), 4.44-4.50 (m, 1H), 6.60 (d, J=7.67, 1H), 6.66 (d, J=7.67, 1H), 6.99 (t, J=7.82, 1H), 7.61 (s, 1H), 7.99 (s, 1H); 9.66 (bs, 1H). HRMS C$_{19}$H$_{25}$Cl$_1$N$_3$O$_2$ [M+H$^+$] calcd 362.1630. found 362.1628.

6d. (2S,4aR,10aR)-2-(4-Chloro-pyrazol-1-ylmethyl-4-n-propyl-3,4,4a,5,10,10a-hexahydro-2H-naphtho[2,3-b][1,4]oxazin-9-ol trifluoroacetate

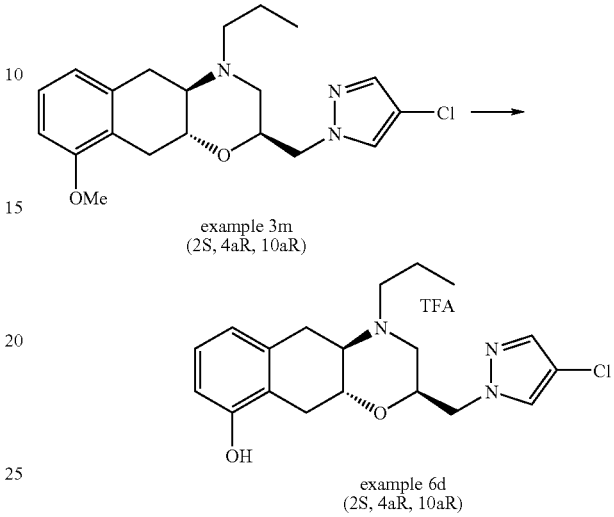

example 3m
(2S, 4aR, 10aR)

example 6d
(2S, 4aR, 10aR)

The procedure described for example 6c was followed starting from example 3m (26 mg) to give example 6d. Yield 6.4 mg of compound 6d as a white solid. LC/MS (method 350): RT 0.47 min, ELSD 100%, UV 100%. MH$^+$: 362.4. $^1$H NMR (500 MHz, DMSO) δ 0.96 (t, J=7.27 Hz, 3H), 1.57-1.81 (m, 2H), 2.32 (dd, J=16.32, J=10.42, 1H), 2.51 (bs, 1H), 2.93-3.06 (m, 3H), 3.42-3.60 (bs, 4H), 4.30 (dd, J=15.78, J=10.27, 1H), 4.39 (dd, J=14.50, J=4.50, 1H), 4.44-4.50 (m, 1H), 4.89 (dd, J=14.32, J=10.32 1H), 6.63 (d, J=7.67, 1H), 6.67 (d, J=7.67, 1H), 7.00 (t, J=7.82, 1H), 7.61 (s, 1H), 8.10 (s, 1H); 9.67 (bs, 1H). HRMS C$_{19}$H$_{25}$Cl$_1$N$_3$O$_2$ [M+H$^+$] calcd 362.1630. found 362.1624.

6e. (2R,4aR,10aR)-2-(3-Phenyl-pyrazol-1-ylmethyl)-4-n-propyl-3,4,4a,5,10, a-hexahydro-2H-naphtho[2,3-b][1,4]oxazin-9-ol trifluoroacetate

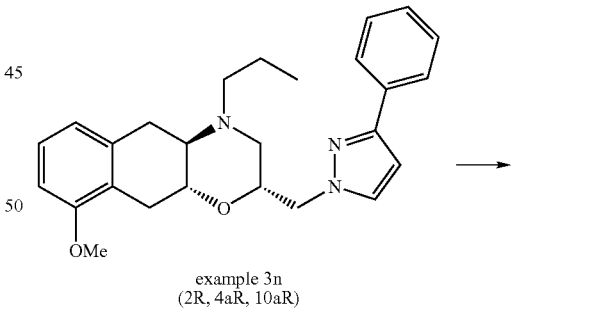

example 3n
(2R, 4aR, 10aR)

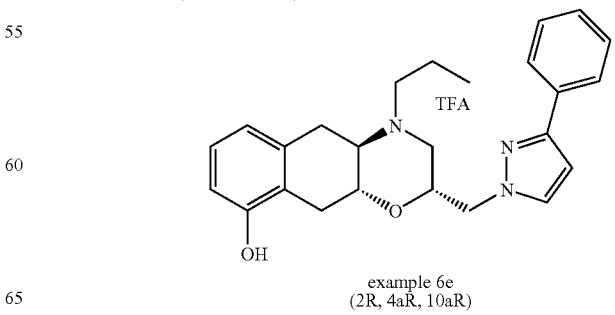

example 6e
(2R, 4aR, 10aR)

Example 3n (60 mg, 0.14 mmol) was dissolved in DMA (0.7 mL) and KF (16 mg, 0.28 mmol) and thiophenol (0.07 mL, 0.70 mmol) were added. The solution was heated to 220° C. for 1 h in a sealed microwave process vial. After cooling to rt, the solvent was evaporated off, and the residue was purified by chromatography (Eluent: 0-100% EtOAc in heptane), and then by HPLC. Yield: 15.6 mg of example 6e as oil. LC/MS (method 350): RT 0.57 min, ELSD 99.5%, UV 85.6%. MH+: 404.3. $^1$H NMR (500 MHz, DMSO) δ 0.79 (t, J=7.16 Hz, 3H), 1.57-1.69 (m, 1H), 1.70-1.84 (m, 1H), 2.44 (dd, J=16.74, J=10.37, 1H), 2.51 (bs, 2H), 2.55 (s, 1H), 2.87 (dd, J=14.88, J=12.08, 1H), 3.00-3.09 (m, 1H), 3.12 (dd, J=16.57, J=6.15, 1H) (s, 1H) 3.73 (d, J=12.23, 3H), 3.99 (m, 1H), 4.31-4.48 (m, 3H), 6.61 (d, J=7.60, 1H), 6.67 (d, J=8.00, 1H), 6.77 (d, J=2.13, 1H), 6.99 (t, J=7.74, 1H), 7.31 (t, J=7.27, 1H), 7.41 (t, J=7.55, 1H), 7.79-7.83 (m, 3H), 9.67 (bs, 1H). HRMS $C_{25}H_{30}N_3O_2$ [M+H+] calcd 404.2333. found 404.2339.

6f. (2S,4aR,10aR)-2-(4-Phenyl-pyrazol-1-ylmethyl)-4-n-propyl-3,4,4a,5,10,10a-hexahydro-2H-naphtho[2,3-b][1,4]oxazin-9-ol trifluoroacetate

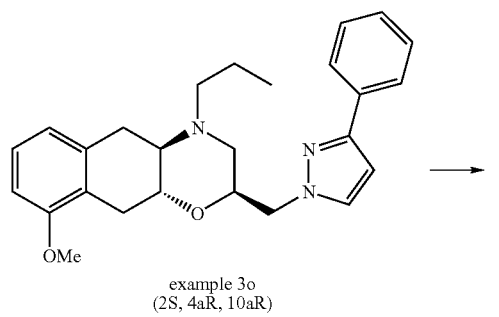

example 3o
(2S, 4aR, 10aR)

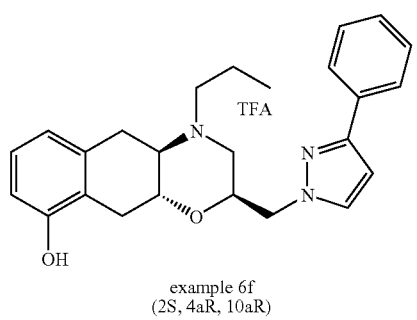

example 6f
(2S, 4aR, 10aR)

The procedure described for example 6e was followed starting from example 3o (66 mg) to give example 6f. Yield: 4.9 mg as an oil. LC/MS (method 350): RT 0.58 min, ELSD 100%, UV 88.7%. MH+: 404.3. $^1$H NMR (500 MHz, DMSO) δ 0.79 (t, J=7.22 Hz, 3H), 1.39-1.65 (m, 2H), 2.16 (dd, J=16.74, J=10.37, 1H), 2.32 (bs, 2H), 2.36 (s, 1H), 2.80-2.98 (m, 3H), 3.11-3.47 (m, 3H), 4.10-4.30 (m, 1H), 4.31-4.40 (m, 1H), 4.76 (dd, J=15.23, J=11.56 3.58, 1H), 6.45 (d, J=7.82, 1H), 6.49 (d, J=7.48, 1H), 6.57 (d, J=2.25, 1H), 6.82 (t, J=7.80, 1H), 7.12 (t, J=7.33, 1H), 7.22 (t, J=7.62, 2H), 7.62 (d, J=7.33, 2H), 7.73 (d, J=1.89, 1H), 9.43 (bs, 1H). HRMS $C_{25}H_{30}N_3O_2$ [M+H+] calcd 404.2333. found 404.2330.

Example 7

7 (4aR,10aR)-4-n-Propyl-3,4,4a,5,10,10a-hexahydro-2H-naphtho[2,3-b][1,4]oxazine-8,9-diol trifluoroacetate

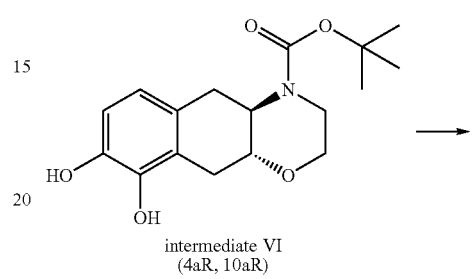

intermediate VI
(4aR, 10aR)

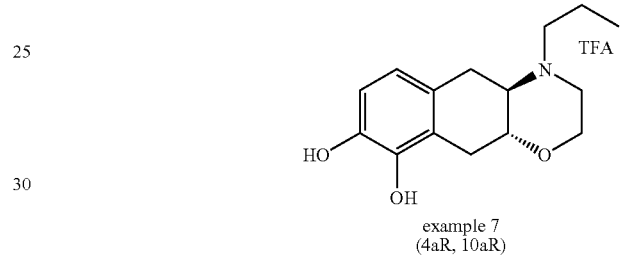

example 7
(4aR, 10aR)

To a stirred solution of intermediate VI (16 mg) in MeOH (1 mL) was added HCl (1.5 mL, 2M in Et$_2$O). The solution was stirred at rt for 15 min and then concentrated in vacuo. The residue was suspended in MeOH (1 mL). Propionaldehyde (18 mg), NaCNBH$_3$ (18 mg), and AcOH (1 drop) were added and the solution was stirred at rt 0.5 h. More NaCNBH$_3$ (18 mg) was added and the solution was gently heated 40° C. for 2 min. The crude mixture was concentrated in vacuo, and the residue was purified by HPLC. Yield of example 7: 4 mg as an oil. LC/MS (method 102): RT 0.59 min, ELSD 100%, UV 89.3%. MH+: 264.1.

Example 8

8a (6aR,10aR)-7-Methyl-6a,7,8,9,10a,11-hexahydro-6H-1,3,10-trioxa-7-aza-cyclopenta[a]anthracene trifluoroacetate

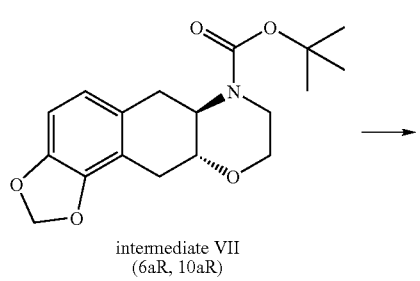

intermediate VII
(6aR, 10aR)

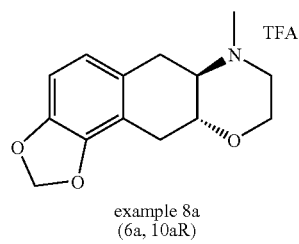

example 8a
(6a, 10aR)

LAH (1 mL, 1M in THF) was added to intermediate VII (9 mg) at rt, in a microwave reactor vial. The vial was sealed, and the mixture was stirred at 90° C. for 0.5 h under microwave irradiation. The reaction was quenched by the addition of wet $Na_2SO_4$. The suspension was filtered through dry $Na_2SO_4$. and filtrate was concentrated in vacuo. The residue was purified by HPLC. Yield of example 8a: 1.4 mg as an oil. LC/MS (method 102): RT 0.75 min, ELSD 100%, UV 90.6%. $MH^+$: 248.1.

8b (6aR,10aR)-7-Ethyl-6a,7,8,9,10a,11-hexahydro-6H-1,3,10-trioxa-7-aza-cyclopenta[a]anthracene trifluoroacetate

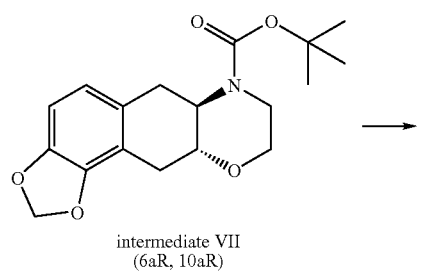

intermediate VII
(6aR, 10aR)

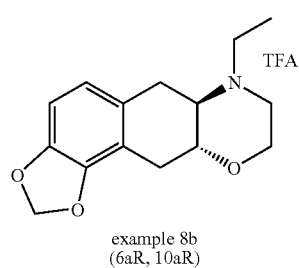

example 8b
(6aR, 10aR)

HCl (1.5 mL, 2M in $Et_2O$) was added to a stirred solution of intermediate VII (3 mg) in MeOH (1.5 mL). The solution was stirred at rt for 5 min, before it was concentrated in vacuo. The residue was dissolved in DMF (0.5 mL) and $K_2CO_3$ (22 mg) and iodoethane (30 micro-L) were added. The suspension was stirred at 70° C. for 0.25 h, and then poured into water (5 mL) and extracted with EtOAc (2×10 mL). The combined organic extracts were washed with brine, dried ($Na_2SO_4$). The crude mixture was concentrated in vacuo, and the residue was purified by HPLC. Yield of example 8b: 0.8 mg as an oil. LC/MS (method 101): RT 0.52 min, ELSD 100%, UV 90.0%, $MH^+$: 262.2.

8c (6aR,10aR)-7-n-Propyl-6a,7,8,9,10a,11-hexahydro-6H-1,3,10-trioxa-7-aza-cyclo-penta[a]anthracene trifluoroacetate

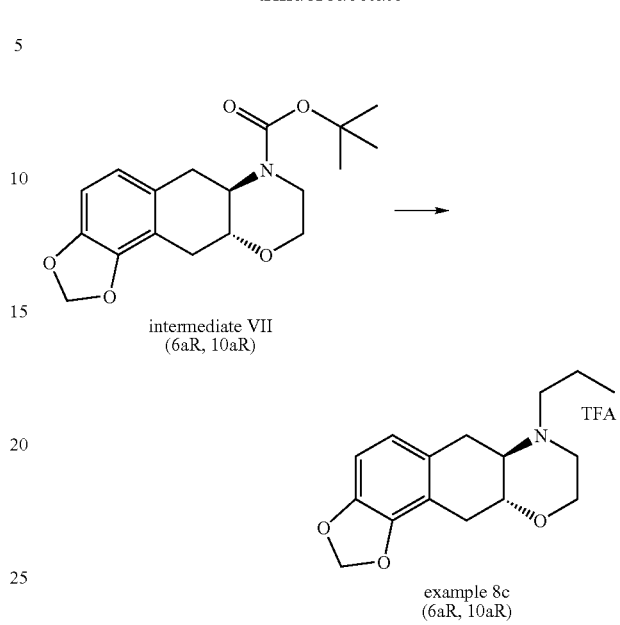

intermediate VII
(6aR, 10aR)

example 8c
(6aR, 10aR)

HCl (1.5 mL, 2M in $Et_2O$) was added to a stirred solution of intermediate VII (9 mg) in MeOH (1.5 mL). The solution was stirred at rt for 1.5 h, before it was concentrated in vacuo. The residue was dissolved in DMF (1 mL) and $K_2CO_3$ (45 mg) and 1-iodopropane (0.055 mL) were added. The suspension was stirred at 70° C. for 1 h, and then poured into water (5 mL) and extracted with EtOAc (2×10 mL). The combined organic layers were washed with brine, dried ($Na_2SO_4$), and concentrated in vacuo, and the residue was purified by HPLC. Yield of example 8c: 4.6 mg as a white solid. LC/MS (method 102): RT 0.92 min, ELSD 100%, UV 95.2%. $MH^+$: 276.3.

Abbreviations and List of Chemicals Used

The following abbreviations are used. This paragraph also outlines the chemicals used along with their commercial source (not included for standard solvents).

AcOH=acetic acid. Allyl bromide (e.g. Fluka 05870) $α_D$=specific optical rotation. $Boc_2O$=Boc anhydride/di-t-butyl dicarbonate (e.g. Aldrich 19,913-3). Brine=saturated aqueous solution of sodium chloride. BSA=bovine serum albumin. cAMP=cyclic adenosine monophosphate. $CH_2BrCl$=bromochloromethane (Aldrich 13,526-7). $CH_3I$=methyl iodide/iodomethane (e.g. Aldrich 28,956-6). CHO cell=Chinese hamster ovary cell. ClAcCl=chloroacethyl chloride (e.g. Aldrich 10,449-3). $Cs_2CO_3$=cesium carbonate (Aldrich 441902). cyclo-propyl methyl bromide/(bromomethyl)-cyclo-propane (Aldrich 24,240-3). DA=dopamine. D1=dopamine D1 receptor. D2=dopamine D2 receptor. D3=dopamine D3 receptor. D4=dopamine D4 receptor. D5=dopamine D5 receptor. DCM=dichloromethane/methylene chloride. DMF=dimethyl formamide. DMSO=dimethyl sulfoxide. L-DOPA=(levo)-3,4-dihydroxy phenylalanine. $EC_{50}$=concentration required to induce a response halfway between the baseline and the maximum response for the compound in question. ELSD=evaporative light scattering detection. $Et_3N$=triethyl amine. $Et_2NH$=diethyl amine. EtOAc=ethyl acetate. 99% EtOH=absolute ethanol. Ethyl magnesium bromide (used as a 3M solution in $Et_2O$; e.g.

Aldrich 18,987-1). Et$_2$O=diethyl ether. [(1-Ethoxy-cyclopropyl)-oxy]trimethylsilane (Aldrich 332739). 35% H$_2$O$_2$=35% aqueous solution of hydrogen peroxide (e.g. Aldrich 34,988-7). FSB=foetal bovine serum. h=hours. HCl=aqueous solution of hydrogen chloride (unless noted specifically as a Et$_2$O solution, which is commercially available, e.g. Aldrich 45,518-0). HMPA=hexamethylphosphorous triamide. HRMS=high-resolution mass spectrometry. i=iso. IBMX=3-i-butyl-1-methylxanthine. i.d.=inner diameter. 1-Iodopropane (e.g. Aldrich 17,188-3). K$_2$CO$_3$=potassium carbonate (e.g. Aldrich 20,961-9). KMnO$_4$=potassium permanganate (e.g. Aldrich 39,912-4). KO=knock-out. LC/MS=high-performance liquid chromatography/mass spectrometer. LAH=lithium aluminium hydride (used as a 1M THF solution; e.g. Aldrich 21,277-6). L-Selectride=lithium tri-s-butylborohydride (used as a 1M THF solution; Aldrich 17,849-7). MDO=methylene-di-oxy. MED=minimal effective dose. MED$_{Nemonapride}$=minimal effective dose in the presence of Nemonapride. MeOH=methanol. Methoxyacetyl chloride (e.g. Aldrich M965-3). min=minutes. MBD=minimal brain dysfunction. n=normal. NaCNBH$_3$=sodium cyanoborohydride (e.g. Aldrich 15,615-9). NaH=sodium hydride (used as a 60% dispersion; e.g. Aldrich 45,291-2). 1 M/9 M NaOH=1 M/9 M aqueous solution of sodium hydroxide. NaOMe=sodium methoxide (used as a ca. 5 M solution in methanol; e.g. Aldrich 15,625-6). 6-OHDA=6-hydroxy-dopamine. PBS=phosphate buffered saline (0.02 M sodium phosphate buffer with 0.15 M sodium chloride, pH adjusted to 7.4). PD=Parkinson's disease. PFC=prefrontal cortex. Pd/C=palladium-on-charcoal (e.g. Aldrich 20,569-9). PK=pharmacokinetic. PLMD=periodic limb movement disorder. Propionaldehyde (e.g. Aldrich 58,812-4). RLS=restless legs syndrome. rt=room temperature. RT=retention time. sat. NaHCO$_3$=saturated aqueous solution of sodium hydrogen carbonate. sat. NH$_4$Cl=saturated aqueous solution of ammonium chloride. SC=subcutaneous. SFC=supercritical flash chromatography. tert=tertiary. TBAI=tetra-n-butyl ammonium iodide (e.g. Aldrich 14,077-5). TFA=trifluoroacetic acid. THF=tetrahydrofuran (dried over 4 Å molecular sieves). UV=ultraviolet purity (at 254 nm unless noted differently).

Pharmacological Testing

D1 cAMP Assay

The ability of the compounds to either stimulate or inhibit the D1 receptor mediated cAMP formation in CHO cells stably expressing the human recombinant D1 receptor was measured as follows. Cells were seeded in 96-well plates at a concentration of 11000 cells/well 3 days prior to the experiment. On the day of the experiment the cells were washed once in preheated G buffer (1 mM MgCl$_2$, 0.9 mM CaCl$_2$, 1 mM IBMX (3-i-butyl-1-methylxanthine) in PBS (phosphate buffered saline)) and the assay was initiated by addition of 100 micro-L of a mixture of 30 nM A68930 and test compound diluted in G buffer (antagonism) or test compound diluted in G buffer (agonism). The cells were incubated for 20 minutes at 37° C. and the reaction was stopped by the addition of 100 micro-L S buffer (0.1 M HCl and 0.1 mM CaCl$_2$) and the plates were placed at 4° C. for 1 h. 68 micro-L N buffer (0.15 M NaOH and 60 mM NaOAc) was added and the plates were shaken for 10 minutes. 60 micro-1 of the reaction were transferred to cAMP FlashPlates (DuPont NEN) containing 40 micro-L 60 mM Sodium acetate pH 6.2 and 100 micro-L IC mix (50 mM Sodium acetate pH 6.2, 0.1% sodium azide, 12 mM CaCl$_2$ 1% BSA (bovine serum albumin) and 0.15 micro-Ci/mL $^{125}$I-cAMP) were added. Following an 18 h incubation at 4° C. the plates were washed once and counted in a Wallac TriLux counter.

D2 cAMP Assay

The ability of the compounds to either stimulate or inhibit the D2 receptor mediated inhibition of cAMP formation in CHO cells transfected with the human D2 receptor was measure as follows. Cells were seeded in 96 well plates at a concentration of 8000 cells/well 3 days prior to the experiment. On the day of the experiment the cells were washed once in preheated G buffer (1 mM MgCl$_2$, 0.9 mM CaCl$_2$, 1 mM IBMX in PBS) and the assay was initiated by addition of 100 micro-1 of a mixture of 1 micro-M quinpirole, 10 microM forskolin and test compound in G buffer (antagonism) or 10 micro-M forskolin and test compound in G buffer (agonism). The cells were incubated 20 minutes at 37° C. and the reaction was stopped by the addition of 100 micro-1 S buffer (0.1 M HCl and 0.1 mM CaCl$_2$) and the plates were placed at 4° C. for 1 h. 68 micro-L N buffer (0.15 M NaOH and 60 mM Sodium acetate) were added and the plates were shaken for 10 minutes. 60 micro-L of the reaction were transferred to cAMP FlashPlates (DuPont NEN) containing 40 micro-L 60 mM NaOAc pH 6.2 and 100 micro-L IC mix (50 mM NaOAc pH 6.2, 0.1% Sodium azide, 12 mM CaCl$_2$, 1% BSA and 0.15 micro-Ci/ml $^{125}$I-cAMP) were added. Following an 18 h incubation at 4° C. the plates were washed once and counted in a Wallac TriLux counter.

D1/D2 Dissections

Dopamine agonists can have activity at either the D1-like receptors, the D2-like receptors, or both. We have used the rotation response in rats with unilateral 6-OHDA lesions to assess compounds for their ability to stimulate both receptor types and induce rotation [Ungerstedt, Arbuthnott; Brain Res., 24, 485 (1970); Setler, Sarau, Zirkle, Saunders; Eur. J. Pharmacol., 50(4), 419 (1978); Ungerstedt, Herrera-Marschitz, Jungnelius, Ståhle, Tossman, Zetterström; in "Advances in Dopamine Research" (Kohsaka, Ed.), Pergamon Press, Oxford, p. 219 (1982)]. Experiments consist of determining a minimum effective dose (MED) to induce rotation for the compound in question. Once a MED has been determined, a second experiment is performed to determine the MED of the compound to overcome Nemonapride block (MED$_{Nemonapride}$). Nemonapride is a D2-like antagonist that blocks the D2-like receptor, therefore any observed rotations would be dependent upon activity at the D1-like receptor. Finally, once the MED$_{Nemonapride}$ is known a third experiment is run using the MED$_{Nemonapride}$ dose and observing the effect of the D1-like antagonist, SCH 23390 alone, the D2-like antagonist, Nemonapride alone and finally, the effect of combined treatment with SCH 23390 and Nemonapride. This third experiment confirms the activity of the compound at both receptors as either antagonist alone can only partially inhibit the rotation response induced by the test compound while the combination treatment completely blocks all rotations in the rats [Arnt, Hytell; Psychopharmacology, 85(3), 346 (1985); Sonsalla, Manzino, Heikkila; J. Pharmacol Exp. Ther., 247(1), 180 (1988)]. This model was validated using Apomorphine as the proof-of-principle compound for mixed D1-like/D2-like agonists.

D5 Assay

Human D5 (hD5) expression construct was made using a modified pEXJ vector. A stable cell line expressing a promiscuous human Galpha16 G protein (CHO-Ga16) was purchased from (Molecular Devices, Sunnyvale, Calif.). The cells were cultured in HAMS F-12 media (Invitrogen, Carlsbad, Calif.) containing 10% FSB, 1% L-glutamine and 1% penicillin/streptomycin (P/S) at 37° C. in 5% CO$_2$. 48 h before assay, CHO-Ga16 cells were transiently transfected with hD5 receptor DNA using a lipofectamine Plus method (Invitrogen, Carlsbad, Calif.), and allow to grow for 1 day in serum and P/S free media. 24 h before assay, hD5 transfected CHO-Ga16 cells were seeded at a density of 10,000 cells per well into black walled clear-base 384-well plates pretreated with poly-D-Lysine (Becton Dickinson, USA). The cells were then cultured in HAMS F-12 cell growth media containing 1.5% FBS, 1% L-glutamine and 1% penicillin/streptomycin (P/S) at 37° C. in 5% $CO_2$.

In Vitro Hepatocyte Assay

Cryopreserved pooled male rat hepatocytes (Sprague Dawley) and pooled human hepatocytes from 10 donors (male and female) were purchased from In Vitro Technologies Inc., BA, USA. Cells were thawed at 37° C. in a water bath, live cells counted and seeded in a total of 100 micro-L in Dulbecco's modified Eagle medium (high glucose) with 5 mM Hepes buffer in 96 well plates, each well containing 250.000 and 500.000 cells/mL for rat and human hepatocytes, respectively. Incubations were started after 15 min of pre-incubation and stopped at time points of 0, 5, 15, 30 and 60 min for rats and at 0, 30, 60, 90 and 120 min for human hepatocytes. Incubations were stopped by addition of an equal volumes of ice-cold acetonitrile containing 10% 1 M HCl. Following centrifugation, 20 micro-L of the supernatants were injected on a HPLC Column Atlantis dC18 3 micro-m, 150×2.1 mm i.d. (Waters, Mass., USA). The mobile phase had the following composition: A: 5% acetonitrile, 95% $H_2O$, 3.7 ml/l 25% aq. $NH_3$, 1.8 mL/L formic acid. Mobile phase B: 100% acetonitrile and 0.1% formic acid. The flow rate was 0.3 ml/min. The gradient operated from 0% to 75% B from 5 min to 20 min and the eluate was analyzed using a Q-TOFmicro mass spectrometer (Waters, Mass., USA).

Formation of the product/metabolite was confirmed by accurate mass measurements and comparison with a synthesized standard giving coinciding retention times.

Radioligand Binding Assay Results

The EC50 values for most the compounds in the present invention, exemplified above, at either the human D1 and D2 receptor was determined to be about 5.0 μM or less. The binding affinities for many of the compounds were determined to be about 1.0 μM or less. The binding affinities for several compounds were determined to be about 500 nM or less. The binding affinities for several compounds were determined to be 100 nM or less.

TABLE I

| EC 50 values of selected compounds | | | | | | |
|---|---|---|---|---|---|---|
| | Example No. | | | | | |
| | 3c | 3e | 5d2 | 5k | 7 | 8c |
| D1 EC 50 (μM) | >10 | 5.8 | >10 | 0.18 | 0.20 | >10 |
| D2 EC 50 (μM) | 0.11 | 0.03 | 1.4 | 0.002 | 0.00015 | 0.14 |

What is claimed:

1. A compound having the structure I

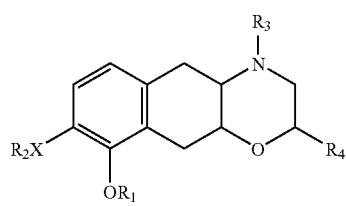

wherein
X is absent or oxygen
when X is oxygen, $R_1$ and $R_2$ are independently selected from hydrogen; $C_1$-$C_6$ alkanoyl; $C_6$-$C_{10}$ aryl-$C_1$-$C_6$ alkanoyl; or $R_1$ and $R_2$ are fused and form a methylene ($CH_2$) group;

when X is absent, $R_1$ is selected from hydrogen; $C_1$-$C_6$ alkyl; $C_1$-$C_6$ alkanoyl; $C_6$-$C_{10}$ aryl-$C_1$-$C_6$ alkanoyl; and $R_2$ is hydrogen;

$R_3$ is selected from the group consisting of hydrogen; $C_1$-$C_4$ alkyl; allyl; propargyl; $C_3$-$C_4$ cycloalkyl; hydroxyalkyl; $C_2$-$C_3$ haloalkyl;

$R_4$ is selected from the group consisting of hydrogen; $C_1$-$C_6$ alkyl; $C_6$-$C_{10}$ aryl-$C_1$-$C_6$ alkyl; heteroaryl-$C_1$-$C_6$ alkyl; di($C_1$-$C_6$ alkyl)amino-$C_1$-$C_6$ alkyl; $C_1$-$C_6$ alkylthio-$C_1$-$C_6$ alkyl; $C_1$-$C_6$ hydroxyalkyl; and $C_1$-$C_6$ haloalkyl, wherein each $C_6$-$C_{10}$ aryl and heteroaryl may be substituted with a substituent selected from halogen; $C_1$-$C_6$ alkyl; $C_1$-$C_6$ alkoxy, and enantiomers, diastereomers, tautomers and pharmaceutically acceptable addition salts thereof.

2. The compound according to claim 1 wherein X is oxygen.

3. The compound according to claim 1 wherein X is absent.

4. The compound according to claim 2 wherein $R_1$ and $R_2$ are both hydrogen.

5. The compound according to claim 2 wherein $R_1$ and $R_2$ are fused and form a methylene ($CH_2$) group.

6. The compound according to claim 2 wherein at least one of $R_1$ and $R_2$ is selected from the group consisting of $C_1$-$C_6$ alkanoyl, phenylacetyl and benzoyl.

7. The compound according to claim 3 wherein $R_1$ is hydrogen.

8. The compound according to claim 3 wherein $R_1$ is selected from the group consisting of $C_1$-$C_6$ alkanoyl, phenylacetyl and benzoyl.

9. The compound according to claim 1 wherein $R_4$ is hydrogen.

10. The compound according to claim 1 wherein $R_4$ is not hydrogen.

11. The compound according to claim 1 wherein $R_3$ is $C_1$-$C_4$ alkyl.

12. The compound according to claim 11 wherein $R_3$ is selected from the group consisting of methyl, ethyl and n-propyl.

13. The compound according to claim 1 wherein the heteroaryl group is selected from the group consisting of pyrazolyl, imidazolyl and 1,2,4-triazolyl.

14. The compound according to claim 1 for which $R_4$ is hydrogen, further characterized by being the substantially pure (4aR,10aR)-enantiomer.

15. The compound according to claim 1 for which $R_4$ is not hydrogen, further characterized by being the substantially pure (2R,4aR,10aR)-enantiomer.

16. The compound according to claim 1 for which $R_4$ is not hydrogen, further characterized by being the substantially pure (2S,4aR,10aR)-enantiomer.

17. The compound according to claim S for which $R_4$ is hydrogen, further characterized by being the substantially pure (6aR,10aR)-enantiomer.

18. The compound according to claim 5 for which $R_4$ is not hydrogen, further characterized by being the substantially pure (2R,6aR,10aR)-enantiomer.

19. The compound according to claim 5 for which $R_4$ is not hydrogen, further characterized by being the substantially pure (2S,6aR,10aR)-enantiomer.

20. The compound of claim 1, wherein the compound is selected from the group consisting of:
(4aR,10aR)-9-Methoxy-4-methyl-3,4,4a,5,10,10a-hexahydro-2H-naphtho[2,3-b][1,4]oxazine;
(4aS,10aS)-9-Methoxy-4-methyl-3,4,4a,5,10,10a-hexahydro-2H-naphtho[2,3-b][1,4]oxazine;
(4aR,10aR)-4-Ethyl-9-methoxy-3,4,4a,5,10,10a-hexahydro-2H-naphtho[2,3-b][1,4]oxazine;

(4aS,10aS)-4-Ethyl-9-methoxy-3,4,4a,5,10,10a-hexahydro-2H-naphtho[2,3-b][1,4]oxazine;
(4aR,10aR)-9-Methoxy-4-n-propyl-3,4,4a,5,10,10a-hexahydro-2H-naphtho[2,3-b][1,4]oxazine;
(4aS,10aS)-9-Methoxy-4-n-propyl-3,4,4a,5,10,10a-hexahydro-2H-naphtho[2,3-b][1,4]oxazine;
(4aR,10aR)-4-Allyl-9-methoxy-3,4,4a,5,10,10a-hexahydro-2H-naphtho[2,3-b][1,4]oxazine;
(4aS,10aS)-4-Allyl-9-methoxy-3,4,4a,5,10,10a-hexahydro-2H-naphtho[2,3-b][1,4]oxazine;
(4aR,10aR)-4-cyclo-Propylmethyl-9-methoxy-3,4,4a,5,10,10a-hexahydro-2H-naphtho[2,3-b][1,4]oxazine;
(4aS,10aS)-4-cyclo-Propylmethyl-9-methoxy-3,4,4a,5,10,10a-hexahydro-2H-naphtho[2,3-b][1,4]oxazine;
(2S,4aR,10aR)-9-Methoxy-4-n-propyl-2-[1,2,4]triazol-1-ylmethyl-3,4,4a,5,10,10a-hexahydro-2H-naphtho[2,3-b][1,4]oxazine;
(2R,4aR,10aR)-9-Methoxy-4-n-propyl-2-[1,2,4]triazol-1-ylmethyl-3,4,4a,5,10,10a-hexahydro-2H-naphtho[2,3-b][1,4]oxazine;
(2S,4aR,10aR)-9-Methoxy-2-methylsulfanylmethyl-4-n-propyl-3,4,4a,5,10,10a-hexahydro-2H-naphtho[2,3-b][1,4]oxazine;
(2R,4aR,10aR)-9-Methoxy-2-methylsulfanylmethyl-4-n-propyl-3,4,4a,5,10,10a-hexahydro-2H-naphtho[2,3-b][1,4]oxazine;
(2R,4aR,10aR)-2-Imidazol-1-ylmethyl-9-methoxy-4-n-propyl-3,4,4a,5,10,10a-hexahydro-2H-naphtho[2,3-b][1,4]oxazine;
(2R,4aR,10aR)-9-Methoxy-2-methoxymethyl-4-n-propyl-3,4,4a,5,10,10a-hexahydro-2H-naphtho[2,3-b][1,4]oxazine;
((2S,4aR,10aR)-9-Methoxy-4-n-propyl-3,4,4a,5,10,10a-hexahydro-2H-naphtho[2,3-b][1,4]oxazin-2-ylmethyl)-dimethylamine;
(2R,4aR,10aR)-2-Fluoromethyl-9-methoxy-4-n-propyl-3,4,4a,5,10,10a-hexahydro-2H-naphtho[2,3-b][1,4]oxazine;
(2S,4aR,10aR)-9-Methoxy-2-methyl-4-n-propyl-3,4,4a,5,10,10a-hexahydro-2H-naphtho[2,3-b][1,4]oxazine;
(2R,4aR,10aR)-9-Methoxy-4-n-propyl-2-pyrazol-1-ylmethyl-3,4,4a,5,10,10a-hexahydro-2H-naphtho[2,3-b][1,4]oxazine;
(2S,4aS,10aS)-9-Methoxy-4-n-propyl-2-pyrazol-1-ylmethyl-3,4,4a,5,10,10a-hexahydro-2H-naphtho[2,3-b][1,4]oxazine;
(2S,4aR,10aR)-9-Methoxy-4-n-propyl-2-pyrazol-1-ylmethyl-3,4,4a,5,10,10a-hexahydro-2H-naphtho[2,3-b][1,4]oxazine;
(2R,4aS,10aS)-9-Methoxy-4-n-propyl-2-pyrazol-1-ylmethyl-3,4,4a,5,10,10a-hexahydro-2H-naphtho[2,3-b][1,4]oxazine;
(2R,4aR,10aR)-2-(4-Chloro-pyrazol-1-ylmethyl)-9-methoxy-4-n-propyl-3,4,4a,5,10,10a-hexahydro-2H-naphtho[2,3-b][1,4]oxazine;
(2S,4aR,10aR)-2-(4-Chloro-pyrazol-1-ylmethyl)-9-methoxy-4-n-propyl-3,4,4a,5,10,10a-hexahydro-2H-naphtho[2,3-b][1,4]oxazine;
(2R,4aR,10aR)-9-Methoxy-2-(3-phenyl-pyrazol-1-ylmethyl)-4-n-propyl-3,4,4a,5,10,10a-hexahydro-2H-naphtho[2,3-b][1,4]oxazine;
(2S,4aR,10aR)-9-Methoxy-2-(3-phenyl-pyrazol-1-ylmethyl)-4-n-propyl-3,4,4a,5,10,10a-hexahydro-2H-naphtho[2,3-b][1,4]oxazine;
(4aR,10aR)-4-Ethyl-3,4,4a,5,10,10a-hexahydro-2H-naphtho[2,3-b][1,4]oxazin-9-ol;
(4aS,10aS)-4-Ethyl-3,4,4a,5,10,10a-hexahydro-2H-naphtho[2,3-b][1,4]oxazin-9-ol;
(4aR,10aR)-4-Methyl-3,4,4a,5,10,10a-hexahydro-2H-naphtho[2,3-b][1,4]oxazin-9-ol;
(4aS,10aS)-4-Methyl-3,4,4a,5,10,10a-hexahydro-2H-naphtho[2,3-b][1,4]oxazin-9-ol;
(4aR,10aR)-4-n-Propyl-3,4,4a,5,10,10a-hexahydro-2H-naphtho[2,3-b][1,4]oxazin-9-ol;
(4aS,10aS)-4-n-Propyl-3,4,4a,5,10,10a-hexahydro-2H-naphtho[2,3-b][1,4]oxazin-9-ol;
(4aR,10aR)-4-Allyl-3,4,4a,5,10,10a-hexahydro-2H-naphtho[2,3-b][1,4]oxazin-9-ol;
(4aS,10aS)-4-Allyl-3,4,4a,5,10,10a-hexahydro-2H-naphtho[2,3-b][1,4]oxazin-9-ol;
(4aR,10aR)-4-cyclo-Propylmethyl-3,4,4a,5,10,10a-hexahydro-2H-naphtho[2,3-b][1,4]oxazin-9-ol;
(4aS,10aS)-4-cyclo-Propylmethyl-3,4,4a,5,10,10a-hexahydro-2H-naphtho[2,3-b][1,4]oxazin-9-ol;
(2R,4aR,10aR)-2-Hydroxymethyl-4-n-propyl-3,4,4a,5,10,10a-hexahydro-2H-naphtho[2,3-b][1,4]oxazin-9-ol;
(2S,4aS,10aS)-2-Hydroxymethyl-4-n-propyl-3,4,4a,5,10,10a-hexahydro-2H-naphtho[2,3-b][1,4]oxazin-9-ol;
(2S,4aR,10aR)-2-Hydroxymethyl-4-n-propyl-3,4,4a,5,10,10a-hexahydro-2H-naphtho[2,3-b][1,4]oxazin-9-ol;
(2R,4aS,10aS)-2-Hydroxymethyl-4-n-propyl-3,4,4a,5,10,10a-hexahydro-2H-naphtho[2,3-b][1,4]oxazin-9-ol;
(2S,4aR,10aR)-4-n-Propyl-2-[1,2,4]triazol-1-ylmethyl-3,4,4a,5,10,10a-hexahydro-2H-naphtho[2,3-b][1,4]oxazin-9-ol;
(2R,4aR,10aR)-4-n-Propyl-2-[1,2,4]triazol-1-ylmethyl-3,4,4a,5,10,10a-hexahydro-2H-naphtho[2,3-b][1,4]oxazin-9-ol;
(2S,4aR,10aR)-2-Methylsulfanylmethyl-4-n-propyl-3,4,4a,5,10,10a-hexahydro-2H-naphtho[2,3-b][1,4]oxazin-9-ol;
(2R,4aR,10aR)-2-Methylsulfanylmethyl-4-n-propyl-3,4,4a,5,10,10a-hexahydro-2H-naphtha[2,3-b][1,4]oxazin-9-ol;
(2S,4aR,10aR)-2-Methyl-4-n-propyl-3,4,4a,5,10,10a-hexahydro-2H-naphtho[2,3-b][1,4]oxazin-9-ol;
(2R,4aR,10aR)-2-Imidazol-1-ylmethyl-4-n-propyl-3,4,4a,5,10,10a-hexahydro-2H-naphtho[2,3-b][1,4]oxazin-9-ol;
(2R,4aR,10aR)-2-Methoxymethyl-4-n-propyl-3,4,4a,5,10,10a-hexahydro-2H-naphtho[2,3-b][1,4]oxazin-9-ol;
(2S,4aR,10aR)-2-Dimethylaminomethyl-4-n-propyl-3,4,4a,5,10,10a-hexahydro-2H-naphtho[2,3-b][1,4]oxazin-9-ol;
(2R,4aR,10aR)-2-Fluoromethyl-4-n-propyl-3,4,4a,5,10,10a-hexahydro-2H-naphtho[2,3-b][1,4]oxazin-9-ol;
(2R,4aR,10aR)-4-n-Propyl-2-pyrazol-1-ylmethyl-3,4,4a,5,10,10a-hexahydro-2H-naphtho[2,3-b][1,4]oxazin-9-ol;
(2S,4aS,10aS)-4-N-Propyl-2-pyrazol-1-ylmethyl-3,4,4a,5,10,10a-hexahydro-2H-naphtho[2,3-b][1,4]oxazin-9-ol;
(2S,4aR,10aR)-4-n-Propyl-2-pyrazol-1-ylmethyl-3,4,4a,5,10,10a-hexahydro-2H-naphtho[2,3-b][1,4]oxazin-9-ol;
(2R,4aS,10aS)-4-n-Propyl-2-pyrazol-1-ylmethyl-3,4,4a,5,10,10a-hexahydro-2H-naphtho[2,3-b][1,4]oxazin-9-ol;
(2R,4aR,10aR)-2-(4-Chloro-pyrazol-1-ylmethyl)-4-n-propyl-3,4,4a,5,10,10a-hexahydro-2H-naphtho[2,3-b][1,4]oxazin-9-ol;
(2S,4aR,10aR)-2-(4-Chloro-pyrazol-1-ylmethyl)-4-n-propyl-3,4,4a,5,10,10a-hexahydro-2H-naphtho[2,3-b][1,4]oxazin-9-ol;
(2R,4aR,10aR)-2-(3-Phenyl-pyrazol-1-ylmethyl)-4-n-propyl-3,4,4a,5,10,10a-hexahydro-2H-naphtho[2,3-b][1,4]oxazin-9-ol;
(2S,4aR,10aR)-2-(3-Phenyl-pyrazol-1-ylmethyl)-4-n-propyl-3,4,4a,5,10,10a-hexahydro-2H-naphtho[2,3-b][1,4]oxazin-9-ol;

(4aR,10aR)-4-n-Propyl-3,4,4a,5,10,10a-hexahydro-2H-naphtho[2,3-b][1,4]oxazine-8,9-diol;

(6aR,10aR)-7-Methyl-6a,7,8,9,10a,11-hexahydro-6H-1,3,10-trioxa-7-aza-cyclopenta[a]anthracene;

(6aR,10aR)-7-Ethyl-6a,7,8,9,10a,11-hexahydro-6H-1,3,10-trioxa-7-aza-cyclopenta[a]anthracene; and (6aR,10aR)-7-n-Propyl-6a,7,8,9,10a,11-hexahydro-6H-1,3,10-trioxa-7-aza-cyclopenta[a]anthracene or a pharmaceutically acceptable addition salt thereof.

21. A pharmaceutical composition comprising a therapeutically effective amount of a compound of claim 1 and a pharmaceutically acceptable carrier or diluent.

22. A method for treating a subject suffering from a neurodegenerative disorder selected from Parkinson's disease and Huntington's disease comprising administering to the subject a therapeutically effective amount of a compound of claim 1 or a pharmaceutically acceptable salt thereof.

23. The method according to claim 22 wherein the neurodegenerative disorder is Parkinson's disease.

24. The method according to claim 22 wherein the neurodegenerative disorder is Huntington's disease.

* * * * *